(12) United States Patent
Levine et al.

(10) Patent No.: US 11,229,653 B2
(45) Date of Patent: Jan. 25, 2022

(54) METHODS OF TREATMENT OF MYELOPROLIFERATIVE NEOPLASM

(71) Applicant: Memorial Sloan Kettering Cancer Center, New York, NY (US)

(72) Inventors: Ross L. Levine, New York, NY (US); Anna Sophia McKenney, Selkirk, NY (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/615,115

(22) PCT Filed: May 4, 2018

(86) PCT No.: PCT/US2018/031090
§ 371 (c)(1),
(2) Date: Nov. 19, 2019

(87) PCT Pub. No.: WO2018/204787
PCT Pub. Date: Nov. 8, 2018

(65) Prior Publication Data
US 2020/0155559 A1 May 21, 2020

Related U.S. Application Data

(60) Provisional application No. 62/535,146, filed on Jul. 20, 2017, provisional application No. 62/502,456, filed on May 5, 2017.

(51) Int. Cl.
| | | |
|---|---|---|
| *A61K 31/53* | (2006.01) | |
| *A61P 35/00* | (2006.01) | |
| *A61K 31/519* | (2006.01) | |
| *A61K 9/00* | (2006.01) | |

(52) U.S. Cl.
CPC .......... *A61K 31/53* (2013.01); *A61K 31/519* (2013.01); *A61P 35/00* (2018.01); *A61K 9/0053* (2013.01)

(58) Field of Classification Search
None
See application file for complete search history.

(56) References Cited

U.S. PATENT DOCUMENTS

| | | | |
|---|---|---|---|
| 9,512,107 B2 * | 12/2016 | Cianchetta | C07D 413/04 |
| 9,656,999 B2 | 5/2017 | Cianchetta et al. | |
| 9,694,013 B2 | 7/2017 | Agresta et al. | |
| 9,724,350 B2 | 8/2017 | Travins et al. | |
| 9,732,062 B2 | 8/2017 | Cianchetta et al. | |
| 9,738,625 B2 | 8/2017 | Agresta et al. | |
| 9,751,863 B2 | 9/2017 | Zhang et al. | |
| 9,889,137 B2 | 2/2018 | Agresta | |
| 10,093,654 B2 | 10/2018 | Agresta et al. | |
| 10,105,369 B2 | 10/2018 | Agresta | |
| 10,111,878 B2 | 10/2018 | Travins et al. | |
| 10,137,130 B2 | 11/2018 | Amatangelo et al. | |
| 10,188,656 B2 | 1/2019 | Wu et al. | |
| 10,201,543 B2 | 2/2019 | Kluge | |
| 10,294,215 B2 | 5/2019 | Cianchetta et al. | |
| 10,434,105 B2 | 10/2019 | Kluge | |
| 10,695,352 B2 | 6/2020 | Chopra et al. | |
| 10,730,854 B2 | 8/2020 | Agresta et al. | |
| 10,905,692 B2 | 2/2021 | Agresta et al. | |
| 2002/0051820 A1 | 5/2002 | Shell et al. | |
| 2003/0039688 A1 | 2/2003 | Shell et al. | |
| 2003/0104053 A1 | 6/2003 | Gusler et al. | |
| 2003/0104062 A1 | 6/2003 | Berner et al. | |
| 2012/0121515 A1 | 5/2012 | Dang et al. | |

FOREIGN PATENT DOCUMENTS

| | | |
|---|---|---|
| WO | WO 2011/050210 | 4/2011 |
| WO | WO 2013/102431 | 11/2013 |
| WO | WO 2015/018060 | 2/2015 |
| WO | WO 2015/017821 | 5/2015 |
| WO | WO 2017/146794 | 8/2017 |
| WO | WO 2017/146795 | 8/2017 |

OTHER PUBLICATIONS

National Center for Biotechnology Information. "PubChem Compound Summary for CID 16722836, Fedratinib" PubChem, https://pubchem.ncbi.nlm.nih.gov/compound/Fedratinib. Accessed Apr. 27, 2021. Create Sep. 3, 2007. (Year: 2007).*
Harrison et al., "Ruxolitinib: a potent and selective Janus kinase 1 and 2 inhibitor in patients with myelofibrosis. An update for clinicians", 2012, Ther. Adv. Hematol., 3(6), pp. 341-354. (doi: 10.1177/2040620712459746) (Year: 2012).*
National Organization for Rare Disorders (NORD), definition of "Primary Myelofibrosis", https://rarediseases.org/rare-diseases/primary-myelofibrosis/. (Year: 2018).*
Abdulkarim et al, "AML transformation in 56 patients with Ph-MPD in two well defined populations", *European Journal of Haematology*, 2009;82:106-111.
Aghili et al., "Hydroxyglutaric aciduria and malignant brain tumor: a case report and literature review," J Neurooncol 91, 233 6 (2009).
Berge et al.,"Pharmaceutically Acceptable Salts." J. Pharm. Sci. v.66, 1-19 (1977).
Dang et al, "Cancer-associated IDH1 mutations produce 2-hydroxyglutarate" Nature Dec. 10, 2009; v.462:739-744.
Figueroa et al., "Leukemic IDH1 and IDH2 Mutations Result in a Hypermethylation Phenotype, Disrupt TET2 Function, and Impair Hematopoietic Differentiation," *Cancer Cell* 18:553-567 (2010).
Gangat et al. "Myelodysplastic syndromes: Contemporary review and how we treat", American Journal of Hematology, 91:76-89, 2016.
Gangat et al., "Leucocytosis in polycythaemia vera predicts both inferior survival and leukaemic transformation", Blackwell Publishing Ltd, British Journal of Haematology, 138, 354-358 (2007).
International Search Report and Written Opinion on PCT/US2018/03109 dated Jul. 11, 2018 (15 pages).
Kaelin et al., "Influence of Metabolism on Epigenetics and Disease", Cell 153, Mar. 28, 2013; 56-69.

(Continued)

*Primary Examiner* — My-Chau T. Tran
(74) *Attorney, Agent, or Firm* — Jones Day

(57) ABSTRACT

Provided are methods and compositions for treating myeloproliferative neoplasms patients carrying an IDH2 mutation and a JAK2 mutation.

23 Claims, 53 Drawing Sheets

(56) References Cited

OTHER PUBLICATIONS

Kats et al. "A Pharmacogenomic Approach Validates AG-221 as an Effective and On-Target Therapy in IDH2 Mutant AML", *Leukemia*, 31:6, 1466-1470 (2017).

Kats et al., "Proto-Oncogenic Role of Mutant IDH2 in Leukemia Initiation and Maintenance", Cell Stem Cell 2014;14:329-341.

Kolker, S. et al. "NMDA receptor activation and respiratory chain complex V inhibition contribute to neurodegeneration in D-2-hydroxyglutaric aciduria", European Journal of Neuroscience, 16, 21-28, (2002).

Kolker, S. et al., "White matter disease in cerebral organic acid disorders: clinical implications and suggested pathomechanisms," Neuropediatrics 33, 225 31 (2002).

Kuhn et al., "Inducible Gene Targeting in Mice" Science. Sep. 8, 1995, 269 (5229): 1427-1429.

Latini, A. et al., "D-2-hydroxyglutaric acid induces oxidative stress in cerebral cortex of young rats", European Journal of Neuroscience, 2017-2022, (2003).

Lu et al., "Expression of a Homodimeric Type I Cytokine Receptor Is Required for JAK2V617F-Mediated Transformation", Proceedings of the National Academy of Sciences of the United States of America, 102: 52, Theoretical Framework for Business Growth (Dec. 27, 2005), 18962-18967.

Lu et al. "Metabolic Regulation of Epigenetics", Cell Metabolism 16, Jul. 3, 2012; 9-17.

McKenney et al., "JAK2/IDH-mutant-driven myeloproliferative neoplasm is sensitive to combined targeted inhibition", J Clin Invest. 2018;128(2):789-804. https://doi.org/10.1172/JCI94516.

Mesa et al., "Leukemic transformation in myelofibrosis with myeloid metaplasia: a single-institution experience with 91 cases", Blood 2005;105:973-7.

Mullaly et al., "Physiological Jak2V617F Expression Causes a Lethal Myeloproliferative Neoplasm with Differential Effects on Hematopoietic Stem and Progenitor Cells", Cancer Cell, 2010;17:584-596.

Passamonti et al. "Leukemic Transformation of Polycythemia Vera: A Single Center Study of 23 Patients", American Cancer Society, Jul. 26, 2005;104:1032-1036.

Pemmaraju, et al. "A Phase I/II Study of the Janus Kinase (JAK)1 and 2 Inhibitor Ruxolitinib in Patients With Relapsed or Refractory Acute Myeloid Leukemia", Clinical Lymphoma, Myeloma & Leukemia, Sep. 1, 2014.

Pronk et al., "Elucidation of the Phenotypic, Functional, and Molecular Topography of a Myeloerythroid Progenitor Cell Hierarchy", Cell Stem Cell 2007;1:428-442.

Quintas-Cardama et al., "Preclinical characterization of the selective JAK1/2 inhibitor INCB018424: therapeutic implications for the treatment of myeloproliferative neoplasms", Blood, 2010;115:3109-17.

Shih et al., "Combination Targeted Therapy to Disrupt Aberrant Oncogenic Signaling and Reverse Epigenetic Dysfunction in IDH2- and TET2-Mutant Acute Myeloid Leukemia", American Association for Cancer Research, Cancer Discovery, 2017: 494-505.

Shih et al., "Mutational Cooperativity Linked to Combinatorial Epigenetic Gain of Function in Acute Myeloid Leukemia", Cancer Cell 2015; 27:502-15.

Stein et al., "Molecular Pathways: IDH2 Mutations—Co-Opting Cellular Metabolism for Malignant Transformation", Clinical Cancer Research, vol. 22, No. 1, Nov. 9, 2015, pp. 16-19.

Struys, E. A. et al., "Mutations in the D-2-Hydroxyglutarate Dehydrogenase Gene Cause D-2-Hydroxyglutaric Aciduria" Am. J. Hum. Genet. 76, 358 60 (2005)).

Tefferi, A., "Myeloproliferative neoplasms: A decade of discoveries and treatment advances", American Journal of Hematology, 91:50-58, 2016.

Thomas, et al. "Optimizing Next-Generation AML Therapy: Activity of Mutant IDH2 Inhibitor AG-221 in Preclinical Models", Cancer Discovery, vol. 7, No. 5, Apr. 30, 2017.

Verstovsek et al., "A double-blind, placebo-controlled trial of ruxolitinib for myelofibrosis", New England Journal of Medicine 2012; 366; 799-807.

Verstovsek et al., "Safety and Efficacy of INCB018424, a JAK1 and JAK2 Inhibitor, in Myelofibrosis", New England Journal of Medicine 2010;363:1117-27.

Wajner, M. et al., "The Role of Oxidative Damage in the Neuropathology of Organic Acidurias: Insights from Animal Studies", J. Inherit. Metab.Dis. 27: 427-448 (2004)).

Wang et al. "Targeted Inhibition of Mutant IDH2 in Leukemia Cells Induces Cellular Differentiation", Science, 340; 622-626 (2013).

Xu et al., "Oncometabolite 2-Hydroxyglutarate Is a Competitive Inhibitor of α-Ketoglutarate-Dependent Dioxygenases", Cancer Cell, 2011;19:17-30.

Yen et al., "AG-221, a First-in-Class Therapy Targeting Acute Myeloid Leukemia Harboring Oncogenic IDH2 Mutations", Cancer Discovery, 2017; 479-493.

* cited by examiner

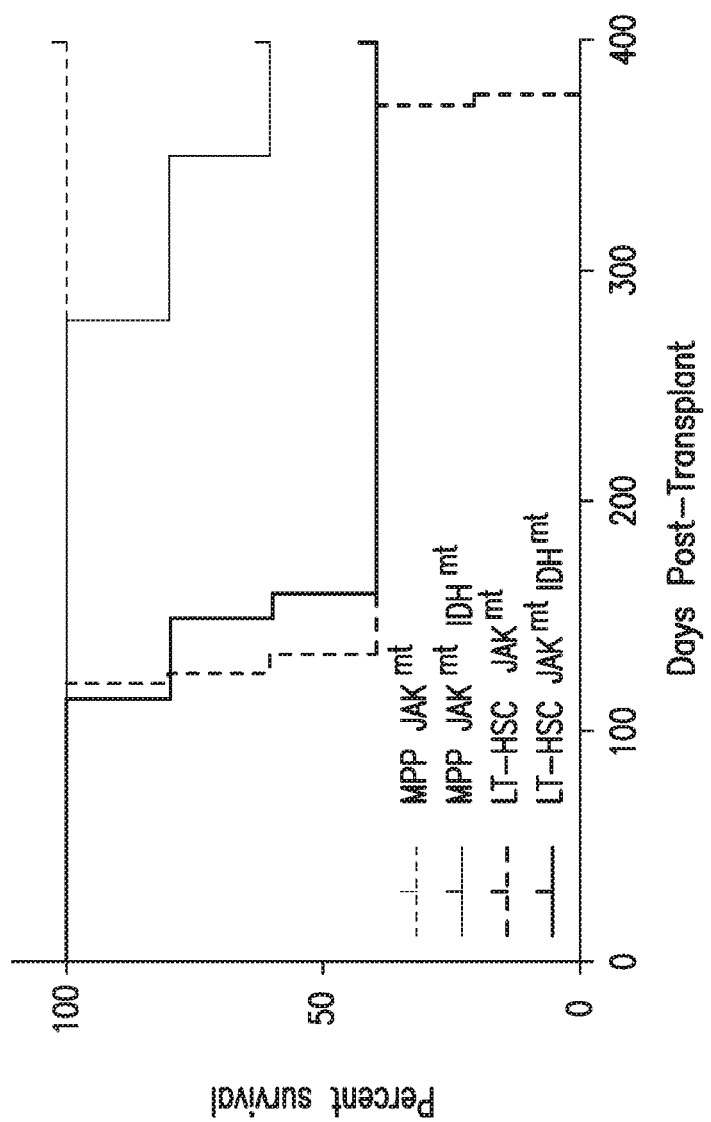

METHODS OF TREATMENT OF MYELOPROLIFERATIVE NEOPLASM

CROSS REFERENCE TO RELATED APPLICATIONS

This application is a U.S. National Stage filing under 35 U.S.C. § 371 of International Application No. PCT/US2018/031090, filed May 4, 2018, which claims the benefit of the priority to U.S. Provisional Application Nos. 62/502,456, filed May 5, 2017, and 62/535,146, filed Jul. 20, 2017, the disclosures of each of which are incorporated herein by reference in their entireties.

FIELD

Provided herein are methods of treating a myeloproliferative neoplasm (MPN) and acute myeloid leukemia (AML) characterized by the presence of a mutant allele of IDH2 and a mutant allele of JAK2.

Also provided herein is COMPOUND 1 for use in such methods of treating MPN or AML, characterized by the presence of a mutant allele of IDH2 and a mutant allele of JAK2, wherein COMPOUND 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2- ol has the following formula:

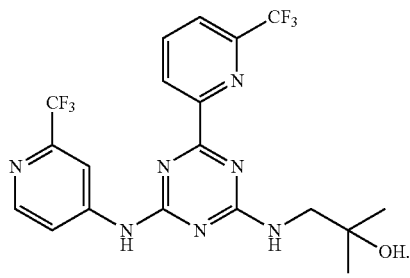 [SMILES: CC(C)(O)CNc1nc(Nc2ccnc(C(F)(F)F)c2)nc(-c2cccc(C(F)(F)F)n2)n1]

BACKGROUND

Myeloproliferative Neoplasms (MPN) are clonal myeloid malignancies characterized by somatic mutations acquired in hematopoietic stem/progenitor cells, which drive expansion of one or more myeloid lineages. Although MPN patients can live with their disease for years, a subset of MPN patients progress to bone marrow failure or acute myeloid leukemia (AML), which are associated with poor clinical outcome. See Mesa et al., Leukemic transformation in myelofibrosis with myeloid metaplasia: a single-institution experience with 91 cases, *Blood* 2005;105:973-7; Passamonti et al. Leukemic transformation of polycythemia vera: a single center study of 23 patients, *Cancer,* 2005;104: 1032-6; Gangat N, et al., Leucocytosis in polycythaemia vera predicts both inferior survival and leukaemic transformation, *British Journal of Haematology,* 2007;138:354-8; Abdulkarim et al, AML transformation in 56 patients with Ph-MPD in two well defined populations, *European Journal of Haematology,* 2009;82:106-11. Patients with accelerated or transformed disease do not respond to conventional anti-leukemic therapies, including cytotoxic chemotherapy. See Mesa et al., Leukemic transformation in myelofibrosis with myeloid metaplasia: a single-institution experience with 91 cases, *Blood* 2005;105:973-7. As such, there is a need to for therapies for MPN and AML patients, including MPN and AML patients carrying IDH2 and JAK2 mutations.

SUMMARY

In one embodiment, provided herein is COMPOUND 1 for use in such methods of treating MPN or AML, characterized by the presence of a mutant allele of IDH2 and a mutant allele of JAK2, wherein COMPOUND 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol has the following formula:

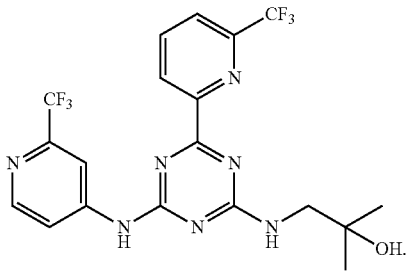 [SMILES: CC(C)(O)CNc1nc(Nc2ccnc(C(F)(F)F)c2)nc(-c2cccc(C(F)(F)F)n2)n1]

In one embodiment, provided herein is a method of treating MPN in a subject comprising administering to the subject a therapeutically effective amount of an IDH2 inhibitor in combination with a therapeutically effective amount of a JAK2 inhibitor, wherein the subject harbors a mutant allele of IDH2 and a mutant allele of JAK2. In one embodiment, provided herein is a method of treating AML in a subject comprising administering to the subject a therapeutically effective amount of an IDH2 inhibitor in combination with a therapeutically effective amount of a JAK2 inhibitor, wherein the subject harbors a mutant allele of IDH2 and a mutant allele of JAK2. Accordingly, in one embodiment, provided herein is COMPOUND 1 for use in the method of treating MPN in a subject comprising administering to the subject a therapeutically effective amount of an IDH2 inhibitor in combination with a therapeutically effective amount of a JAK2 inhibitor, wherein the subject harbors a mutant allele of IDH2 and a mutant allele of JAK2. In one embodiment, provided herein is a method of treating AML in a subject comprising administering to the subject a therapeutically effective amount of an IDH2 inhibitor in combination with a therapeutically effective amount of a JAK2 inhibitor, wherein the subject harbors a mutant allele of IDH2 and a mutant allele of JAK2.

In certain embodiments, provided herein is a method of treating MPN in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2. In certain embodiments, the JAK2 inhibitor for use in the methods provided herein is selected from INCB018424 (ruxolitinib), TG101348, CYT387, AZD1480, SB1518 (pacritinib), XL019, NCBO-16562, NVP-BSK805, R723, hydroxycarbamide, SAR302503, CP-690,550 (tasocitinib) and INCB16562. In one embodiment, the JAK2 inhibitor is ruxolitinib. Accordingly, provided herein is COMPOUND 1 for use in the method of treating MPN in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2.

In certain embodiments, provided herein is a method of treating AML in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2. Accordingly, provided herein is COMPOUND 1 for use in the method of treating AML in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2. In certain embodiments, the JAK2 inhibitor for use in the methods provided herein is selected from INCB018424 (ruxolitinib), TG101348, CYT387, AZD1480, SB1518 (pacritinib), XL019, NCBO-16562, NVP-BSK805, R723, hydroxycarbamide, SAR302503, CP-690,550 (tasocitinib) and INCB16562. In one embodiment, the JAK2 inhibitor is ruxolitinib.

In certain embodiments, provided herein is a method of treating a high risk MPN in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2. Accordingly, provided herein is COMPOUND 1 for use in the method of treating high risk MPN in a subject comprising administering to the subject a therapeutically effective amount of COMPOUND 1 in combination with a therapeutically effective amount of a JAK2 inhibitor, wherein the subject harbors a mutant allele of IDH2 and a mutant allele of JAK2. In certain embodiments, the JAK2 inhibitor for use in the methods provided herein is selected from INCB018424 (ruxolitinib), TG101348, CYT387, AZD1480, SB1518 (pacritinib), XL019, NCBO-16562, NVP-BSK805, R723, hydroxycarbamide, SAR302503, CP-690,550 (tasocitinib) and INCB16562. In one embodiment, the JAK2 inhibitor is ruxolitinib.

In certain embodiments, the mutant allele of IDH2 is mIDH2-R140 or mIDH2-R172.

In certain embodiments, the mutant allele of IDH2 is mIDH2-R140Q, mIDH2-R140W, mIDH2-R140L, mIDH2-R172K, or mIDH2-R172G.

In certain embodiments, the mutant allele of JAK2 is mJAK2-V617F.

BRIEF DESCRIPTION OF THE DRAWINGS

FIG. 1A provides Kaplan-Meier survival curve for primary IDH1$^{R132H}$JAK2$^{V617F}$MX1-cre mice following recombination. FIG. 1B provides Kaplan-Meier survival curve for secondary transplant mice following injection of IDH1$^{R132H}$JAK2$^{V617F}$MX1-cre bone marrow. FIG. 1C provides % hematocrit and leukocyte count in peripheral blood in mice having mutant IDH1, mutant JAK2 and a combination of mutant IDH1 and mutant JAK2. FIG. 1D provides % spleen weight in mice having mutant IDH1, mutant JAK2 and a combination of mutant IDH1 and mutant JAK2. FIG. 1E provides 2 HG concentration in plasma in mice having mutant IDH1, mutant JAK2 and a combination of mutant IDH1 and mutant JAK2. FIG. 1F provides representative histology photos for CD34 immunohistochemical stains of bone marrow and H&E stains of spleens of primary IDH1$^{R132H}$JAK2$^{V617F}$Mx1-cre mice sacrificed at approximately 6 months of age. (N=5 per group). FIG. 1G provides % hematocrit and leukocyte count in peripheral blood in mice having mutant IDH2, mutant JAK2 and a combination of mutant IDH2 and mutant JAK2. FIG. 1H provides % spleen weight in mice having mutant IDH2, mutant JAK2 and a combination of mutant IDH2 and mutant JAK2. FIG. 1I provides 2 HG concentration in plasma in mice having mutant IDH2, mutant JAK2 and a combination of mutant IDH2 and mutant JAK2. FIG. 1J provides representative histology photos for CD34 immunohistochemical stains of bone marrow, Wright-Giemsa stains of bone marrow cytospins, and H&E stains of spleens of primary IDH2$^{R140Q}$JAK2$^{V617F}$Mx1-cre mice sacrificed at approximately 6 months of age. (N=4-5 per group).

FIG. 2A illusttrares donor chimerism of competitive transplants with IDH2$^{R140Q}$JAK2$^{V617F}$ bone marrow over time (N=5 per group) and at 12 weeks (N=5-50 per group). FIG. 2B provides peripheral blood chimerism, hematocrit levels, and platelet counts in recipients of bone marrow sorted for MPP (multipotent progenitors) or LT-HSC (long-term hematopoietic stem cells) LSK populations, 15 weeks after injection (N=5 per group). FIG. 2C provides total number of LSKs in JAK2/IDH-mutant mice. FIG. 2D provides total number of myeloprogenitors in bone marrow of primary IDH2$^{R140Q}$JAK2$^{V617F}$ mice and controls according to stem cell/progenitor compartment as measured by FACS (Fluorescence-activated cell sorting) (N=4-5 per group). FIG. 2E provides megakaryocyte progenitor populations as measured by FACS in bone marrow of primary IDH2$^{R140Q}$JAK2$^{V617F}$ mice expressed as a proportion of lineage negative cells (N=4-5 per group). FIG. 2F provides erythrocytic progenitor populations as measured by FACS in bone marrow of primary IDH2$^{R140Q}$JAK2$^{V617F}$ mice expressed as a proportion of lineage negative cells (N=4-5 per group). FIG. 2G provides granulocytic progenitor populations as measured by FACS in bone marrow of primary IDH2$^{R140Q}$JAK2$^{V617F}$ mice expressed as a proportion of lineage negative cells (N=4-5 per group).

FIG. 3A provides 2HG levels in plasma in transplant recipients of IDH2$^{R140Q}$JAK2$^{V617F}$ bone marrow treated with targeted inhibitors at sacrifice after four weeks of treatment (N=7-10 per group). FIG. 3B provides spleen weights in transplant recipients of IDH2$^{R140Q}$JAK2$^{V617F}$ bone marrow treated with targeted inhibitors at sacrifice after four weeks of treatment (N=7-10 per group). FIG. 3C provides hematocrit levels and leukocyte counts in transplant recipients of IDH2$^{R140Q}$JAK2$^{V617F}$ bone marrow treated with targeted inhibitors at sacrifice after four weeks of treatment (N=7-10 per group). FIG. 3D provides total LSK cells classified by compartment in transplant recipients of IDH2$^{R140Q}$JAK2$^{V617F}$ bone marrow treated with targeted inhibitors at sacrifice after four weeks of treatment (N=7-10 per group). FIG. 3E provides total myeloprogenitors classified by compartment in transplant recipients of IDH2$^{R140Q}$JAK2$^{V617F}$ bone marrow treated with targeted inhibitors at sacrifice after four weeks of treatment (N=7-10 per group). FIG. 3F provides erythrocytic progenitors classified by compartment in transplant recipients of IDH2$^{R140Q}$JAK2$^{V617F}$ bone marrow treated with targeted inhibitors at sacrifice after four weeks of treatment (N=7-10 per group). FIG. 3G provides megakaryocyte progenitors classified by compartment in transplant recipients of IDH2$^{R140Q}$JAK2$^{V617F}$ bone marrow treated with targeted inhibitors at sacrifice after four weeks of treatment (N=7-10 per group). FIG. 3H provides granulocytic progenitors classified by compartment in transplant recipients of IDH2$^{R140Q}$JAK2$^{V617F}$ bone marrow treated with targeted inhibitors at sacrifice after four weeks of treatment (N=7-10 per group) as measured by FACS. FIG. 3I provides paired evaluation of donor chimerism in peripheral blood of IDH2$^{R140Q}$JAK2$^{V617F}$ bone marrow recipients before and after treatment with targeted inhibitors for four weeks (N=7 per group). FIG. 3J provides total LSK compartment expressed as proportion of total lineage negative and as proportions of LSK subcompartments. FIG. 3K provides total myeloid progenitors expressed as proportion of total lineage negative and as proportions of LSK subcompartments. FIG. 3L provides erythroid progenitors expressed as proportions of early, middle, and late-maturity cells. FIG. 3M provides representative images of bone marrow morphology with diletations, CD34 immunohistochemical stain in the bone marrow, and spleen cell/blast morphology in IDH2$^{R140Q}$JAK2$^{V617F}$ bone marrow recipients treated with targeted inhibitors.

FIG. 4A provides significantly enriched Hallmark GSEA in comparative expression patterns comparing vehicle/diseased mice to wild type in IDH2$^{R140Q}$JAK2$^{V617F}$ bone marrow recipients treated with targeted inhibitors (N=3 per group). FIG. 4B provides clustering of all treated mice depicting comparative phylogeny of samples and relative expression of 100 most significantly differentially expressed genes. FIG. 4C provides examination of genes differentially expressed between combined treated mice and vehicle treated mice using geneset defined with genes differentially expressed between wild type mice and vehicle mice. FIGS. 4D and 4E provide calculated NES values (y-axis) and FDR (on x-axis) of curated Hallmark GSEA, demonstrating level and significance of enrichment in each treatment group in comparison to wild type examined for enrichment in curated Hallmark GSEA lists related to JAK-STAT signaling. FIG. 4D highlights several pathways related to JAK-STAT signaling. FIG. 4E highlights several classical oncogenic pathways. Statistically significantly non-zero NES values are depicted in saturated colors while non-statistically significant NES values are depicted in desaturated colors. FIGS. 4F, 4G and 4H provide mass spectroscopic analysis of metabolites from whole bone marrow aspirate cells in treated and wild type mice, normalized to leucine level. FIG. 4F provides 2-hydroxyglutarate levels, FIG. 4G provides citrate, α-ketoglutarate, succinate, fumarate, and malate levels respectively, and FIG. 4H provides glutamine and glutamate levels, respectively.

FIG. 5A provides colony counts of cultured cells classified by colony morphology including Granulocyte-macrophage (GM) and Burst Forming Unit-Erythroid (BFU-E) colonies. FIG. 5B provides representative images of colonies taken during culture of cells from MPN PT 71. FIG. 5C provides expression levels of cell surface markers on cultured cells after therapy as measured by Mean Fluorescence Intensity (MFI) using FACS anitbody CD117. FIG. 5D provides expression levels of cell surface markers on cultured cells after therapy as measured by Mean Fluorescence Intensity (MFI) using FACS anitbody CD235a. FIG. 5E provides expression levels of cell surface markers on cultured cells after therapy as measured by Mean Fluorescence Intensity (MFI) using FACS anitbody CD14.

FIG. 6A-FIG. 6I provide combined mutant mouse phenotype. FIG. 6A provides peripheral blood leukocyte counts and hematocrit from recipients of competitive transplants 12 weeks post-transplant. FIG. 6B provides a representative image of gates used to sort LSK populations for injection into recipients. FIG. 6C provides a survival curve of mice injected with different LSK populations. FIG. 6D provides LSK populations in primary IDH2$^{R140Q}$JAK2$^{V617F}$ mice represented as proportions of total LSK. FIG. 6E provides LSK populations in primary IDH2R$^{140Q}$JAK2$^{V617F}$ mice represented as totals and proportions of total LSK. FIG. 6F provides myeloprogenitor populations in primary IDH2$^{R140Q}$JAK2$^{V617F}$ mice represented as proportions of total LSK. FIG. 6G provides myeloprogenitor populations in primary IDH2$^{R140Q}$JAK2$^{V617F}$ mice represented as totals and proportions of total LSK. FIG. 6H provides LSK, and FIG. 6I provides myeloprogenitor compartments expressed as proportions of subcompartments in IDH2$^{R140Q}$JAK2$^{V617F}$ bone marrow recipients treated with targeted inhibitors.

DETAILED DESCRIPTION

Figure 1A:
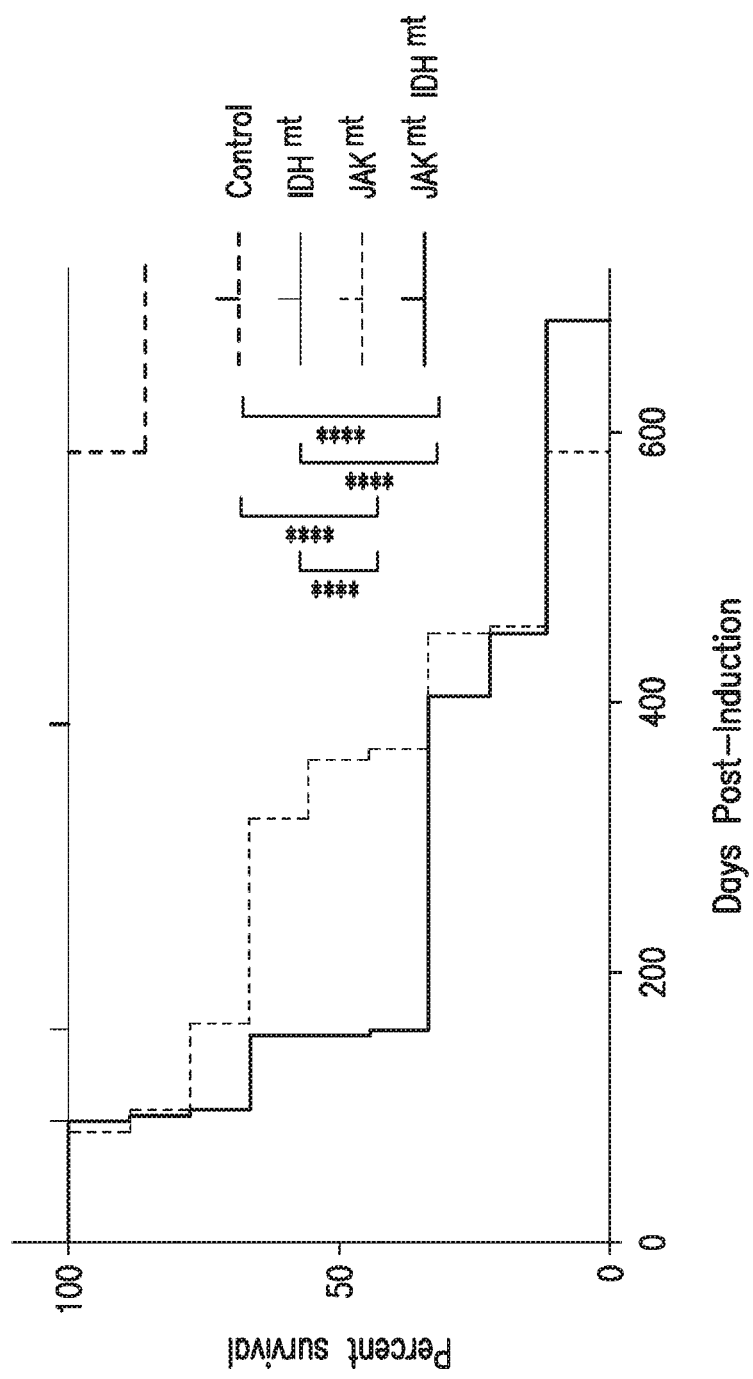
FIGS. 1A-1J demonstrate that combined JAK2/IDH-mutant mice have a lethal myeloproliferative neoplasm with preleukemic features.

The details of construction and the arrangement of components set forth in the following description or illustrated in the drawings are intended to describe non-limiting embodiments. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, "myeloproliferative neoplasms" (MPNs) refers to a group of disorders that cause an overproduction of blood cells (platelets, white blood cells and red blood cells) in the bone marrow. MPNs include polycythemia vera (PV), primary or essential thrombocythemia (ET), primary or idiopathic myelofibrosis, chronic myelogenous (myelocytic) leukemia (CML), chronic neutrophilic leukemia (CNL), juvenile myelomonocytic leukemia (JML) and chronic eosinophilic leukemia (CEL)/hyper eosinophilic syndrome (HES). In certain embodiments, subjects having a high-risk MPN, such as polycythemia vera (PV), primary or essential thrombocythemia (ET), include MPN subjects having a history of thrombosis or subjects over 60 years of age and having a JAK2 mutation. In certain embodiments, subjects having a high-risk myelofibrosis (MF) include MPN subjects having high risk based on dynamic International Prognostic Scoring System (DIPSS). The risk stratification for MPN patients is described by Ayalew Tefferi in American Journal of Hematology, Vol. 91, No. 1, January 2016.

As used herein, the term "wild type" refers to the typical or most common form of a characteristic (for example, gene sequence or presence, or protein sequence, presence, level or activity), as it occurs in nature, and the reference against which all others are compared. As will be understood by one skilled in the art, when used herein, wild type refers to the typical gene sequence(s) or gene expression levels as they most commonly occur in nature.

The term "elevated levels of 2HG" means 10%, 20% 30%, 50%, 75%, 100%, 200%, 500% or more 2HG is present in a subject that carries a mutant IDH2 allele than is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humor, blood (e.g., blood plasma), serum, cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The term "co-administering" as used herein with respect to COMPOUND 1 and a JAK2 inhibitor, for example, ruxolitinib, means that the two compounds may be administered together as part of a single dosage form or as separate, multiple dosage forms. Alternatively, the two compounds may be administered consecutively. In such combination therapy treatment, both the compounds are administered by conventional methods. The administration of a composition comprising both the compounds, to a subject does not preclude the separate administration of the two compounds, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a combination of COMPOUND 1 and a JAK2 inhibitor.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of MPN, characterized by the presence of a mutant allele of IDH2 and a mutant allele of JAK2, lessen the severity of MPN or improve the symptoms associated with MPN.

An amount of a compound, including a pharmaceutically acceptable salt, solvate, tautomer, stereoisomer, isotopologue, prodrug or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, or a polymorph thereof, which is effective, upon single or multiple dose administration to a subject, in treating a cell, or in curing, alleviating, relieving or improving a subject with a disorder beyond that expected in the absence of such treatment.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.*

Vol. 66, pp. 1-19. In one embodiment, the pharmaceutically-acceptable salt is a mesylate salt.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compound 1

In one embodiment, COMPOUND 1 is 2-methyl-1-[(4-[6-(trifluoromethyl)pyridin-2-yl]-6-{[2-(trifluoromethyl)pyridin-4-yl]amino}-1,3,5-triazin-2- yl)amino]propan-2-ol, or a pharmaceutically acceptable salt, solvate, tautomer, stereoisomer, isotopologue, prodrug, metabolite, or a polymorph thereof, having the following formula:

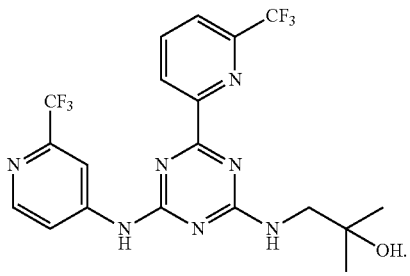 [SMILES: CC(C)(O)CNc1nc(Nc2ccnc(C(F)(F)F)c2)nc(-c2cccc(C(F)(F)F)n2)n1]

COMPOUND 1 may also comprise one or more isotopic substitutions ("Isotopologues"). For example, H may be in any isotopic form, including $^1$H, $^2$H (D or deuterium), and $^3$H (T or tritium); C may be in any isotopic form, including $^{12}$C, $^{13}$C, and $^{14}$C, O may be in any isotopic form, including $^{16}$O and $^{18}$O; and the like. For example, COMPOUND 1 is enriched in a specific isotopic form of H, C and/or O by at least about 60%, 65%, 70%, 75%, 80%, 85%, 90%, 95%, 96%, 97%, 98%, or 99%.

COMPOUND 1 in certain embodiments may also be represented in multiple tautomeric forms, in such instances, one aspect of the invention expressly includes all tautomeric forms of COMPOUND 1 described herein, even though only a single tautomeric form may be represented (e.g., keto-enol tautomers). All such isomeric forms of COMPOUND 1 are expressly included herein. Synthesis of COMPOUND 1 is described in US published application US-2013-0190287-A1 published Jul. 25, 2013, which is incorporated by reference in its entirety.

It may be convenient or desirable to prepare, purify, and/or handle a corresponding salt of COMPOUND 1, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if COMPOUND 1 is anionic, or has a functional group which may be anionic (e.g., —NH— may be —N—'), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4$$^+$.

If COMPOUND 1 is cationic, or has a functional group that may be cationic (e.g., —NHR may be —NH$_2$R$^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. In one embodiment, COMPOUND 1 comprises the mesylate salt of 2-methyl-1-[(4-[4-(trifluoromethyl)pyridin-2-yl]-6-{[2-(trifluoromethyl)pyridin-4-yl]amino}-1,3,5-triazin-2-yl)amino]propan-2-ol (COMPOUND A). Examples of suitable polymeric organic anions include, but are not limited to, those derived from the following polymeric acids: tannic acid, carboxymethyl cellulose.

COMPOUND 1 for use in the methods and pharmaceutical compositions provided herein therefore includes the COMPOUND 1 itself, as well as its pharmaceutically acceptable salts, solvates, tautomers, stereoisomers, isotopologues, prodrugs, metabolites, or polymorphs. Metabolites of COMPOUND 1 are disclosed in patent application publication WO2015/006592, which is incorporated herein by reference in its entirety. COMPOUND 1 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g.,valine) esters), carbamates and other pharmaceutically acceptable derivatives, which, upon administration to a subject, are capable of providing active compounds.

It has been found that COMPOUND 1 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 1. In certain embodiments, the present disclosure provides compositions comprising COMPOUND 1 in a form described herein. In some embodiments of provided compositions, COMPOUND 1 is present as a mixture of one or more solid forms; in some embodiments of provided compositions, COMPOUND 1 is present in a single form.

In one embodiment, COMPOUND 1 is a single crystalline form, or any one of the single crystalline forms described herein. Synthesis of crystalline forms of COMPOUND 1 is described in the international application publication WO 2015/017821 published Feb. 5, 2015 and the international publication WO 2016/126798 published Aug. 11, 2016, both incorporated by reference herein in their entireties. Also provided are pharmaceutical compositions comprising at least one pharmaceutically acceptable carrier or diluent; and COMPOUND 1, wherein COMPOUND 1 is a single crystalline form, or any one of the crystalline forms being described herein. Also provided are uses of COMPOUND 1, wherein COMPOUND 1 is a single crystalline form, or any one of the single crystalline forms described herein, to prepare a pharmaceutical composition.

Compositions Containing COMPOUND 1 and Routes of Administration

In one embodiment, the compounds utilized in the methods provided herein are formulated with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Exemplary formulations of COMPOUND 1 are disclosed in U.S. Provisional Application No. 62/384,643, incorporated herein by reference in its entirety.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as TWEENs or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives may also be advantageously used to enhance delivery of COMPOUND 1 described herein.

In one embodiment, the pharmaceutical composition comprises COMPOUND 1 and an excipient. In one embodiment, the pharmaceutical composition that comprises COMPOUND 1 and an excipient, is for oral administration. In one embodiment, the excipient is a diluent, a binder, a disintegrant, a wetting agent, a stabilizer, a glidant, or a lubricant.

In one embodiment, the diluent is a microcrystalline cellulose.

In one embodiment, the binder is a hydroxypropyl cellulose.

In one embodiment, the disintegrant is sodium starch glycolate.

In one embodiment, the wetting agent is sodium lauryl sulfate.

In one embodiment, the stabilizer is hypromellose acetate succinate.

In one embodiment, the glidant is colloidal silicon dioxide.

In one embodiment, the lubricant is magnesiun stearate.

Oral delivery formats for COMPOUND 1 include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains COMPOUND 1.

Particular embodiments herein provide solid oral dosage forms that are tablets or capsules. In certain embodiments, the formulation is a tablet comprising COMPOUND 1. In certain embodiments, the formulation is a capsule comprising COMPOUND 1. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. Certain embodiments provided herein encompass the use of COMPOUND 1 for the preparation of a pharmaceutical composition for treating a MPN in a subject, wherein the subject harbors a mutant allele of IDH2 and a mutant allele of JAK2, wherein the composition is prepared for oral administration.

Particular embodiments herein provide pharmaceutical formulations (e.g., immediate release oral formulations and/or formulations that release the API substantially in the stomach) comprising COMPOUND 1 that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising COMPOUND 1 that achieve a particular maximum plasma concentration ("Cmax") in the subject to which the formulation is orally administered. Particular embodiments provide oral formulations that achieve a Cmax of COMPOUND 1 of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising COMPOUND 1 that achieve a particular time to maximum plasma concentration ("Tmax") in the subject to which the formulation is orally administered. Particular embodiments provide oral formulations that achieve a Tmax of COMPOUND 1 of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising COMPOUND 1 wherein the oral dosage forms have an enteric coating. Particular embodiments provide a permeable or partly permeable (e.g., "leaky") enteric coating with pores. In particular embodiments, the permeable or partly permeable enteric-coated tablet releases COMPOUND 1 in an immediate release manner substantially in the stomach.

Provided herein are dosage forms designed to maximize the absorption and/or efficacious delivery of COMPOUND 1, upon oral administration, e.g., for release substantially in the stomach. Accordingly, certain embodiments herein provide a solid oral dosage form of COMPOUND 1 using pharmaceutical excipients designed for immediate release of the API upon oral administration, e.g., substantially in the stomach. Particular immediate release formulations comprise a specific amount of COMPOUND 1 and optionally one or more excipients. In certain embodiments, the formulation may be an immediate release tablet or an immediate release capsule (such as, e.g., an HPMC capsule).

Provided herein are methods of making the formulations provided herein comprising COMPOUND 1 provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise COMPOUND 1 in a specific amount. In particular embodiments, the specific amount of COMPOUND 1 in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment, the specific amount is about 140 mg. In one embodiment, the specific amount is about 150 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising COMPOUND 1 alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of COMPOUND 1 and vegetable oil or non-aqueous, water miscible materials such as, for example, polyethylene glycol and the like. In certain embodiments, hard gelatin capsules may be prepared containing granules of COMPOUND 1 in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of COMPOUND 1 is prepared using aqueous solvents without causing significant hydrolytic degradation of the compound. In particular embodiments, the formulation of COMPOUND 1 is a tablet which contains a coating applied to the drug core using aqueous solvents without causing significant hydrolytic degradation of the compound in the formulation. In certain embodiments, water is employed as the solvent for coating the drug core. In certain embodiments, the oral dosage form of COMPOUND 1 is a tablet containing a film coat applied to the drug core using aqueous solvents. In particular embodiments, water is employed as the solvent for film-coating. In particular embodiments, the tablet containing COMPOUND 1 is film-coated using aqueous solvents without effecting degradation of the pharmaceutical composition. In particular embodiments, water is used as the film coating solvent without effecting degradation of the pharmaceutical composition. In certain embodiments, an oral dosage form comprising COMPOUND 1 and an aqueous film coating effects immediate drug release upon oral delivery. In certain embodiments, the oral dosage form comprising COMPOUND 1 and an aqueous film coating effects controlled drug release to the upper gastrointestinal tract, e.g., the stomach, upon oral administration. In particular embodiments, a tablet with an aqueous-based film coating comprises COMPOUND 1 as the API.

In certain embodiments, provided herein is a controlled release pharmaceutical formulation for oral administration of COMPOUND 1, wherein the release occurs substantially in the stomach, comprising: a) a specific amount of COMPOUND 1; b) a drug release controlling component for controlling the release of COMPOUND 1 substantially in the upper gastrointestinal tract, e.g., the stomach; and c) optionally one or more excipients. In certain embodiments, the oral dosage form comprising COMPOUND 1 is prepared as a controlled release tablet or capsule which includes a drug core comprising the pharmaceutical composition and optional excipients. Optionally, a "seal coat" or "shell" is applied. In certain embodiments, a formulation provided herein comprising COMPOUND 1 provided herein is a controlled release tablet or capsule, which comprises a therapeutically effective amount of COMPOUND 1, a drug release controlling component that controls the release of COMPOUND 1 substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of COMPOUND 1 from the polymer matrix substantially in the stomach. In certain embodiments, such formulations may be prepared by incorporating COMPOUND 1 into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045,823); Gusler et al., U.S. Patent Publication No. 2003/0104053 (application Ser. No. 10/029,134), each of which is incorporated herein by reference in its entirety.

In certain embodiments, the drug release controlling component may comprise a shell surrounding the drug-containing core, wherein the shell releases COMPOUND 1 from the core by, e.g., permitting diffusion of COMPOUND 1 from the core and promoting gastric retention of the formulation by swelling upon exposure to gastric fluids to a size that is retained in the stomach. In certain embodiments, such formulations may be prepared by first compressing a mixture of COMPOUND 1 and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain COMPOUND 1 and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, the formulations for use in the methods provided herein are tablets comprising about 20-30% Compound 1; intra-granular excipients comprising about 30-45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 5-50% microcrystalline cellulose, about 2% sodium starch glycolate, about 0.5% colloidal silicon dioxide, and about 0.75% magnesium stearate, all based on total weight of the tablet. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (COMPOUND A). In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (COMPOUND A).

In certain embodiments, the formulations for use in the methods provided herein are tablets comprising about 20-30% Compound 1; intra-granular excipients comprising about 30-45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 9-25% microcrystalline cellulose, about 2% sodium starch glycolate, about 0.5% colloidal silicon dioxide, and about 0.75% magnesium stearate, all based on total weight of the tablet. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In certain embodiments, the formulations for use in the methods provided herein are tablets comprising Compound 1 in an amount from about 20% to about 30%, an intra-granular excipient selected from about 34.5%, 44.5% and to about 39.5% microcrystalline cellulose, about 2% hydroxypropyl cellulose by and 6%, sodium starch glycolate, and an extragranular excipient selected from about 20% microcrystalline cellulose and about 2%, sodium starch glycolate by weight based on total weight of the tablet. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2- ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2- yl)amino]propan-2-ol.

In certain embodiments, the formulations for use in the methods provided herein are tablets comprising about 30% Compound 1; intra-granular excipients comprising about 45% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 9.5% microcrystalline cellulose, about 2% sodium starch glycolate, about 0.5% colloidal silicon dioxide, and about 0.75% magnesium stearate. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2- ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2- yl)amino]propan-2-ol.

In certain embodiments, the formulations for use in the methods provided herein are tablets comprising about 30% Compound 1; intra-granular excipients comprising about 34.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2- ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2- yl)amino]propan-2-ol.

In certain embodiments, the formulations for use in the methods provided herein are tablets comprising about 20% Compound 1; intra-granular excipients comprising about 44.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2- ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2- yl)amino]propan-2-ol.

In certain embodiments, the formulations for use in the methods provided herein are tablets comprising about 25% Compound 1; intra-granular excipients comprising about 39.50% microcrystalline cellulose, about 2% hydroxypropyl cellulose, about 6% sodium starch glycolate, about 1% sodium lauryl sulfate, about 1% hypromellose acetate succinate, about 1.5% colloidal silicon dioxide, and about 0.75% magnesium stearate; and extra-granular excipients comprising about 20% microcrystalline cellulose, about 2% sodium starch glycolate, about 0.5% colloidal silicon dioxide, and about 0.75% magnesium stearate. In one embodiment, Compound 1 is mesylate salt of 2-methyl-1-[(4-[6-(trifluoromethyl)pyridin-2-yl]-6-{[2-(trifluoromethyl)pyridin -4-yl]amino}-1,3,5-triazin-2-yl)amino]propan-2-ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In certain embodiments, the formulations for use in the methods provided herein are tablets comprising Compound 1, colloidal silicon dioxide, hydroxypropyl cellulose, hypromellose acetate succinate, iron oxide yellow, magnesium stearate, microcrystalline cellulose, polyethylene glycol, polyvinyl alcohol, sodium lauryl sulfate, sodium starch glycolate, talc, and titanium dioxide. In one embodiment, Compound 1 is mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. In one embodiment, Compound 1 is polymorph Form 3 of mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

In certain embodiments, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In certain embodiments, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, TWEEN 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs or SPANs and/or other similar emulsifying agents or bioavailability enhancers which are commonly used in the manufacture of pharmaceutically acceptable solid, liquid, or other dosage forms may also be used for the purposes of formulation.

In certain embodiments, the pharmaceutical compositions provided herein may also be administered in the form of suppositories for rectal administration. These compositions can be prepared by mixing COMPOUND 1 with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. In certain embodiments, carriers for topical administration of the compounds provided herein include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In certain embodiments, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In certain embodiments, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

JAK2 Inhibitors

In certain embodiments, the JAK2 inhibitor for use in the methods provided herein is selected from INCB018424 (ruxolitinib), TG101348, CYT387, AZD1480, SB1518 (pacritinib), XL019, NCBO-16562, NVP-BSK805, R723, hydroxycarbamide, SAR302503, CP-690,550 (tasocitinib) and INCB16562.

In one embodiment, the JAK2 inhibitor for use in the methods provided herein is ruxolitinib.

In one embodiment, the JAK2 inhibitor for use in the methods provided herein is TG101348.

In one embodiment, the JAK2 inhibitor for use in the methods provided herein is CYT3 87.

In one embodiment, the JAK2 inhibitor for use in the methods provided herein is AZD1480.

In one embodiment, the JAK2 inhibitor for use in the methods provided herein is SB1518 (pacritinib).

In one embodiment, the JAK2 inhibitor for use in the methods provided herein is XL019.

In one embodiment, the JAK2 inhibitor for use in the methods provided herein is NCBO-16562.

In one embodiment, the JAK2 inhibitor for use in the methods provided herein is NVP-BSK805.

In one embodiment, the JAK2 inhibitor for use in the methods provided herein is R723.

In one embodiment, the JAK2 inhibitor for use in the methods provided herein is hydroxycarbamide.

In one embodiment, the JAK2 inhibitor for use in the methods provided herein is SAR302503.

In one embodiment, the JAK2 inhibitor for use in the methods provided herein is CP-690,550 (tasocitinib).

In one embodiment, the JAK2 inhibitor for use in the methods provided herein is INCB16562.

Pharmaceutical Compositions Containing Ruxolitinib and Routes of Administration

In certain embodiments, provided herein are pharmaceutical compositions comprising ruxolitinib and a pharmaceutically acceptable carrier for administration to a patient in need thereof in the methods provided herein. In certain embodiments, the pharmaceutical composition comprises ruxolitinib and a diluent or solvent. In certain embodiments, the pharmaceutical compositions comprising ruxolitinib are for oral administration.

In certain embodiments, the pharmaceutical composition comprises 5-25 mg ruxolitinib. In certain embodiments, the pharmaceutical composition comprises 5, 10, 15, 20 or 25 mg ruxolitinib.

In certain embodiments, ruxolitinib is administered orally in a dose of about 5-25 mg once or twice a day. In certain embodiments, ruxolitinib is administered orally in a dose of about 5, 10, 15, 20 or 25 mg once or twice a day.

In certain embodiments, ruxolitinib is formulated and administered according to a package insert for ruxolitinib.

In certain embodiments, lower or higher doses of COMPOUND 1 and ruxolitinib than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

COMPOUND 1 can be used in all methods of treatment of MPN or AML in a subject as provided herein It has been observed that JAK2/IDH-mutant MPN is highly sensitive to IDH mutant inhibition and that combined JAK2/IDH-mutant-directed targeted therapy has potent antileukemic effects. It has been further observed that treatment with IDH2 inhibitor COMPOUND 1 shows efficacy in JAK2/IDH2-mutant MPN and AML, including attenuation of myeloid expansion, reversal of stem cell expansion, and reduction in mutant allele burden. In certain embodiments, combination therapy with COMPOUND 1 and a JAK2 inhibitor shows increased efficacy without additive toxicity, with reduced disease burden and reversal of aberrant myeloproliferation in vivo.

In certain embodiments, combination therapy with COMPOUND 1 and ruxolitinib shows increased efficacy without additive toxicity, with reduced disease burden and reversal of aberrant myeloproliferation in vivo.

It has been observed that combination therapy with COMPOUND 1 and ruxolitinib reversed aberrant transcriptional and metabolic abnormalities in JAK2/IDH2-mutant stem/progenitor cells. While not intending to be bound by any particular theory of operation, there may be an interplay between JAK kinase signaling and epigenetic regulation in driving aberrant gene expression in JAK2/IDH2-mutant MPN.

It has been observed that JAK2 inhibition lowered 2HG and altered metabolite levels, raising the possibility that reversing the effect of JAK signaling on metabolism may influence epigenetic regulation of gene expression. This is plausible, as levels of metabolites other than 2HG can influence the methylation status of DNA and histones, including Krebs cycle intermediates (Kaelin et al., Influence of metabolism on epigenetics and disease. *Cell* 2013;153: 56-69) and other metabolic species (Lu et al.,. Metabolic regulation of epigenetics. *Cell metabolism* 2012;16:9-17). While not intending to be bound by any particular theory of operation, combined inhibition of JAK2 and IDH2 may have a greater impact on reversing aberrant metabolism in JAK2/IDH2-mutant cells than could be attributed to inhibition of neomorphic IDH2 function alone.

In certain embodiments, provided herein is a method of treating MPN in a subject comprising administering to the subject a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof (COMPOUND 1) in combination with a therapeutically effective amount of a JAK2 inhibitor, wherein the subject harbors a mutant allele of IDH2 and a mutant allele of JAK2. In one embodiment, the JAK2 inhibitor is ruxolitinib.

In certain embodiments, provided herein is a method of treating a high risk MPN in a subject comprising administering to the subject a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof (COMPOUND 1) in combination with a therapeutically effective amount of a JAK2 inhibitor, wherein the subject harbors a mutant allele of IDH2 and a mutant allele of JAK2. In one embodiment, the JAK2 inhibitor is ruxolitinib.

In certain embodiments, subjects having a high-risk MPN, such as polycythemia vera (PV), primary or essential thrombocythemia (ET), include MPN subjects having a history of thrombosis or subjects over 60 years of age and having a JAK2 mutation. In certain embodiments, subjects having a high-risk myelofibrosis (MF) include MPN subjects having high risk based on dynamic International Prognostic Scoring System (DIPSS). The risk stratification for MPN patients is described by Ayalew Tefferi in *American Journal of Hematology*, Vol. 91, No. 1, January 2016.

In certain embodiments, provided herein is a method of treating AML in a subject comprising administering to the subject a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof (COMPOUND 1) in combination with a therapeutically effective amount of a JAK2 inhibitor, wherein the subject harbors a mutant allele of IDH2 and a mutant allele of JAK2. In one embodiment, the JAK2 inhibitor is ruxolitinib.

In certain embodiments, the mutant allele of IDH2 is mIDH2-R140 or mIDH2-R172.

In certain embodiments, the mutant allele of IDH2 is mIDH2-R140Q. In certain embodiments, the mutant allele of IDH2 is mIDH2-R140W. In certain embodiments, the mutant allele of IDH2 is mIDH2-R140L. In certain embodiments, the mutant allele of IDH2 is mIDH2-R172K. In certain embodiments, the mutant allele of IDH2 is mIDH2-R172G.

In certain embodiments, the mutant allele of JAK2 is mJAK2-V617F.

In certain embodiments, COMPOUND 1 for use in the methods disclosed herein is a mesylate salt (COMPOUND A).

In another aspect, without being bound by theory, certain IDH2 mutations result in a new ability of the enzyme to catalyze the NADPH dependent reduction of α-ketoglutarate to R(−)-2-hydroxyglutarate, in particular R140Q and/or R172K mutations of IDH2. Thus, the compounds, compositions and methods provided herein are useful to treat MPN that is characterized by the presence of a mutant allele of IDH2 imparting such activity and in particular an IDH2 R140Q and/or R172K mutation.

In certain embodiments, the efficacy of the treatment of is monitored by measuring the levels of 2HG in the subject. Typically levels of 2HG are measured prior to treatment, wherein an elevated level is indicated for the use of COMPOUND 1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well known determinations of efficacy of malignancy treatment, such as reduction in number and size of tumors and/or other cancer associated lesions, improvement in the general health of the subject, and alterations in other biomarkers that are associated with malignancy treatment efficacy.

2HG can be detected in a sample by the methods of PCT Publication No. WO 2011/050210 and US Publication No. US2012/0121515 hereby incorporated by reference in their entirety, or by analogous methods. In an exemplary method, 2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50% -95% B (buffers as defined above) over 5 minutes. A Synergi Hydro-RP, 100 mm×2 mm, 2.1 µm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In certain embodiments, 2HG is directly evaluated.

In certain embodiments, a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In certain embodiments a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

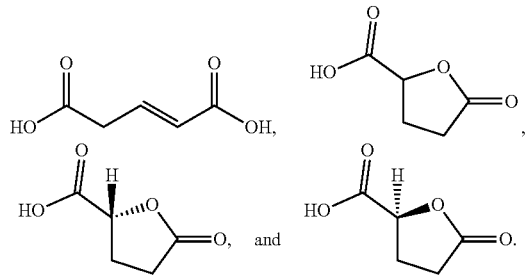

2HG is known to accumulate in the inherited metabolic disorder 2-hydroxyglutaric aciduria. This disease is caused by deficiency in the enzyme 2-hydroxyglutarate dehydrogenase, which converts 2HG to a-KG (Struys, E. A. et al. *Am. J. Hum. Genet.* 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and aKG-dependent prolyl hydroxylases such as those which regulate Hif1-alpha levels.

Treatment methods described herein can additionally comprise various evaluation steps prior to and/or following treatment with COMPOUND 1 and a JAK2 inhibitor, such as ruxolitinib.

In one embodiment, prior to and/or after treatment with COMPOUND 1, the method further comprises the step of evaluating the growth, size, weight, invasiveness, stage and/or other phenotype of MPN.

In certain embodiments, prior to and/or after treatment with COMPOUND 1 and a JAK2 inhibitor, such as ruxolitinib, the method further comprises the step of evaluating the IDH2 genotype of MPN. This may be achieved by ordinary methods in the art, such as DNA sequencing, immuno analysis, and/or evaluation of the presence, distribution or level of 2HG.

In one embodiment, prior to and/or after treatment with COMPOUND 1 and a JAK2 inhibitor, such as ruxolitinib, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In certain embodiments, depending on the disease to be treated and the subject's condition, COMPOUND 1 may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. COMPOUND 1 may be formulated alone or together with one or more active agent(s), in suitable dosage unit with pharmaceutically acceptable excipients, carriers, adjuvants and vehicles, appropriate for each route of administration.

In certain embodiments, the amount of COMPOUND 1 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 60 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 60 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In certain embodiments, COMPOUND 1 for methods described herein is administered at a dose of about 20 to 2000 mg/day. In certain embodiments, COMPOUND 1 is administered at a dose of about 50 to 500 mg/day. In certain embodiments, the dose is about 60 mg/day. In certain embodiments, the dose is about 100 mg/day. In certain embodiments, the dose is about 150 mg/day. In certain embodiments, the dose is about 200 mg/day. In certain embodiments, the dose is about 300 mg/day.

In one embodiment, the amount of COMPOUND 1 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 30 mg. In one embodiment, the particular amount is about 50 mg. In one embodiment, the particular amount is about 60 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 650 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 60 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 1 can be delivered as a single dose such as, e.g., a single bolus injection, or oral tablets or pills; or over time such as, e.g., continuous infusion over time or divided bolus doses over time. In one embodiment, COMPOUND 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 1 for methods described herein is administered once daily.

In certain embodiments, COMPOUND 1 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 1 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In certain embodiments, COMPOUND 1 for methods described herein is administered for 1 to 25 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 1 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In certain embodiments, COMPOUND 1 is administered in one or more 28 day cycles in the methods described herein. In certain embodiments, COMPOUND 1 is administered in a 28 day cycle in the methods described herein.

In certain embodiments, COMPOUND 1 is administered orally in the methods described herein.

In certain embodiments, COMPOUND 1 is administered once daily orally in 28-day cycles at the dose of about 100 mg/day in the methods described herein.

In a particular embodiment, COMPOUND 1 is for use in a method for treating a MPN or AML in a subject, wherein the method comprises orally administering to the subject a therapeutically effective amount of an IDH2 inhibitor in combination with a therapeutically effective amount of a JAK2 inhibitor, wherein the subject harbors a mutant allele of IDH2 and a mutant allele of JAK2, wherein COMPOUND 1 is administered once daily in 28-day cycles at a dose of 5, 10, 25, 50, 100, 150 or 200 mg, or at a dose of 100 mg/day.

In one embodiment, provided herein is a method of identifying a subject suitable for methods of treatment described herein, comprising: (a) obtaining a biological sample from a subject having MPN; (b) screening the biological sample for an IDH2 mutation and a mutation of a JAK2; and (c) if the subject is characterized by the presence of a mutant allele of IDH2 and the presence of a mutant allele of JAK2, identifying the subject as a subject suitable for treatment using the methods described herein. In another embodiment, the subjects identified as subjects suitable for methods of treatment described herein are treated with a combination of COMPOUND 1 and a JAK2 inhibitor, such as ruxolitinib.

In one embodiment, provided herein is a method of identifying a subject suitable for methods of treatment described herein, comprising: (a) obtaining a biological sample from a subject having AML; (b) screening the biological sample for an IDH2 mutation and a mutation of a JAK2; and (c) if the subject is characterized by the presence of a mutant allele of IDH2 and the presence of a mutant allele of JAK2, identifying the subject as a subject suitable for treatment using the methods described herein.

In another embodiment, the subjects identified as subjects suitable for methods of treatment described herein are treated with a combination of COMPOUND 1 and a JAK2 inhibitor, such as ruxolitinib.

In certain embodiment, the inhibitory activity of COMPOUND 1 against IDH2 mutants can be tested by methods described in US Publication No. US 2013/0190287, hereby incorporated by reference in their entireties, or analogous methods.

Patient Population

In certain embodiments of the methods provided herein, the subject to be treated is an animal, for example a mammal or a non-human primate. In particular embodiments, the subject is a human patient. The subject can be male or female.

Particularly, subjects amenable to treatment according to the methods provided herein include subjects with MPN or AML, wherein the subject harbors a mutant allele of IDH2 and a mutant allele of JAK2.

Also encompassed are methods of treating a subject regardless of the subject's age, although some diseases or disorders are more common in certain age groups. In some embodiments, the subject is a human patient at least 18 years old. In some embodiments, the patient is 10, 15, 18, 21, 24, 35, 40, 45, 50, 55, 60, 65, 70, 75, 80, or 85 years old or older. In some embodiments, the subject is a human patient 60 years old or older.

In certain embodiments, subjects amenable to treatment according to the methods provided herein include subjects with high-risk MPN, including subjects having a history of thrombosis or subjects over 60 years of age and having a JAK2 mutation. In certain embodiments, subjects having a high-risk myelofibrosis (MF) include MPN subjects having high risk based on dynamic International Prognostic Scoring System (DIPSS).

In certain embodiments, the methods provided herein encompass the treatment of subjects who have not been previously treated for MPN. In other embodiments, the methods encompass treating subjects who have been previously treated but are non-responsive to standard therapies as well as those who are currently being treated for MPN. For example, the subjects may have been previously treated or are currently being treated with a standard treatment regimen for MPN known to the practitioner of skill in the art.

In certain embodiments, the methods provided herein encompass the treatment of subjects who have not been previously treated for AML. In other embodiments, the methods encompass treating subjects who have been previously treated but are non-responsive to standard therapies as well as those who are currently being treated for AML. For example, the subjects may have been previously treated or are currently being treated with a standard treatment regimen for AML known to the practitioner of skill in the art.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

EXAMPLES

As used, the symbols and conventions used in the examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: MDS=myelodysplastic syndrome; ASXL1=Additional Sex Combs Like 1; BRAF=B-Raf Proto-Oncogene, Serine/Threonine Kinase; CBL=Casitas B-Lineage Lymphoma Proto-Oncogene; CSF3R=Colony Stimulating Factor 3 Receptor; DNMT3A=DNA Cytosine-5-Methyltransferase 3 Alpha; FAT3=FAT Atypical Cadherin 3; JAK2=Janus kinase 2; KRAS=Kirsten rat sarcoma viral oncogene homolog; mIDH2=mutant isocitrate dehydrogenase 2; MPL=Myeloproliferative Leukemia Protein; NRAS=Neuroblastoma RAS Viral Oncogene Homolog; SETBP1=SET Binding Protein 1; SRSF2=Serine/Arginine-Rich Splicing Factor 2; STAG2=Stromal Antigen 2; TCF=Transcription Factor 3; TP53=tumor protein p53; U2AF1=U2 Small Nuclear RNA Auxiliary Factor 1; CR=complete response; HI=Hematological Improvement; mCR=marrow complete response; NR=No Response; and PR=partial response.

Transgenic Animals and Assays

Transgenic Animals

The conditional $JAK2^{V617F}$ mice used in the study are described in Mullally et al. Physiological JAK2V617F expression causes a lethal myeloproliferative neoplasm with differential effects on hematopoietic stem and progenitor cells, *Cancer Cell*, 2010;17:584-96. Conditional transgenic $IDH1^{R132H}$ mice were provided by Kwok-Kin Wong (Dana Farber Cancer Institute) and the conditional $IDH2^{R140Q}$ mice were provided by Craig B. Thompson (Memorial Sloan Kettering Cancer Center).

At induction, mice received five intraperitoneal injections of polyI:polyC (Amersham) of 200 μl of a 1 mg per ml solution. Peripheral blood was collected via cheek bleeding using heparinized microhematocrit capillary tubes (Thermo Fisher Scientific). Peripheral blood counts were obtained using a HemaVet according to standard manufacturer's instructions. Excision at two weeks post-induction was confirmed using PCR. All animal procedures were conducted in accordance with the Guidelines for the Care and Use of Laboratory Animals.

Histology

Pathology was obtained after fixation in 4% paraformaldehyde (PFA); blood smears and bone marrow cytospins were performed on the day of sacrifice. Sections were stained with hematoxylin and eosin stain or Wright Giemsa stain as appropriate. CD34+ staining was performed using CD34, Rat Monoclonal Antibody Performed on a Leica Bond™ RX using the Bond™ Polymer Refine Detection Kit (Cat. No. DS9800). The sections stained with CD34 (Abcam, Cat. Ab8158 diluted 1:50) were pre-treated using heat mediated antigen retrieval with Citrate, pH6 (Leica Biosystem Epitope Retrieval 1, Cat. No. AR9961) for 20 min. DAB was used as the chromogen, counterstained with hematoxylin and mounted.

Bone Marrow Transplant Studies

Dissected femurs and tibias were isolated. Bone marrow was flushed into PBS+2% BSA or RPMI+10% FCS using a syringe or by centrifuge spin. Spleens were isolated and single cell suspensions made by mechanical disruption using glass slides. All harvested cells were passed through a 70 mm strainer. Red blood cells (RBCs) were lysed in ammonium chloride-potassium bicarbonate lysis buffer for 10 min on ice. Cells were transplanted by via tail vein injection into lethally irradiated (2×550 Rad) CD45.1 host mice. For noncompetitive transplants, 1×10$^6$ total cells were transplanted; for competitive transplants including drug studies, 1×10$^6$ total donor cells were injected in a mixture with 1×10$^6$ cells from a congenic CD45.1 donor; for cell of origin transplants, injection number was determined based on the lowest yield after sort to inject approximately 100,000 MPP or 300 LT-HSC with 300,000 whole bone marrow cells from a CD45.1 donor.

Therapeutic Assays

Approximately two months after competitive transplant, peripheral blood analysis was performed by HemaVet and FACS for donor chimerism. Mice were matched using HCT(%), WBC(K/uL), Donor chimerism, and body weight, and they were randomized within matching groups using a random number generator. Drugs were administered BID by gavage for 21-28 days, except where otherwise indicated. Ruxolitinib (James Bradner, Dana Farber Cancer Institute) was administered 60 mg per kg; 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (AG221) was administered at 100 mg per kg or 40 mg per kg. Final doses were administered approximately 1.5 hours before sacrifice.

Flow Cytometry and Fluorescence-Activated Cell Sorting for Murine Tissues

Cells were stained with antibodies in FACS Buffer (2% Bovine Serum Albumin in phosphate-buffered saline (PBS)) for 30 min on ice. Donor and support chimerism was assessed using antibodies against CD45.1 (Clone A20, Biolegend) and CD45.2 (Clone 104, BioLegend).

For hematopoietic stem and progenitor staining, cells were stained with a lineage cocktail including CD4 (clone RM4-5, BioLegend), CD3 (clone 17A2, BioLegend), B220/CD45R (clone RA3-6B2, BioLegend), NK1.1 (clone PK136, BioLegend), Gr-1 (clone RB6-8C5, BioLegend), Mac1/CD11b (clone M1/70, BioLegend) and Ter119 (cat no. 116223, BioLegend), allowing for mature lineage exclusion from the analysis. Cells were also stained with antibodies specific to c-Kit/CD117 (clone 2B8, BioLegend), Sca-1 (clone D7, BioLegend), FcγRII/III/CD16/32 (clone 2.4G2, eBiosciences) and CD34 (clone RAM34, eBiosciences) or SLAM/CD150 (TC15-12F12.2, BioLegend) and CD48 (HM48-1, eBioscience). To assess mature cell lineages we used a combination of antibodies against Mac1, Gr-1, B220, CD3, cKit/CD117, CD45.1, and CD45.2.

To assess erythroid and megakaryocyte progenitors we stained unlysed tissues with a lineage cocktail including CD4, CD8, B220/CD45R, Mac1/CD11b, Gr-1, IL7R/CD127 (A7R34, BioLegend), CD49b (DX5, BioLegend). Antibodies were also used against c-Kit/CD117, Sca-1, SLAM/CD150, CD48, FcγRII/III/CD16/32, CD41 (eBioMWReg30, eBioscience), CD105 (MJ7/18, BioLegend), CD71 (RI7217, BioLegend), and Ter119 and gated as described by Pronk et al., Elucidation of the Phenotypic, Functional, and Molecular Topography of a Myeloerythroid Progenitor Cell Hierarchy, *Cell Stem Cell* 2007;1:428-42.

Before cell of origin transplants, sorting was performed on bone marrow with enrichment for cKit/CD117-positive cells using CD117 MicroBeads (Miltenyi). For expression analysis, sorting was performed on bone marrow that had been depleted of mature cells using Progenitor Cell Enrichment Kit (STEMCELL Technologies).

Metabolomic Analysis

2HG was extracted from serum using 80% aqueous methanol, as described by Lu et al., Expression of a homodimeric type I cytokine receptor is required for JAK2V617F-mediated transformation. *Proceedings of the National Academy of Sciences of the United States of America* 2005;102:18962-7. All extracts were spun at 13,000 rpm at 4° C. to remove precipitate, dried at room temperature, and stored at −80° C. Metabolite levels were determined by ion-paired reverse-phase LC coupled to negative mode electrospray triple-quadrupole mass spectrometry using multiple reactions monitoring, and integrated elution peaks were compared with metabolite standard curves for absolute quantification Dang et al, Cancer-associated IDH1 mutations produce 2-hydroxyglutarate *Nature* 2009;462:739-44.

Polar metabolites were extracted from flash-frozen bone marrow aspirates using 5:3:5 ice cold methanol:water:chloroform on ice. Extracts were vortexed for 10 min at 4° C. and then centrifuged for 5 min at 4° C. at max speed on a tabletop centrifuge. Equal volumes of the aqueous phase from each sample were removed and dried under nitrogen gas.

Central Metabolite Profiling and Isotope Tracing LC/MS analyses were conducted on a QExactive benchtop orbitrap mass spectrometer equipped with an Ion Max source and a HESI II probe, which was coupled to a Dionex UltiMate 3000 UPLC system (Thermo Fisher Scientific, San Jose, Calif.). External mass calibration was performed using the standard calibration mixture every 7 days. 1 uL of each sample was injected onto a ZIC-pHILIC 2.1 3 150 mm (5 mm particle size) column (EMD Millipore). Buffer A was 20 mM ammonium carbonate, 0.1% ammonium hydroxide; buffer B was acetonitrile. The chromatographic gradient was run at a flow rate of 0.150 ml/min as follows: 0-20 min.: linear gradient from 80% to 20% B; 20-20.5 min.: linear gradient from 20% to 80% B; 20.5-28 min.: hold at 80% B. The mass spectrometer was operated in full-scan, polarity switching mode with the spray voltage set to 3.0 kV, the heated capillary held at 275 C, and the HESI probe held at 350 C. The sheath gas flow was set to 40 units, the auxiliary gas flow was set to 15 units, and the sweep gas flow was set to 1 unit. The MS data acquisition was performed in a range of 70-1000 m/z, with the resolution set at 70,000, the AGC target at 10e6 , and the maximum injection time at 20 msec. Relative quantitation of polar metabolites was performed with XCalibur QuanBrowser 2.2 (Thermo Fisher Scientific) using a 5 ppm mass tolerance and referencing an in-house library of chemical standards.

Expression Analysis

CD45.2+ LSK cells were sorted into ice cold FACS Buffer, pelleted, and stored in Triazol until extraction of RNA using phenol-chloroform. The library was produced using SMARTer amplification (Clontech) amplify and create the library. Illumina sequencing was performed using Paired-End 50 bp at 40×10$^6$ reads per sample.

Human Tissues

Approval was obtained from the Institutional Review Board at Memorial Sloan-Kettering Cancer Center. Tissues were collected in partnership with the Human Oncology Tissue Bank, and all patients provided informed consent. Fresh peripheral blood was collected into heparinized collection tubes, and separation of peripheral blood mononuclear cells (PBMC) was performed using hetastarch and a Ficoll gradient with subsequent red blood cell lysis.

Human Colony Forming Assays

Frozen or fresh PBMCs were plated in Methocult H4435 (Stem Cell) with penicillin and streptomycin in triplicate wells. MPN patient cells were plated after enrichment using CD34 Microbeads (Miltenyi) at 1,000 cells per well; AML patient cells were plated without enrichment at 100,000 cells per well. AG221 and ruxolitinib were dissolved into samples at 400 nM concentration and DMSO was dissolved into controls.

Flow Cytometry for Human Tissues

To observe erythroid differentiation in human tissues we stained with a combinationf of CD117/cKit (YB5.B8, eBiosciences), CD34 (581, BioLegend), CD38 (HIT2, BioLegend), CD36 (5-271, BioLegend), CD71 (OKT9, eBioscience), and CD235a (HIR2, eBioscience). To observe monocytic and granulocytic differentiation, antibodies against CD117/cKit, CD34, CD38, CD15 (HI98, eBioscience), CD14 (HCD14, BioLegend), and CD16 (3G8, BioLegend) were used.

Statistical Analysis

Data are displayed as mean±SEM. Prism software was used to conduct the statistical analysis of all data. Multiple comparisons were performed using an ordinary one-way ANOVA, using Tukey's correction for post-hoc comparisons and multiplicity-corrected p-values. Comparisons of survival were performed using the log-rank (Mantel-Cox) test. Statistical interaction calculated for influence of JAK2 mutation status and IDH1 mutation status combined using two-way ANOVA. Paried t-tests were used to compare results in mice before and after treatment. P<0.05 was considered to be significant. *P<0.05, P<0.01, *P<0.001, ****P<0.0001.

Example 1

Figure 1B:
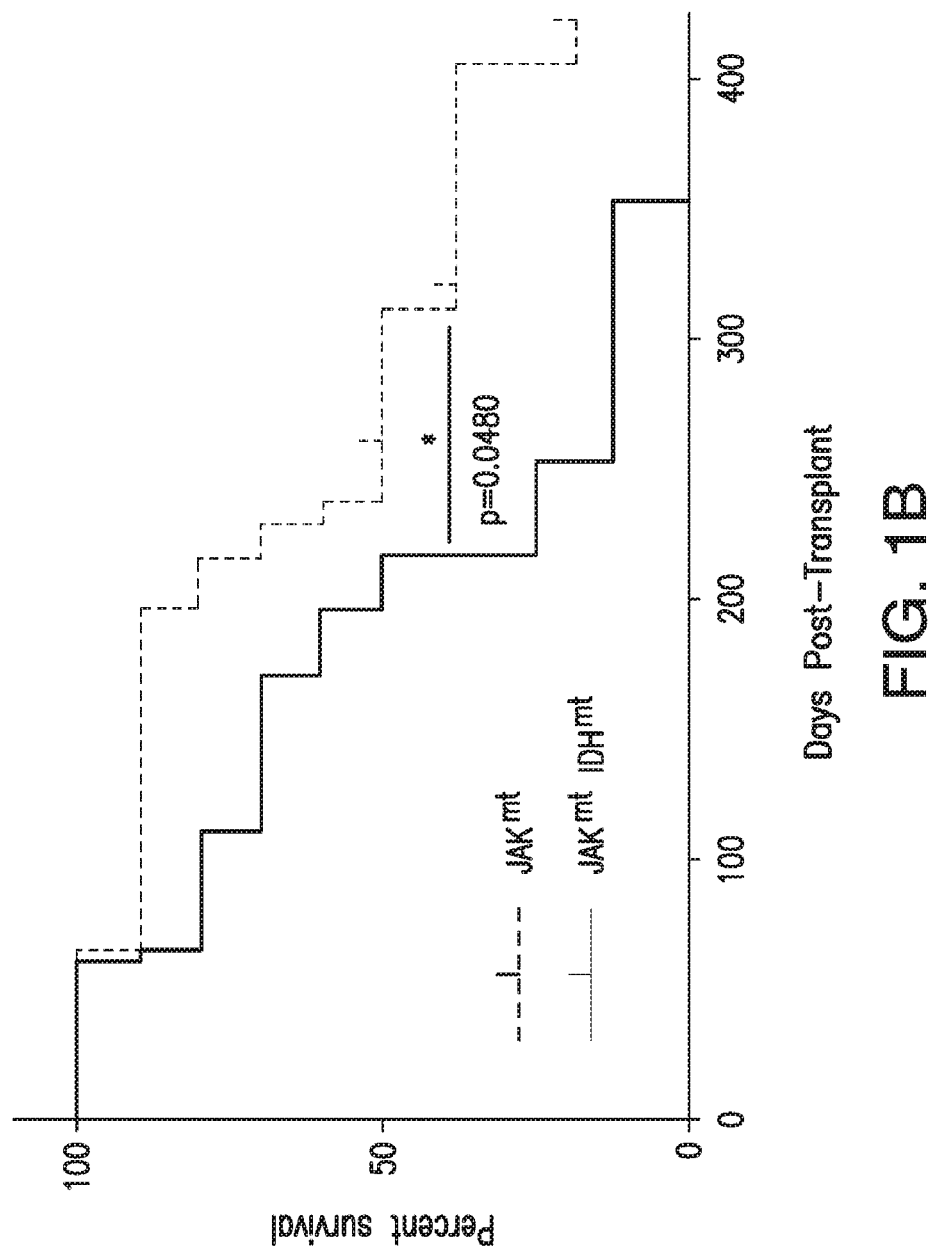
Figure 1C:
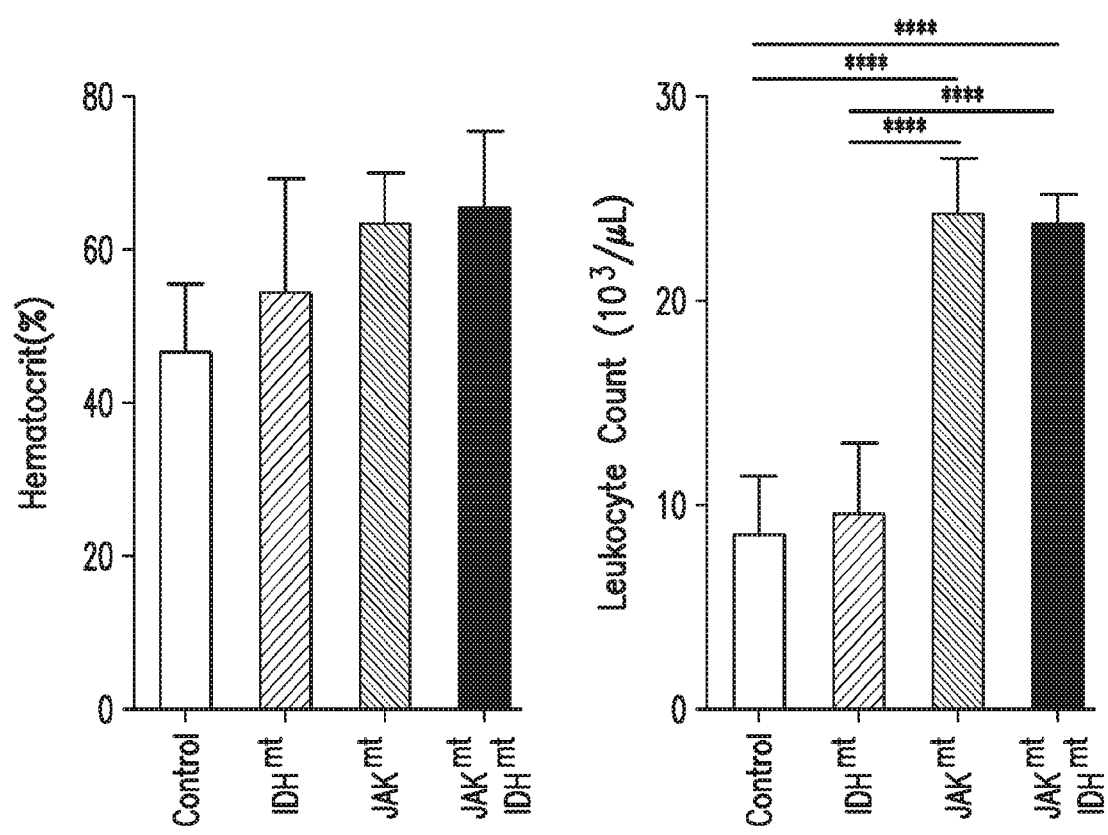
Figure 1D:
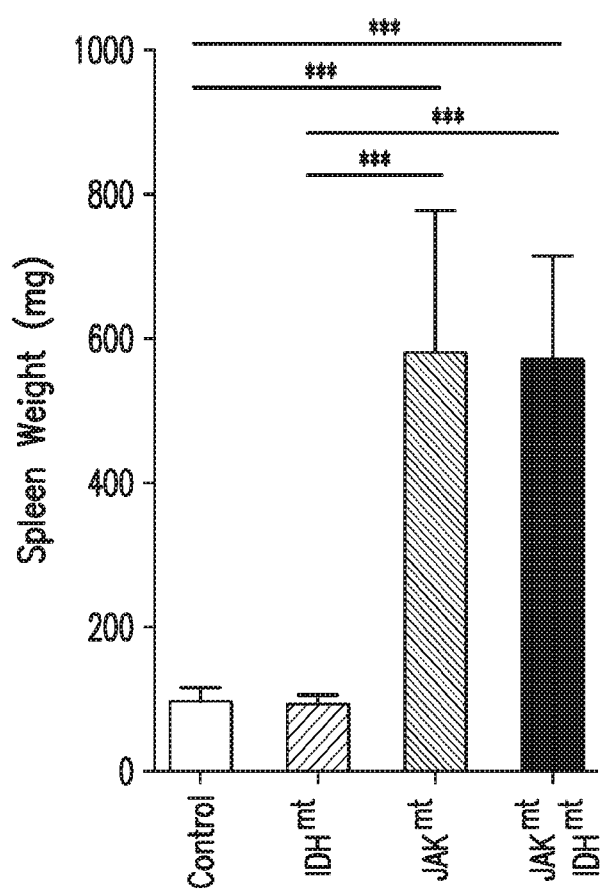
Figure 1E:
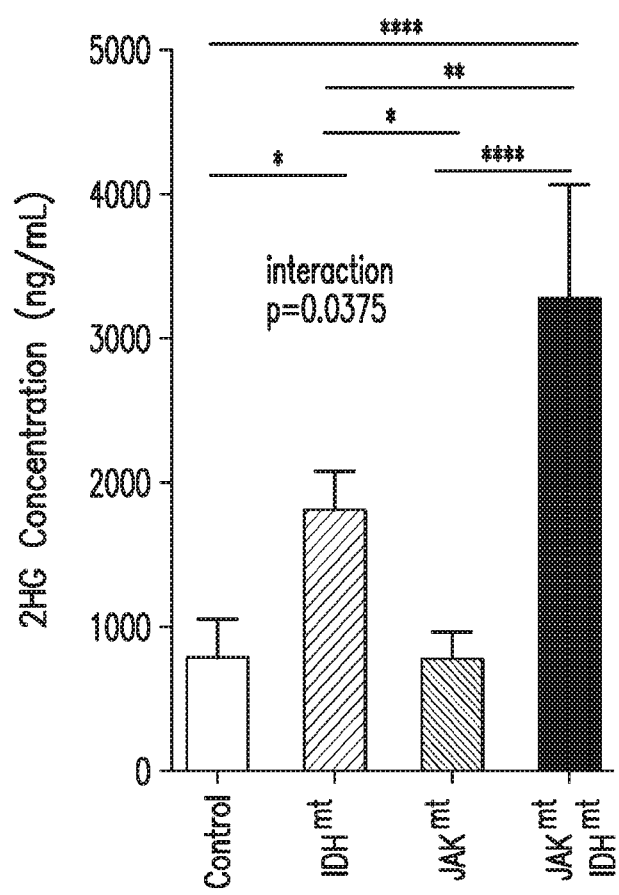
Figure 1F:
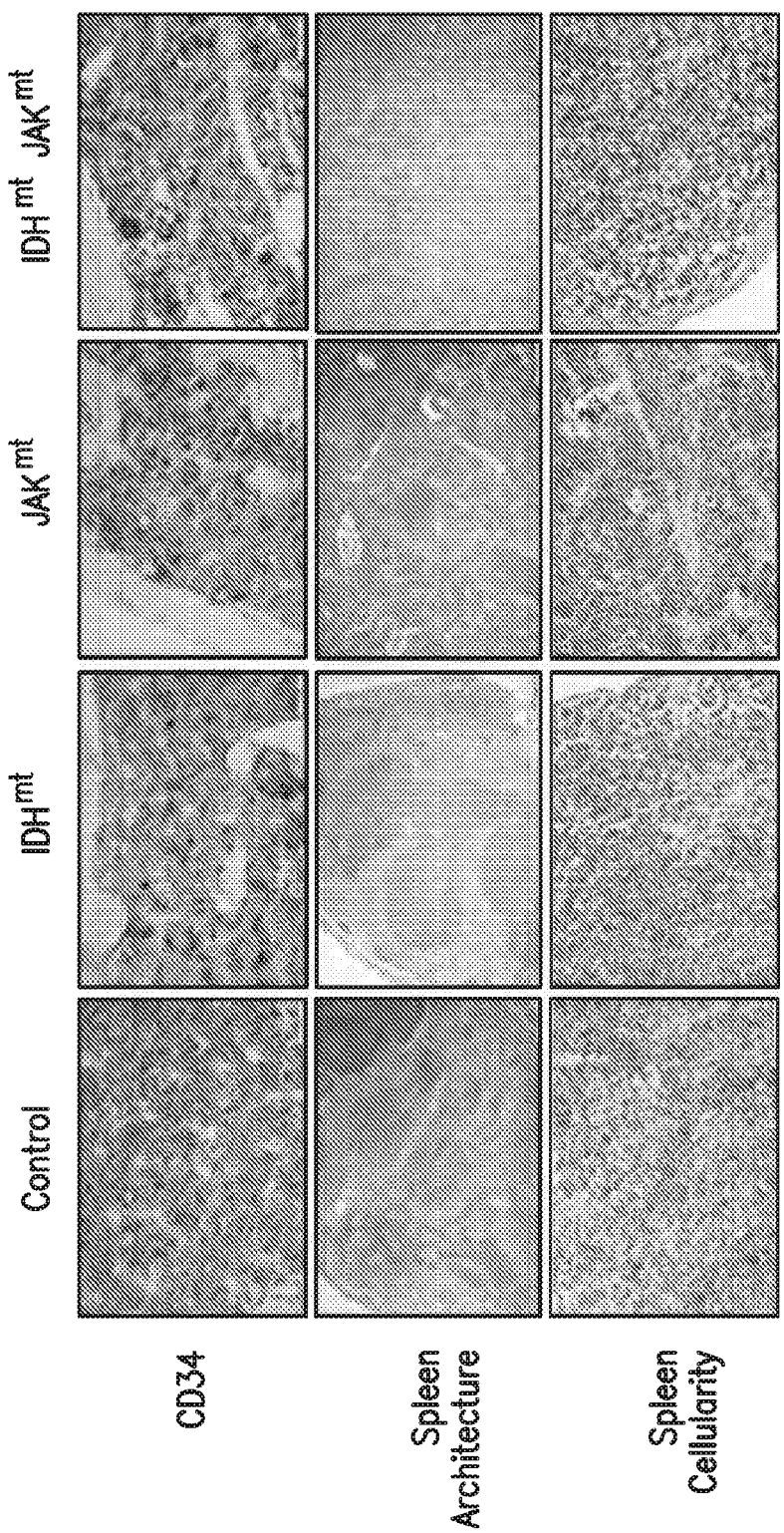
Figure 1G:
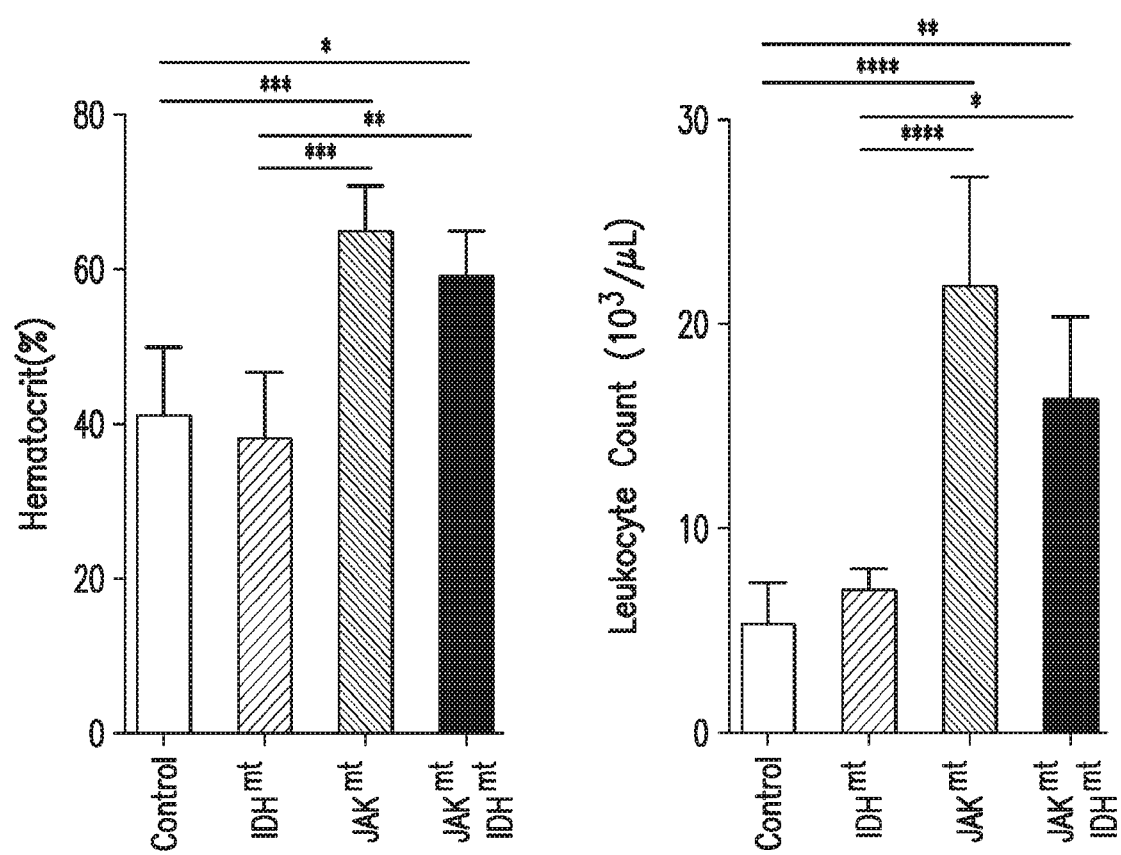
Figure 1H:
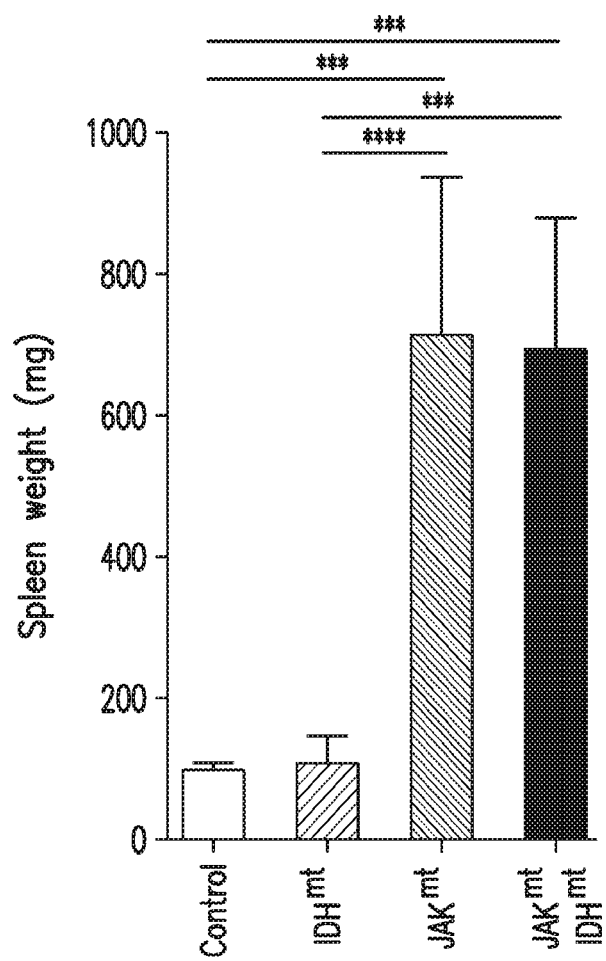
Figure 1I:
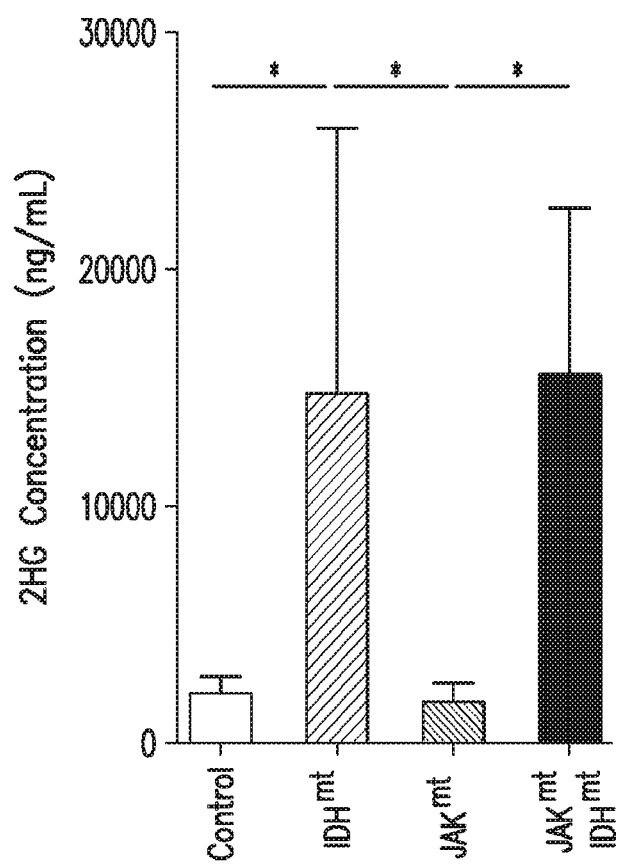
Figure 1J:
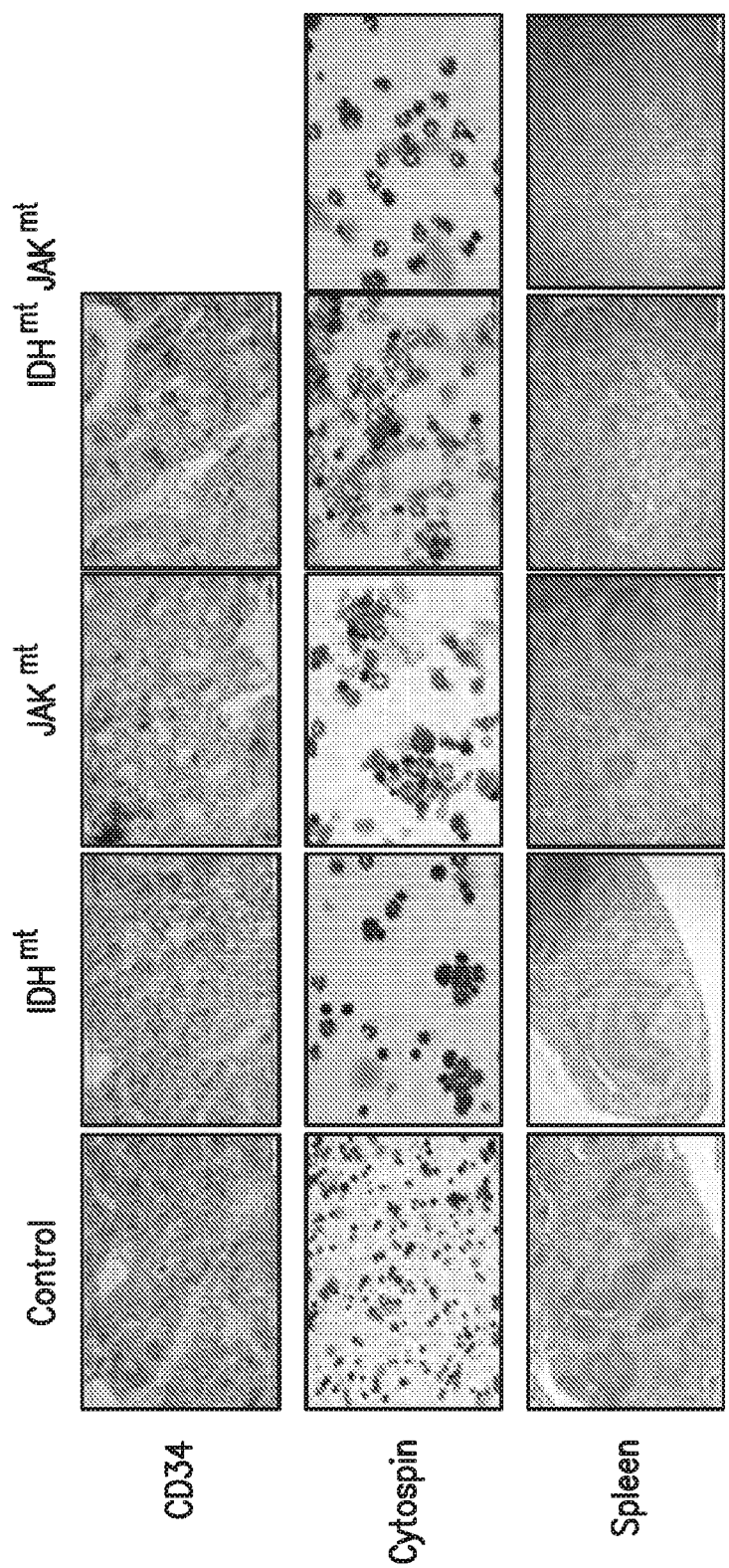

JAK2$^{V617F}$ and Neomorphic IDH1/IDH2 Mutations Cooperate In Vivo to Drive Progressive MPN In order to assess whether IDH and JAK2 mutations cooperate to transform hematopoietic stem/progenitor cells, mice with conditional IDH1$^{R132H}$ or IDH2$^{R140Q}$ alleles were crossed with a JAK2$^{V617F}$ allele described in Mullally et al., Physiological JAK2V617F expression causes a lethal myeloproliferative neoplasm with differential effects on hematopoietic stem and progenitor cells, *Cancer Cell* 2010; 17:584-96, and then used the inducible Mx1-cre allele (Kuhn et al., *Science*. 1995 Sep. 8;269 (5229):1427-9) to induce expression of these alleles in hematopoietic cells. Expression of IDH1$^{R132H}$ or IDH2$^{R140Q}$ in concert with JAK2$^{V617F}$ resulted in a fully penetrant, lethal disease similar in overall survival to JAK2$^{V617F}$ alone (median survival 156 and 359 days, respectively), but with reduced survival compared to IDH1$^{R132H}$ or IDH2$^{R140Q}$ mutant or wild type mice (median survival undefined in 800 days; p<0.0001; FIG. 1A). In contrast, in transplantation studies mice transplanted with IDH/JAK2 mutant cells showed significantly reduced survival in comparison to recipients transplanted with JAK2 mutant cells (median survival 206 and 274 days, respectively; p=0.0480; FIG. 1B). In timed sacrifices, mice with combined of IDH1$^{R132H}$ or IDH2$^{R140Q}$ with JAK2$^{V617F}$ mutation show polycythemia (mean hematocrit 59%, 65% respectively), leukocytosis (mean 23.78 K/uL, 16.22 K/uL respectively; FIG. 1C, G) and splenomegaly (574.4 mg, 690.7 mg, respectively; FIG. 1D, H) similar to JAK2 mutant controls. IDH1$^{R132H}$ and IDH2$^{R140Q}$ mice had elevated levels of 2HG in serum (FIG. 1E, I), and 2HG levels were higher in mice with concurrent IDH1$^{R132H}$ and JAK2$^{V617F}$ compared to mice with IDH1$^{R132H}$ alone (p=0.0024) suggesting JAK2 and IDH1 mutations interact to promote higher 2HG levels (p=0.0375; FIG. 1E). Expression of mutant IDH 1 or IDH2 in concert with JAK2$^{V617F}$ resulted in disruption of splenic architecture beyond that observed in JAK2$^{V617F}$ mice, including expansion of blast-like cells with open chromatin and large nucleoli in IDH/JAK2 mutant mice not seen in JAK2$^{V617F}$ mice. JAK2/IDH mutant megakaryocytes had increased expression of CD34 by immunohistochemistry compared to platelet progenitors in JAK2$^{V617F}$ mice consistent with impaired megakaryocytic differentiation (FIG. 1F, J).

These data indicate that concurrent JAK2 and IDH1/2 mutations cooperate to drive a lethal, transplantable myeloproliferative neoplasm with impaired differentiation in vivo not seen with expression of either allele alone.

Example 2

Figure 2A:
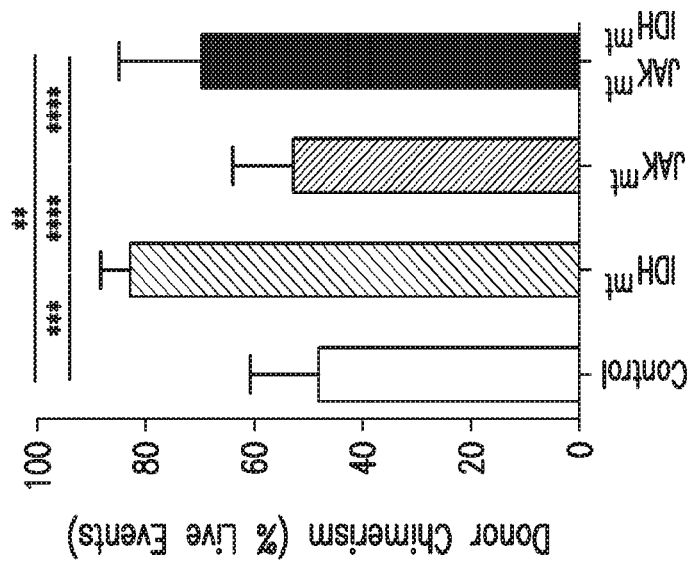
FIGS. 2A-2G demonstrate that combined mutant mice have expanded pathological stem and progenitor populations.
Figure 2A:
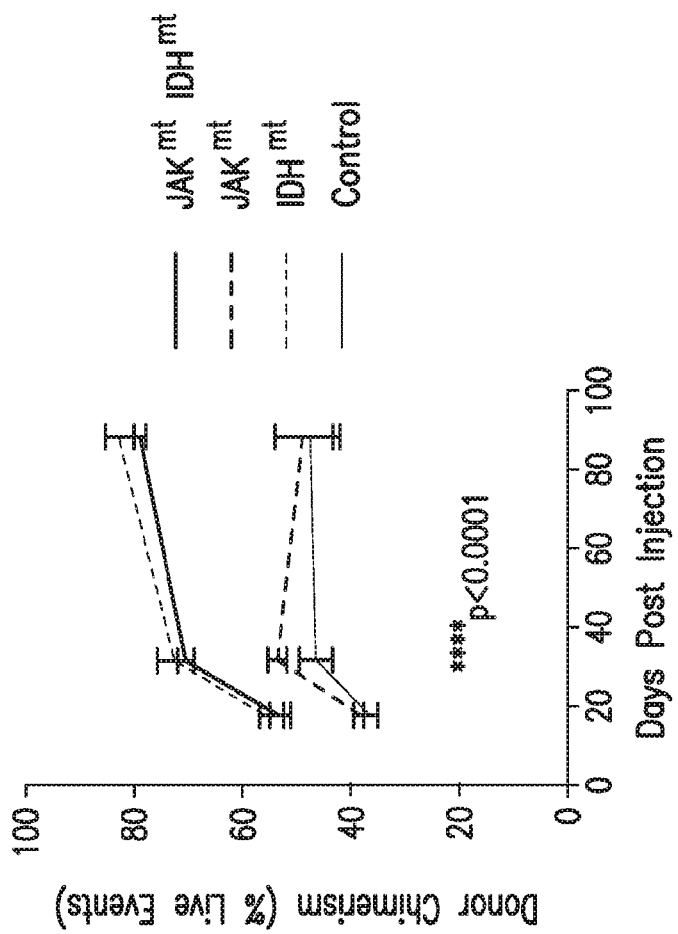
Figure 6A:
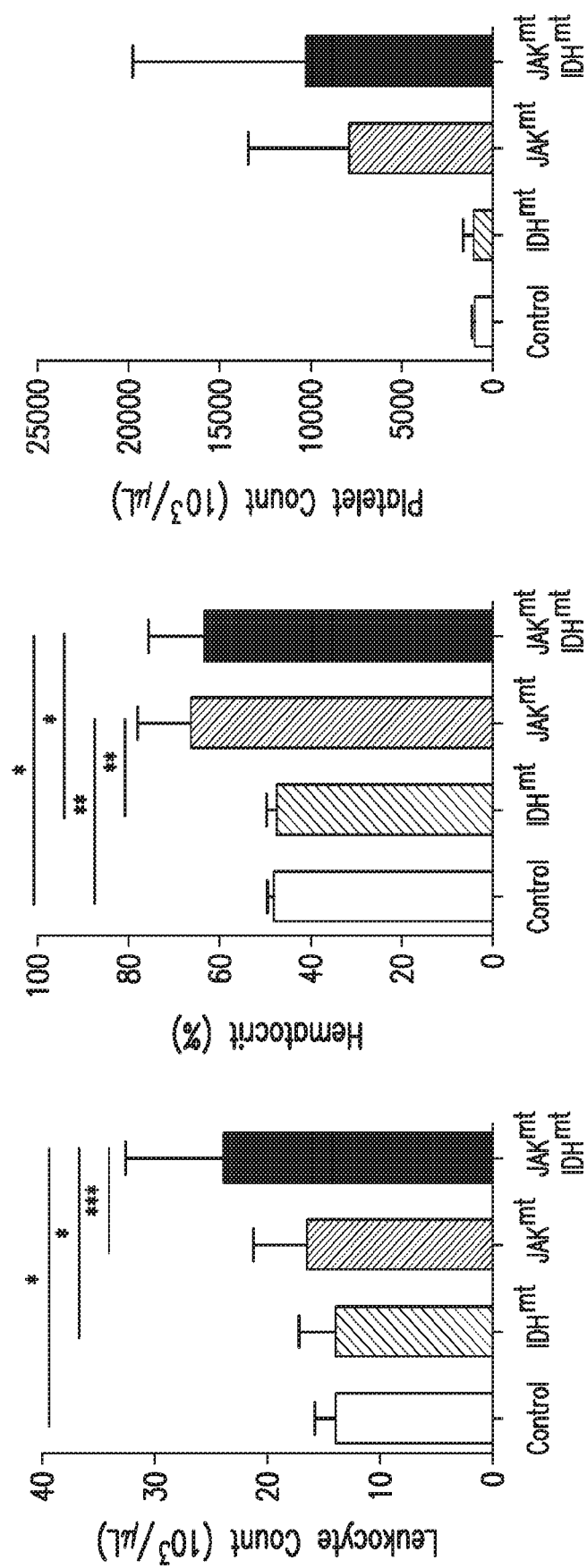

JAK2/IDH-mutant MPN Initiates and Propagates Disease from the Long-term Hematopoietic Stem Cell Compartment In competitive transplants, it was found that IDH2$^{R140Q}$ mutant bone marrow cells were able to out-compete wild type cells, and the resultant increase in self-renewal induced by mutant IDH2 was maintained in cells with concurrent IDH2$^{R140Q}$ and JAK2$^{V617F}$ mutations (FIG. 2A). Transplant recipients had a phenotype similar to primary mice including polycythemia and thrombocytosis. In mice engrafted with IDH2$^{R140Q}$ JAK2$^{V617F}$ marrow were found to have greater leukocytosis in comparison to mice transplanted with JAK2$^{V617F}$ mutant cells (FIG. 6A).

Since hematopoietic malignancies induced by mutant IDH and JAK2 propagate through cells derived from different stem cell compartments, see, Shih et al. Mutational cooperativity linked to combinatorial epigenetic gain of function in acute myeloid leukemia, *Cancer Cell* 2015; 27:502-15; and Kats et al. Proto-oncogenic role of mutant IDH2 in leukemia initiation and maintenance, *Cell Stem Cell* 2014;14:329-41; the cell population that could propagate JAK2/IDH-mutant disease were explored.

Figure 2B:
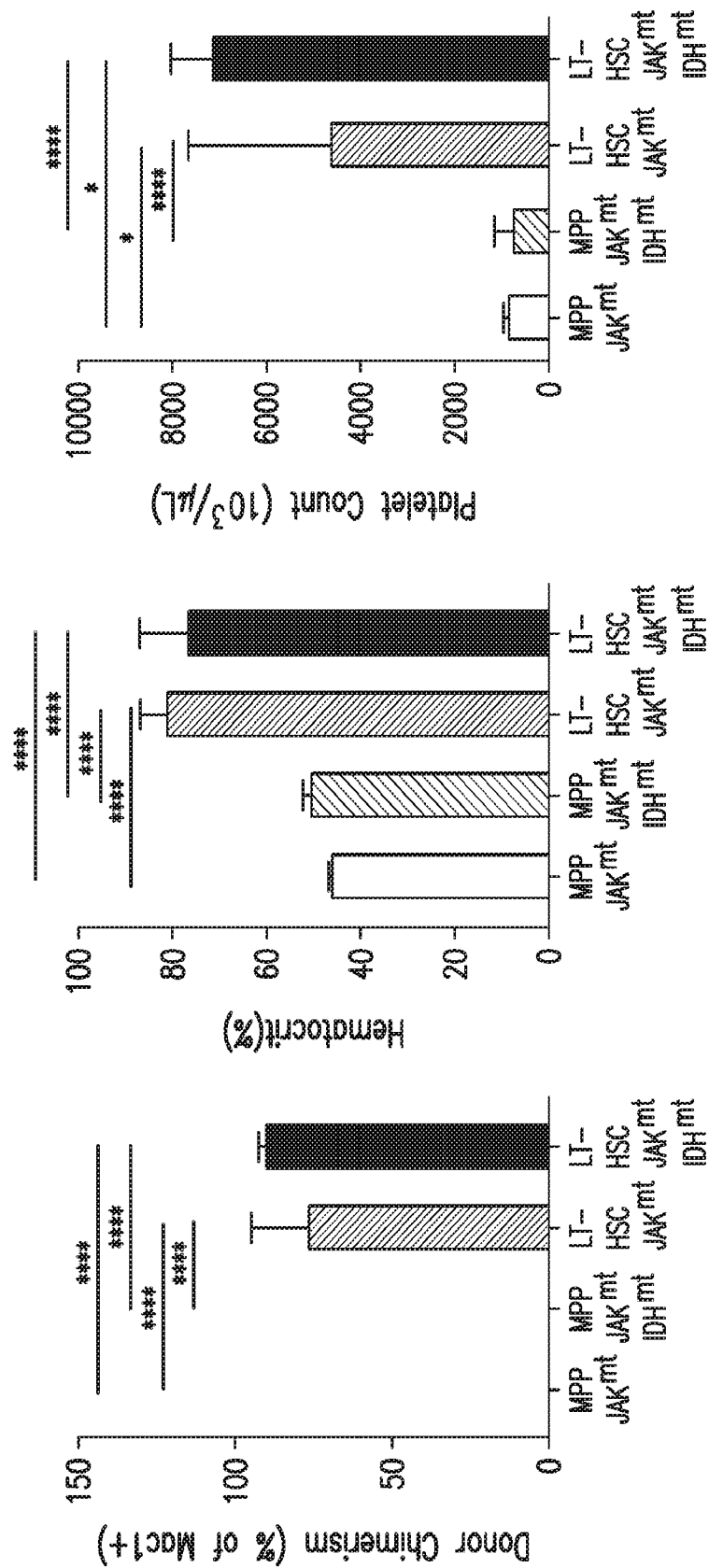
Figure 6B:
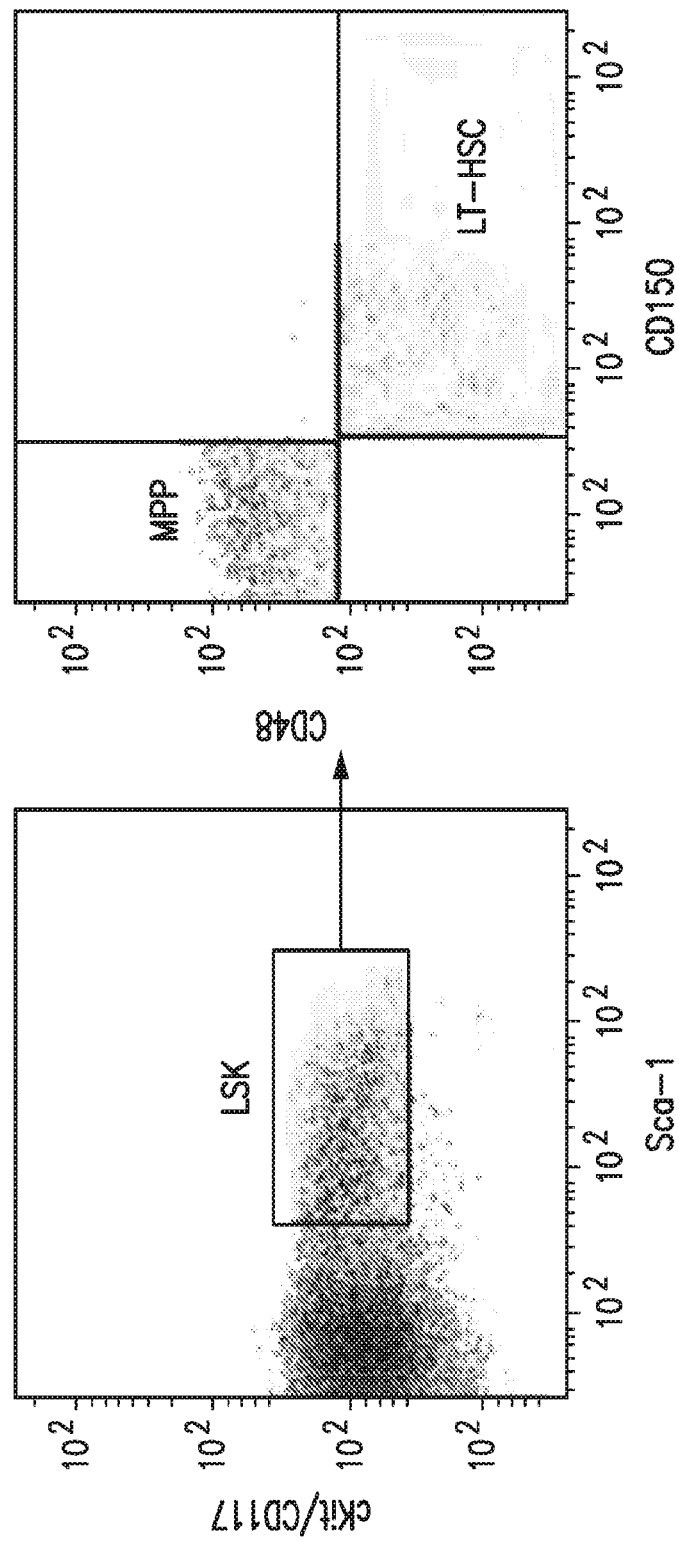

IDH1$^{R132H}$ and JAK2$^{V617F}$ bone marrow cells were sorted into LSK (Lin$^-$CD117/cKit$^+$ Sca1$^+$) long-term hematopoietic stem cell (LT-HSC; LSK CD48$^-$ CD150$^+$) and multipotent progenitors (MPP; LSK CD48$^+$ CD150-; FIG. 6B) populations and transplanted into congenic recipient mice. Disease chimerism, polycythemia, and thrombocythemia were assessed in recipient mice, which demonstrated that mice transplanted with LT-HSCs, but not MPPs, had evidence of long-term engraftment and myeloproliferation (FIG. 2B). LT-HSC transplanted recipients developed a lethal MPN consistent with efficient propagation of the disease from the stem cell compartment (FIG. 6C).

These data demonstrate that JAK2/IDH-mutant MPN is initiated and propagated in LT-HSCs, in contrast to IDH and Tet2-mutant AML models in which leukemic stem cell capacity is maintained in the MPP population.

Figure 2C:
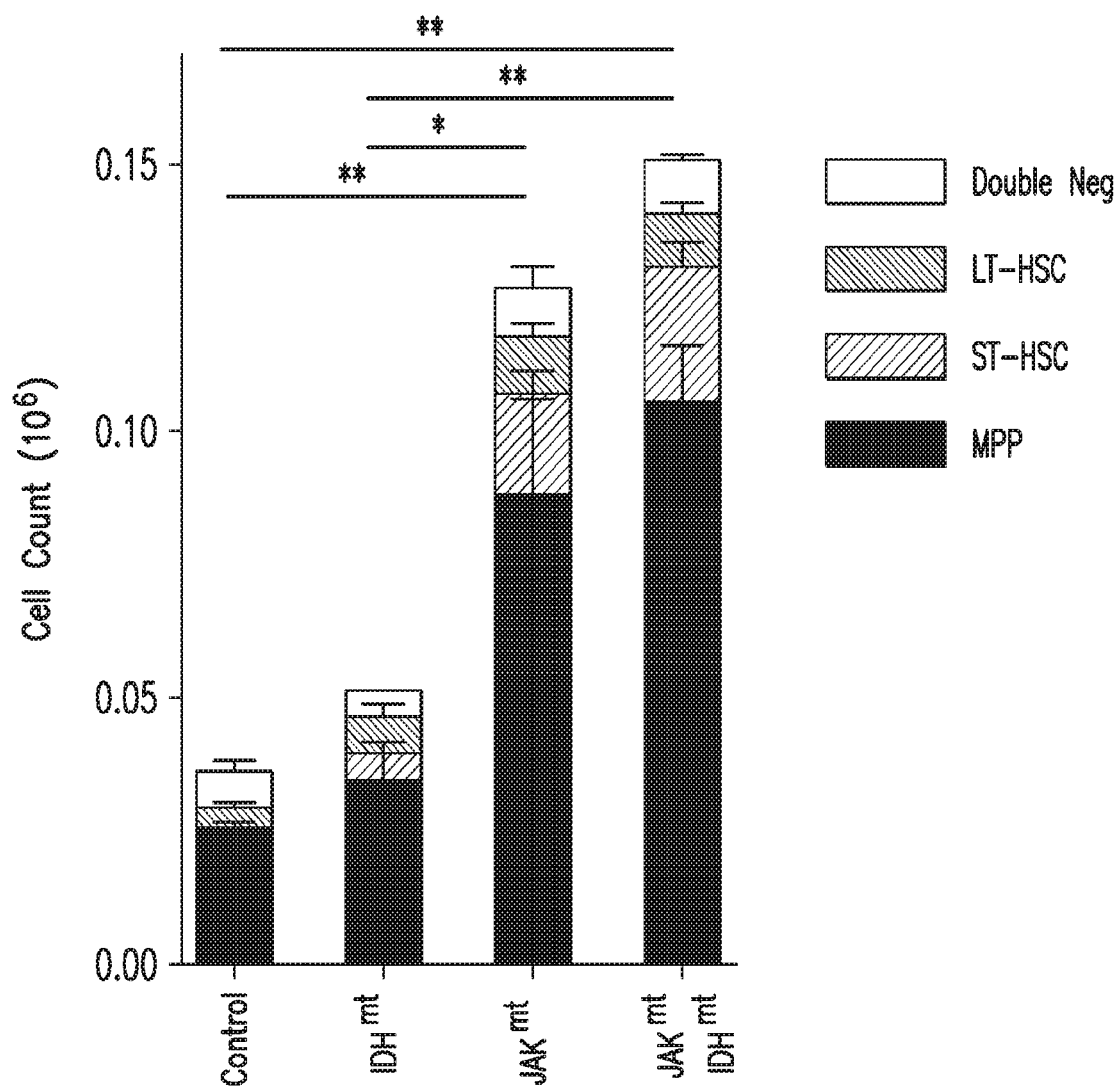
Figure 2D:
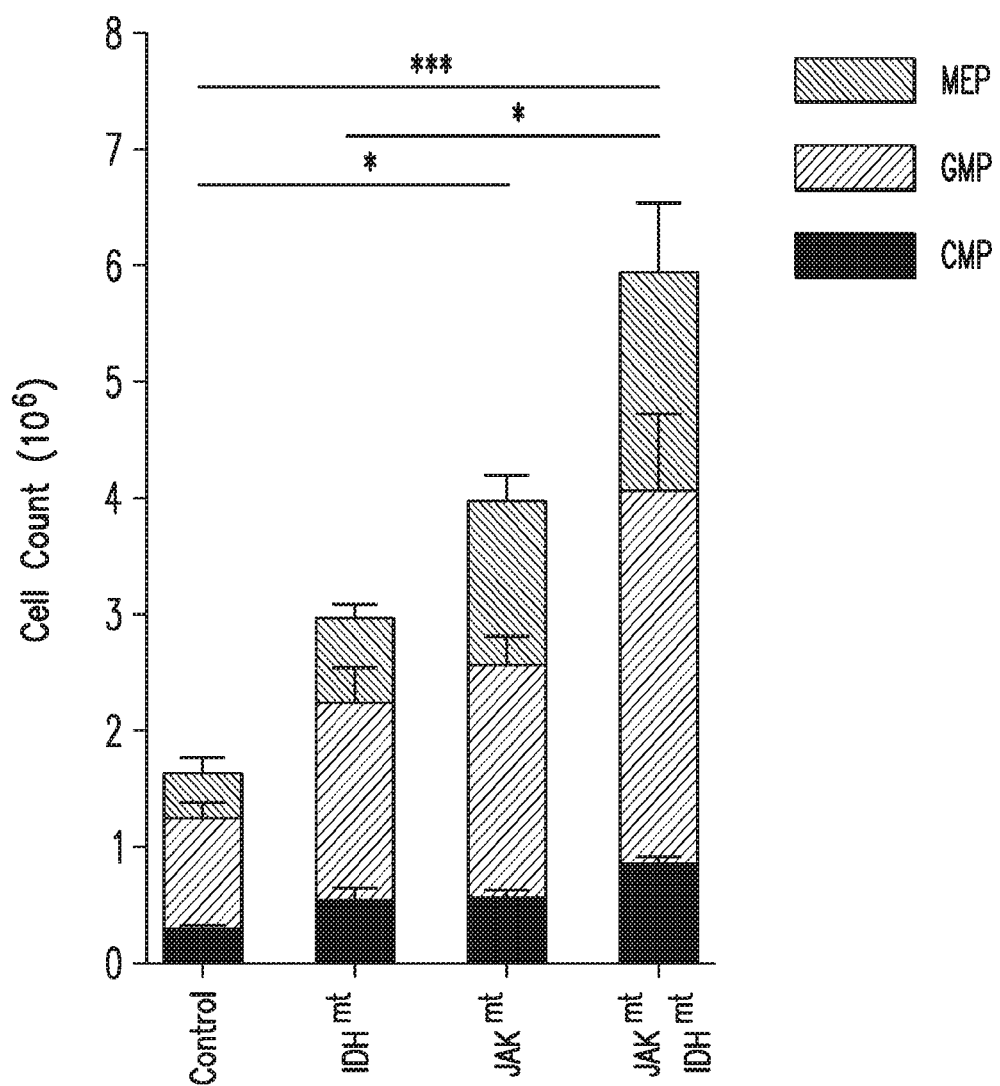
Figure 2E:
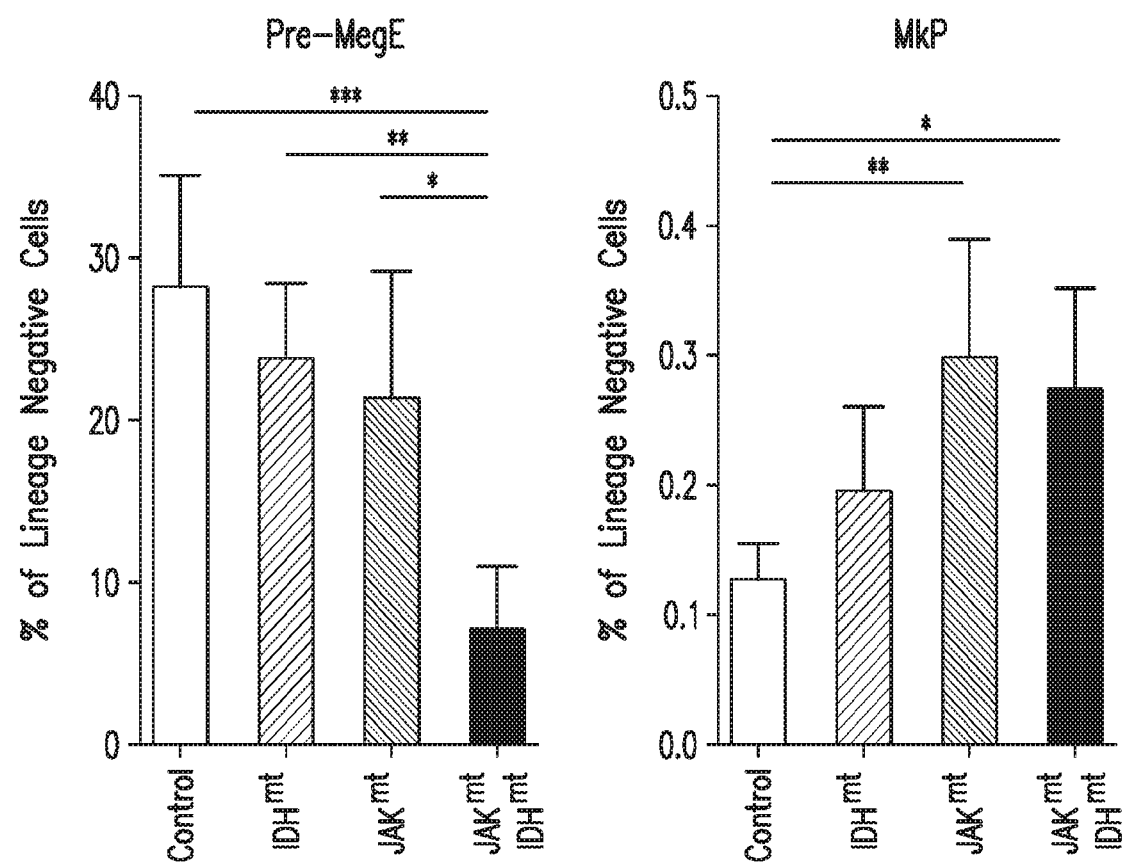
Figure 2F:
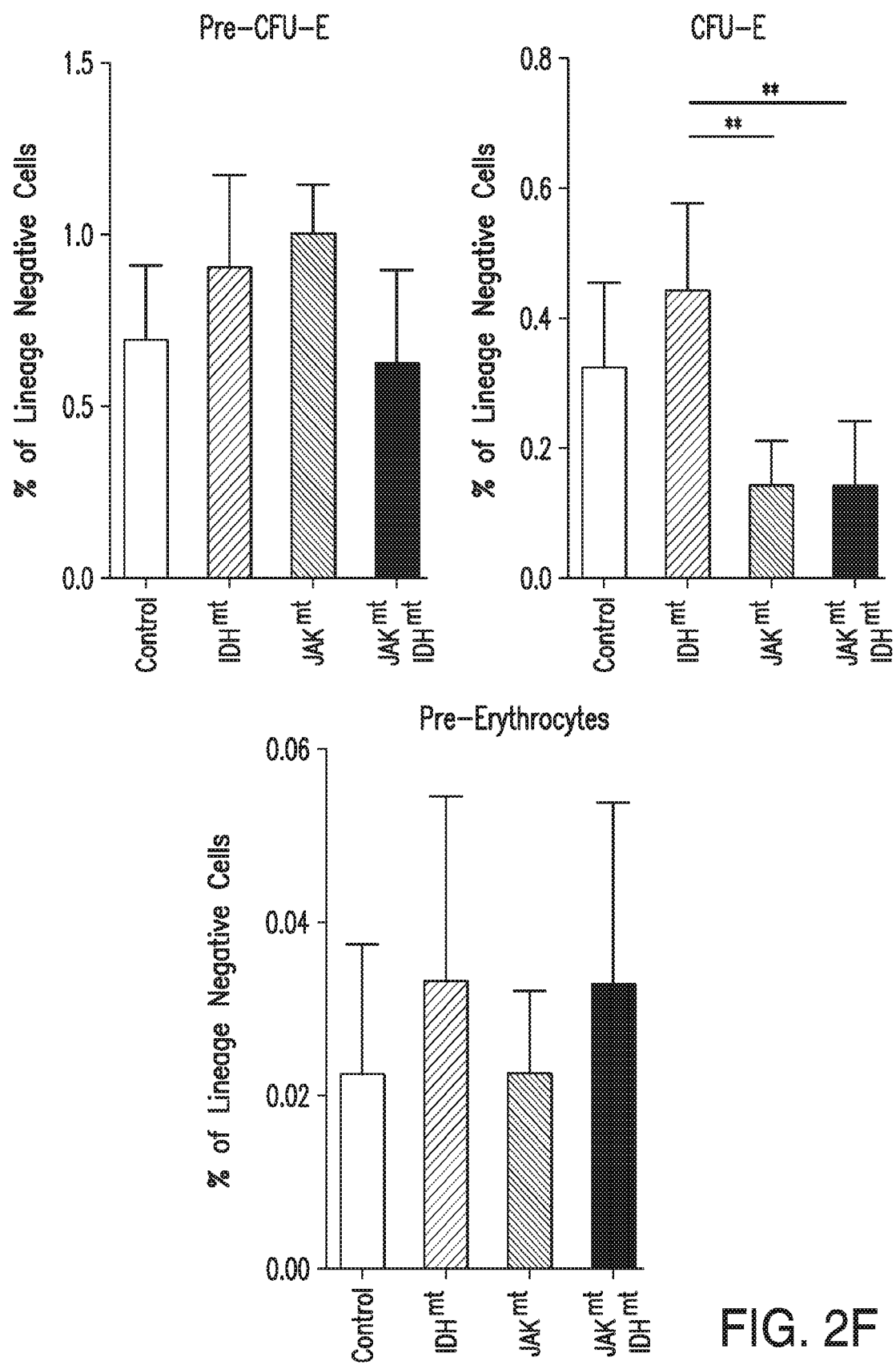
Figure 2G:
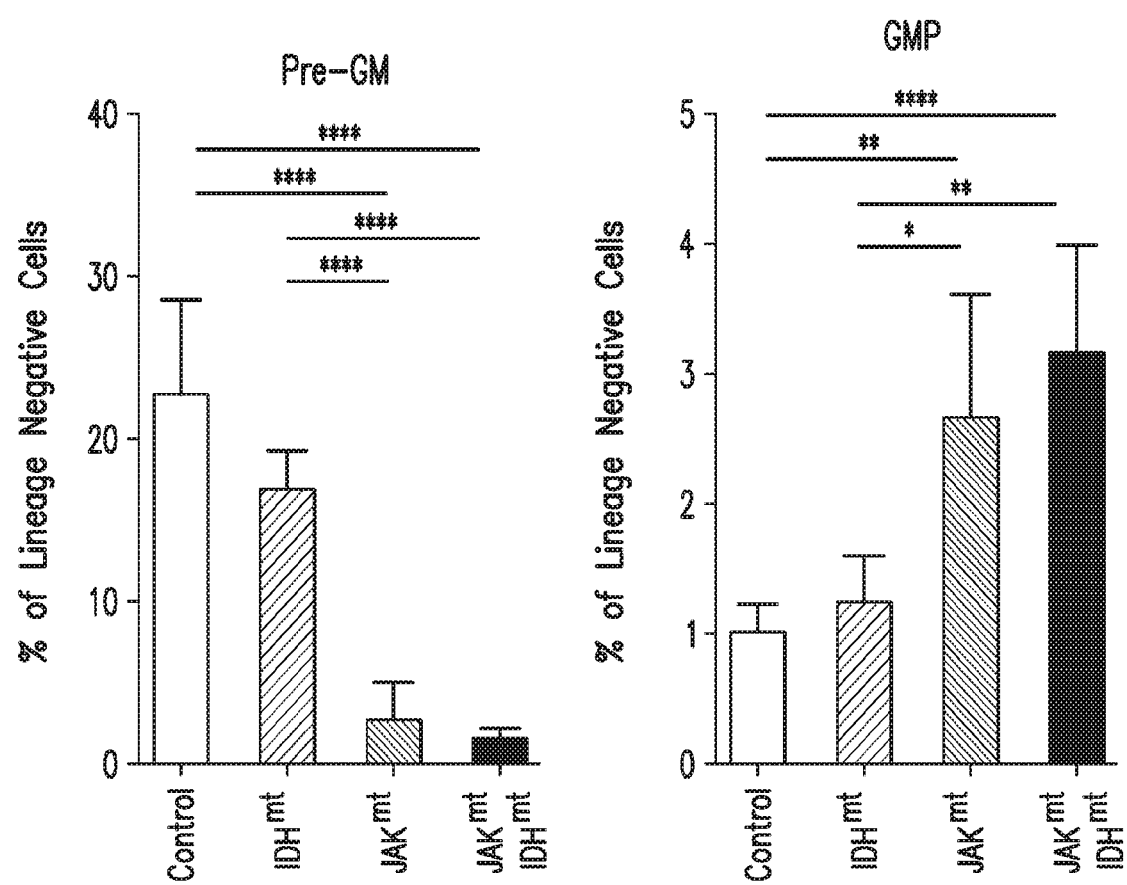
Figure 6D:
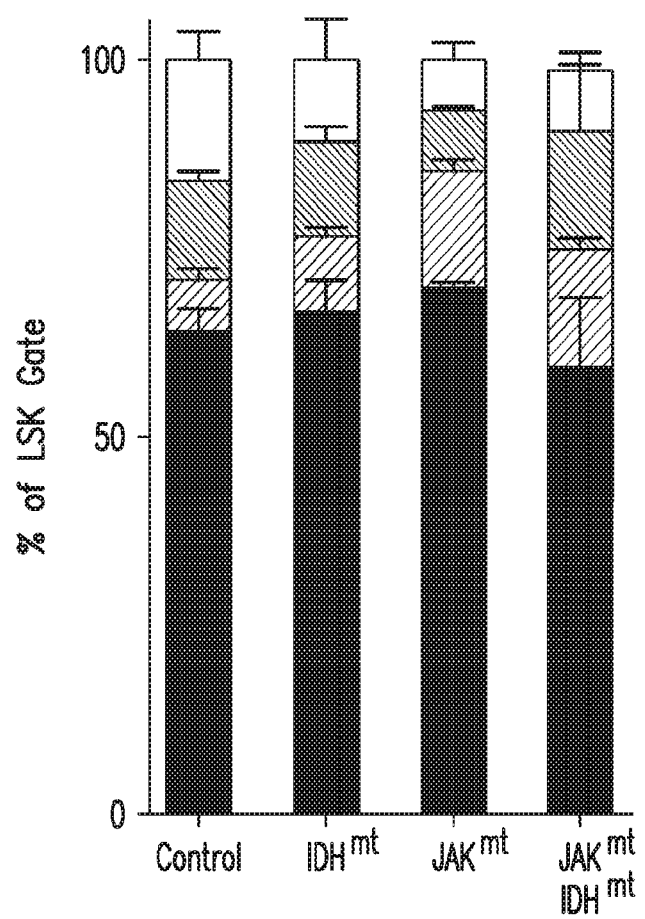
Figure 6E:
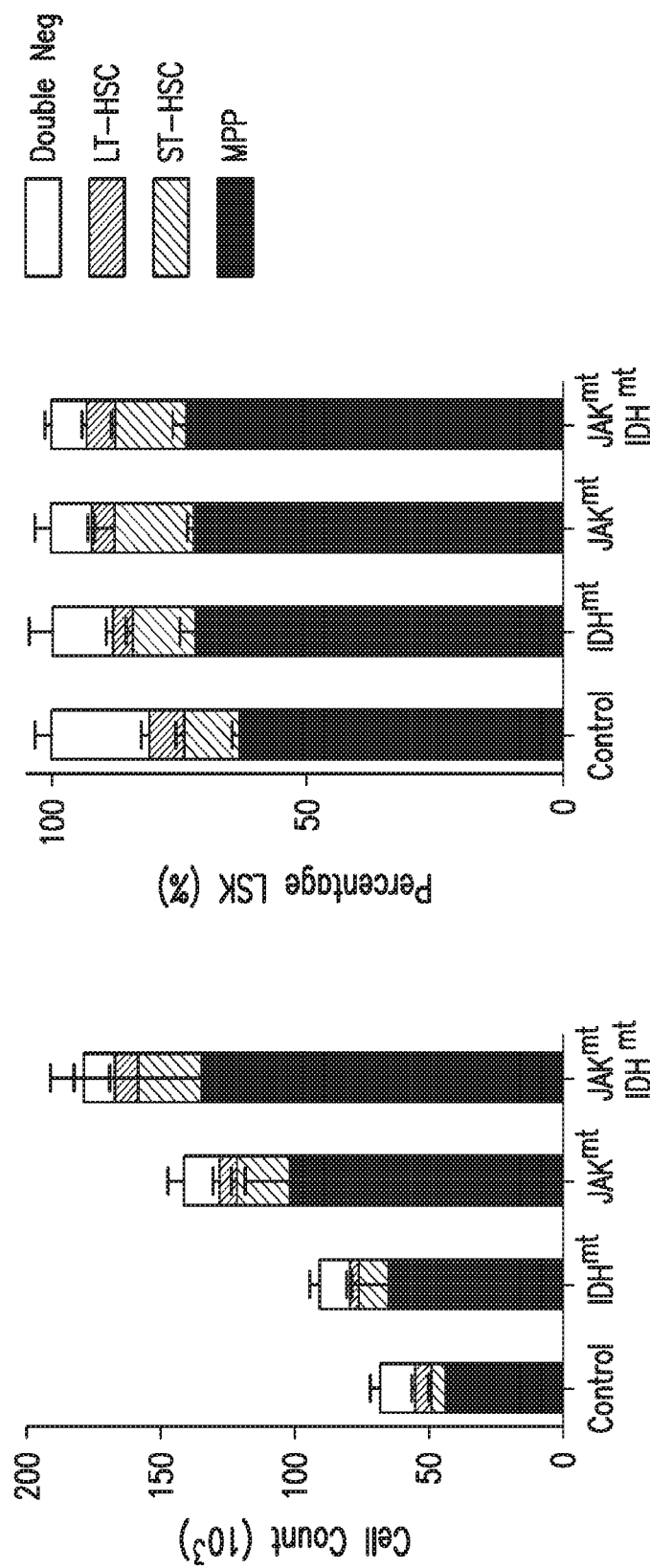
Figure 6F:
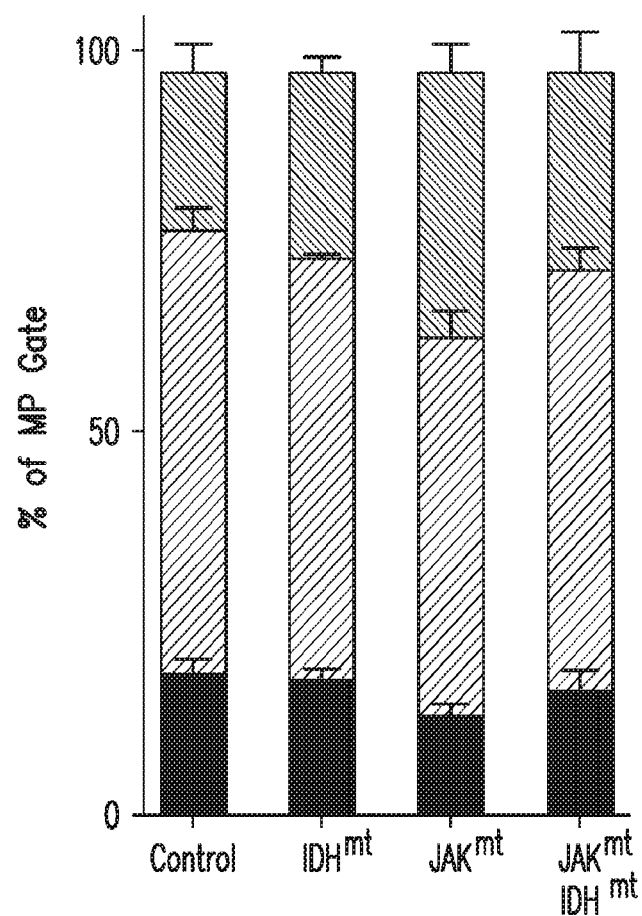
Figure 6G:
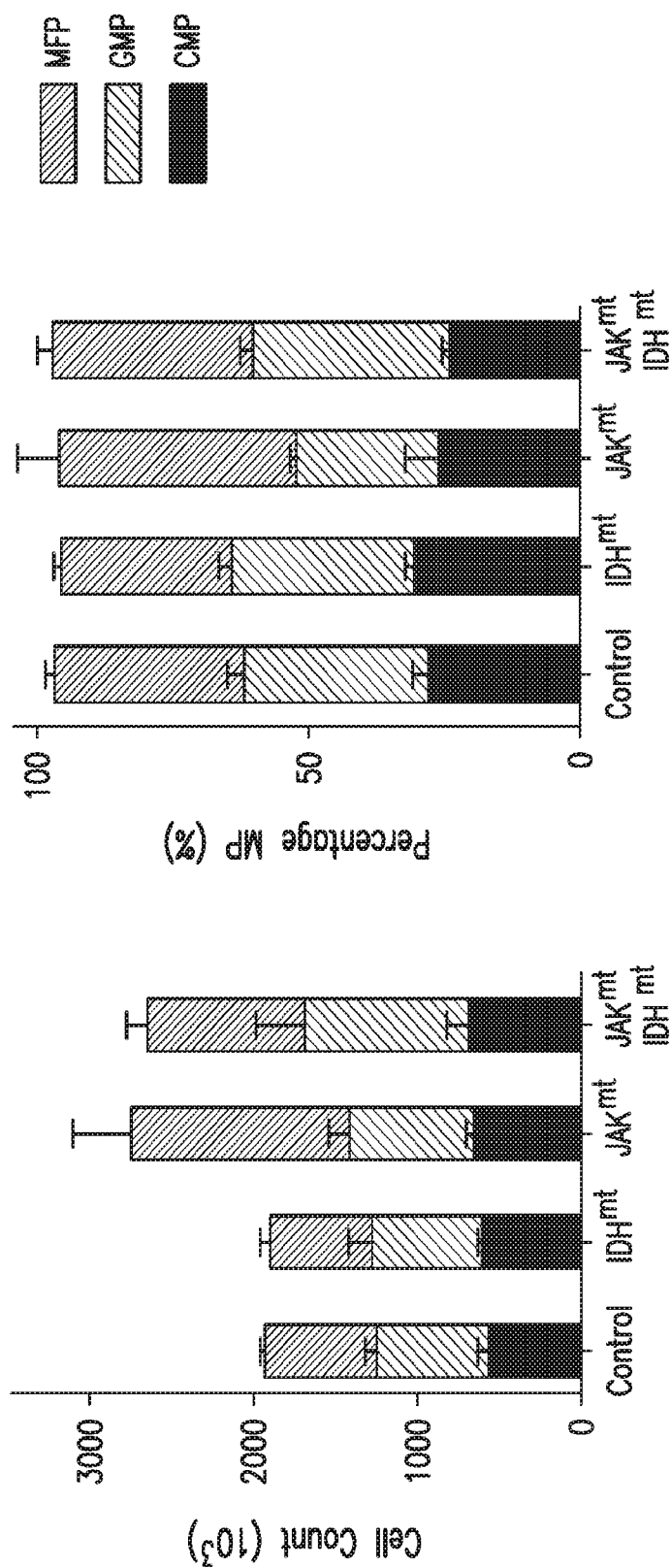

Next, the relative number of stem/progenitor cells in JAK2/IDH-mutant mice were assessed. It was found that total LSK numbers were expanded, with an increase in all hematopoietic stem and progenitor compartments (FIG. 2C, FIG. 6D, 6E). Concurrent JAK2/IDH mutations drove an increase in myeloid progenitors (MP: Lin$^-$Sca$^+$cKit$^-$) including an increase in common myeloid progenitors (CMP; Lin$^-$Sca$^+$cKit$^-$CD16/32$^-$CD34$^+$; FIG. 2G, FIG. 6F). Pre-Megakaryocyte populations (Pre-MegE: Lin$^-$cKit$^+$ Sca1$^-$CD41$^-$CD16/32$^-$CD150$^+$CD105$^-$) were significantly reduced in IDH2$^{R140Q}$ JAK2$^{V617F}$ combined mutants in comparison to JAK2$^{V617F}$ alone, while Megakaryocyte Progenitors (MkP: Lin⁻cKit⁺Sca1⁻CD150⁺CD41⁺) were expanded in JAK2$^{V617F}$ mice regardless of IDH status (FIG. 2E). With respect to erythroid progenitors, concurrent JAK2 and IDH2 mutations resulted in a reduction in CFU-E (Lin⁻cKit⁺Sca1⁻CD41⁻CD16/32⁻CD150⁻CD105⁺Ter119⁻) and an increase in pre-erythrocytes (Lin⁻cKit⁺Sca1⁻CD41⁻CD16/32⁻CD150⁻CD105⁺Ter119⁺) (FIG. 2F). In contrast, Pre-Granulocyte-Macrophage Progenitors (Pre-GM; Lin⁻cKit⁺Sca1⁻CD41⁻CD16/32⁻CD150⁻CD105⁻) were reduced while Granulocyte Macrophage Progenitors (GMP; Lin⁻cKit⁺Sca1⁻CD41⁻CD16/32⁺CD150⁻) were proportionally expanded (FIG. 2G).

These data indicate that combined mutant MPN shows perturbations in stem, progenitor and precursor populations with an increase in more primitive stem/progenitor cells and a decrease in mature megakaryocyte/erythroid populations.

Example 3

Combined JAK2/IDH2 Inhibition Shows Increased Efficacy in JAK2/IDH2-Mutant MPN

Figure 3A:
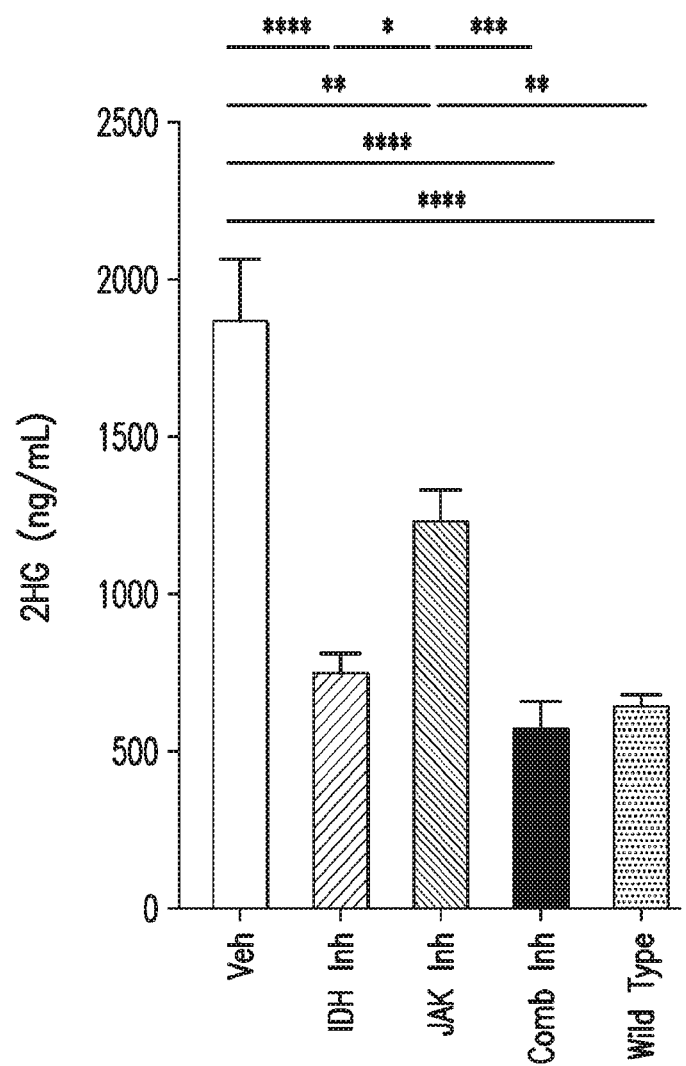
FIGS. 3A-3M illustrate that treatment of combined mutant mice results in resolution of disease phenotype and reduced disease chimerism.
Figure 3B:
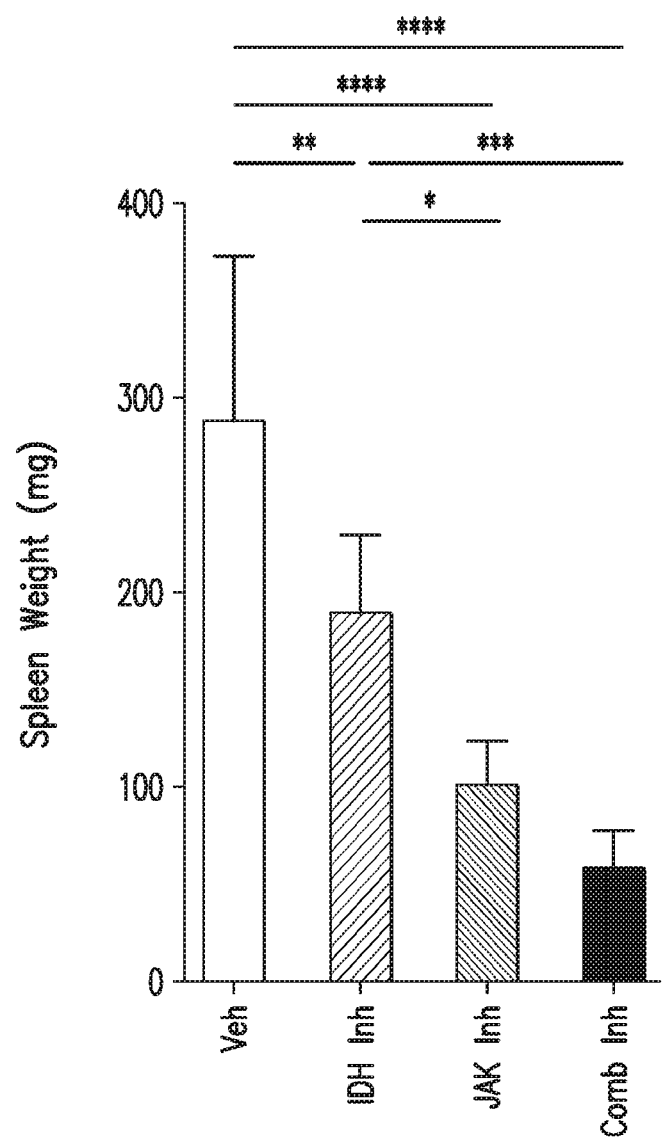
Figure 3C:
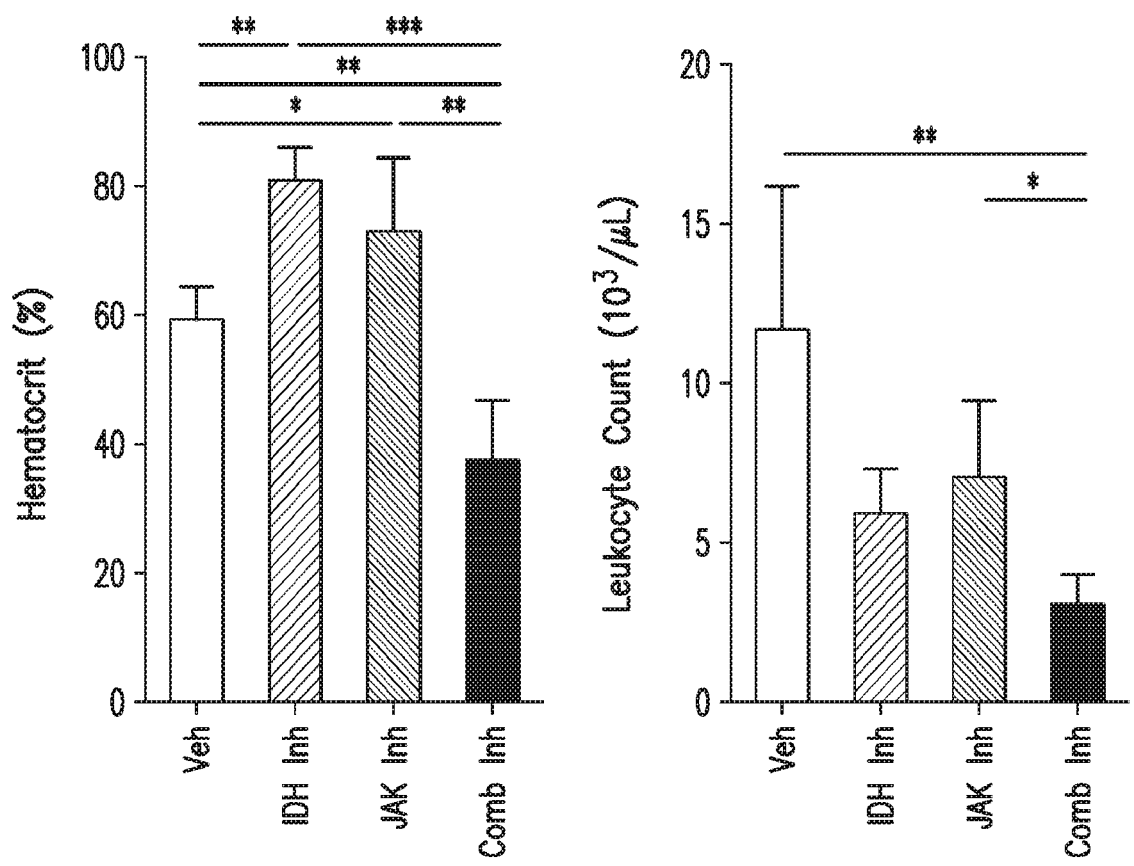
Figure 3D:
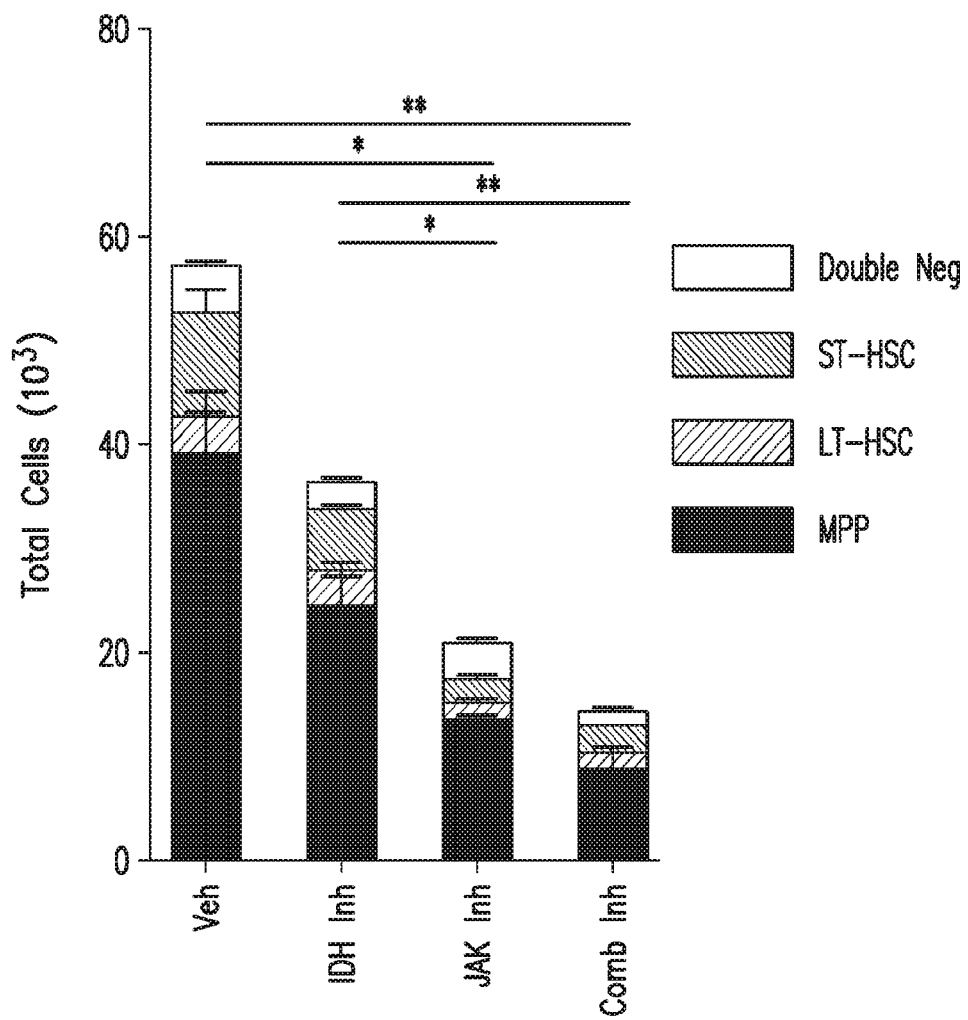
Figure 3E:
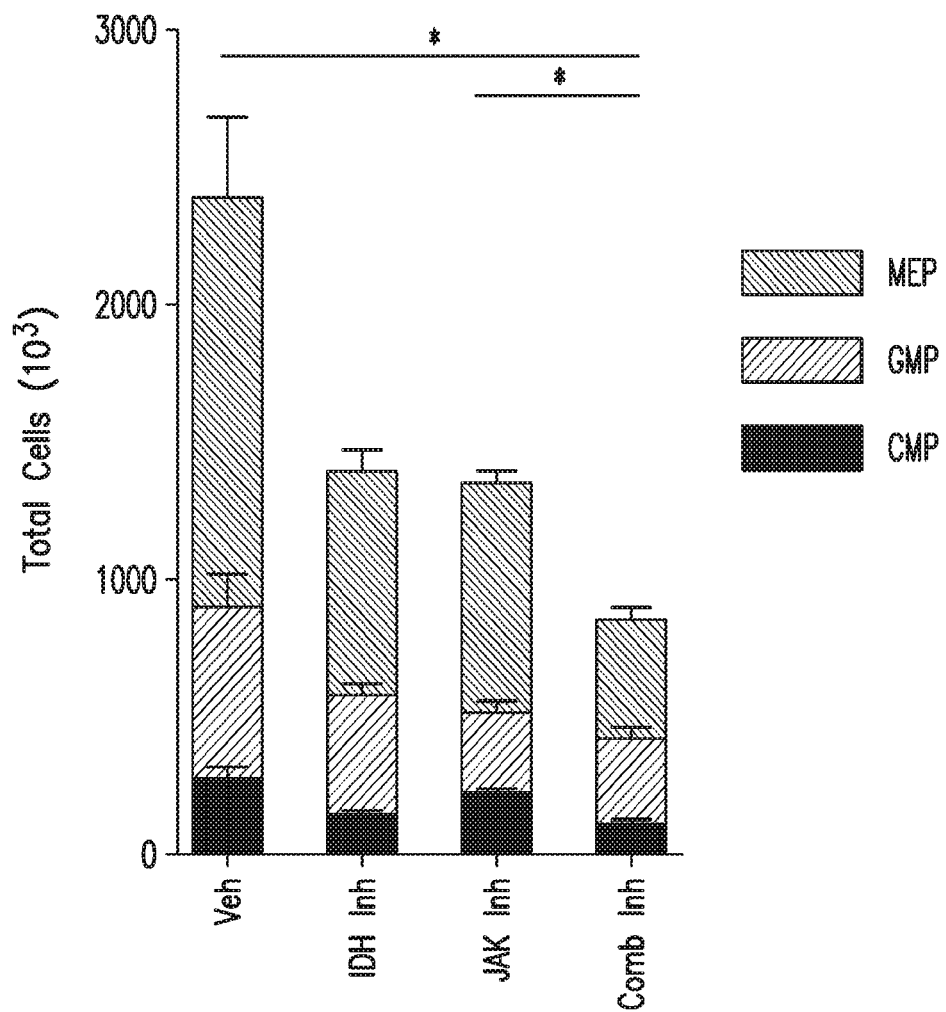
Figure 6H:
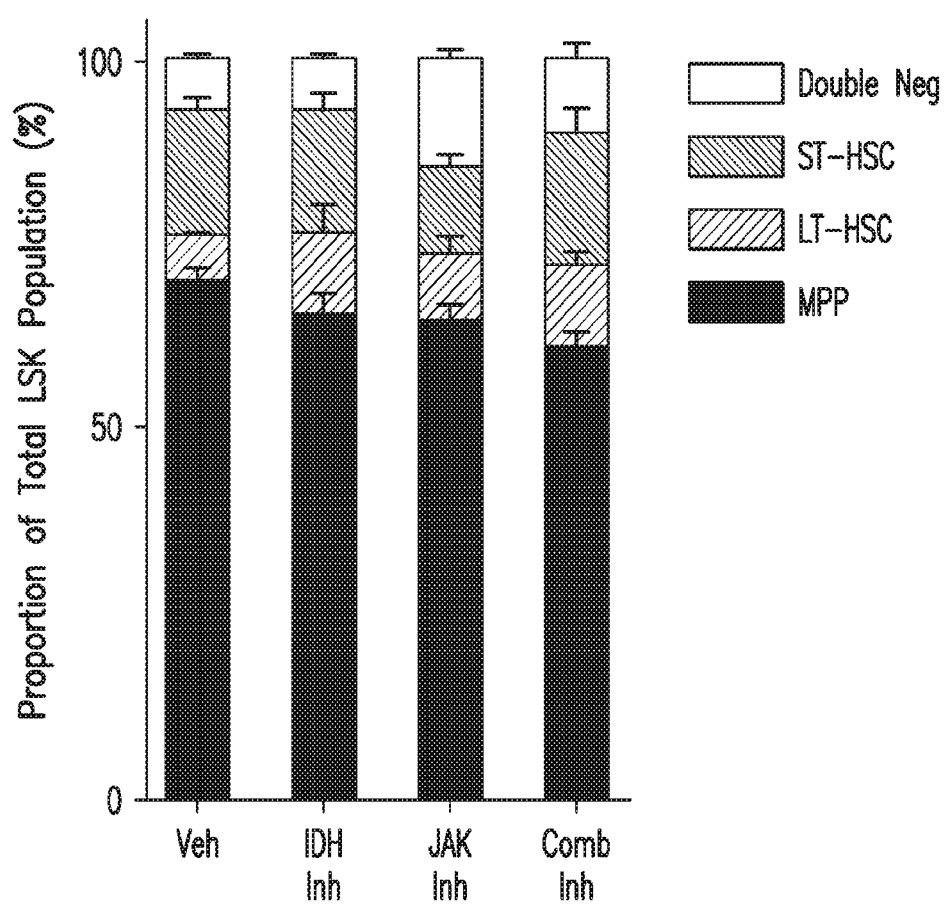
Figure 6I:
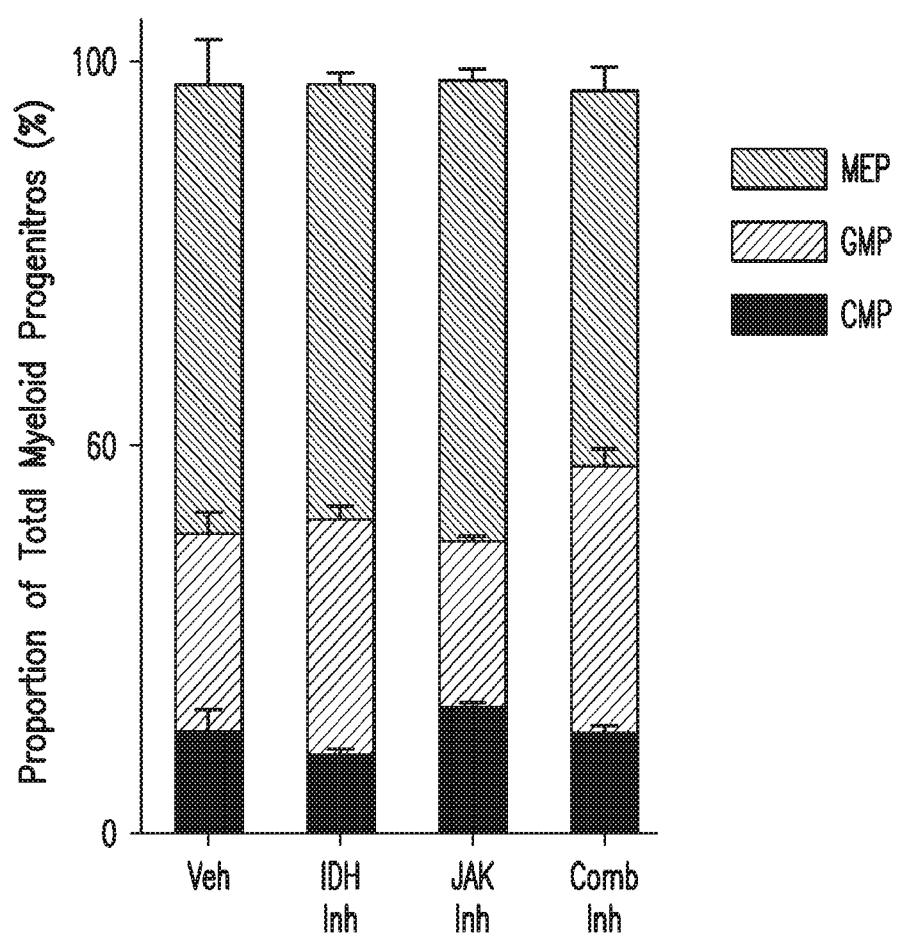

Given that MPN patients with concurrent JAK2 and IDH mutations are at high risk for disease progression and have an adverse clinical outcome, JAK2 inhibition, IDH2 inhibition, and combined JAK2/IDH2 inhibition were tested to determine efficacy in treating JAK2/IDH2-mutant MPN. Mice with CD45.2 JAK2/IDH2-mutant cells and with CD45.1 wild type cells were engrafted, and after recipient mice developed MPN, mice were treated with vehicle, the IDH2 inhibitor AG221, and/or the JAK kinase inhibitor ruxolitinib (INC18424). No evidence of synergistic or additive toxicity was observed with the combination therapy, and ruxolitinib therapy did not increase AG221 levels. Serum 2HG levels in mice engrafted with IDH2$^{R140Q}$ JAK2$^{V617F}$ mutant cells (mean 1874 ng/mL) were reduced with oral AG221 therapy at doses between 40-100 mg/kg given as monotherapy (mean 744.4, p<0.0001) or in combination with ruxolitinib (mean 562.6 ng/mL, p<0.0001), consistent with target inhibition (FIG. 3A). Interestingly, ruxolitinib monotherapy also modestly reduced serum 2HG levels (mean 1233 ng/mL, p=0.0016; FIG. 3A). Splenomegaly in diseased mice (vehicle mean 289.1 mg) was reduced by AG221 monotherapy (188.3 mg, p=0.0040) or ruxolitinib monotherapy (101.3 mg, p<0.0001), but splenomegaly resolved completely with combined therapy (59.53 mg, p<0.0001, FIG. 3B). Combined therapy with AG221 and ruxolitinib also normalized polycythemia (hematocrit 58.7% vs 37.61%, p=0.0028) and leukocytosis (11.62 K/uL vs 3.111 K/uL, p=0.0069) to an extent beyond that observed with either agent alone (FIG. 3C). Total LSK number in the bone marrow of double mutant mice (vehicle mean 57.19× 10³) was reduced by AG221 monotherapy (36.43×10³, ns), ruxolitinib monotherapy (20.73×10³, p=0.0266), or combined treatment (14.42×10³, p=0.0090); the reduction in stem/progenitor cells was seen in LT-HSCs, ST-HSCs, and MPPs to a similar extent (FIG. 3D; FIG. 6H). Combined treatment reduced total MP number in the bone marrow of double mutant mice (vehicle mean 2.46×10⁶ vs 0.8863×10⁶) to an extent greater than either agent alone and this reduction was seen in all measured subpopulations including CMP, GMP, and MEP (FIG. 3E; FIG. 6I).

Figure 3F:
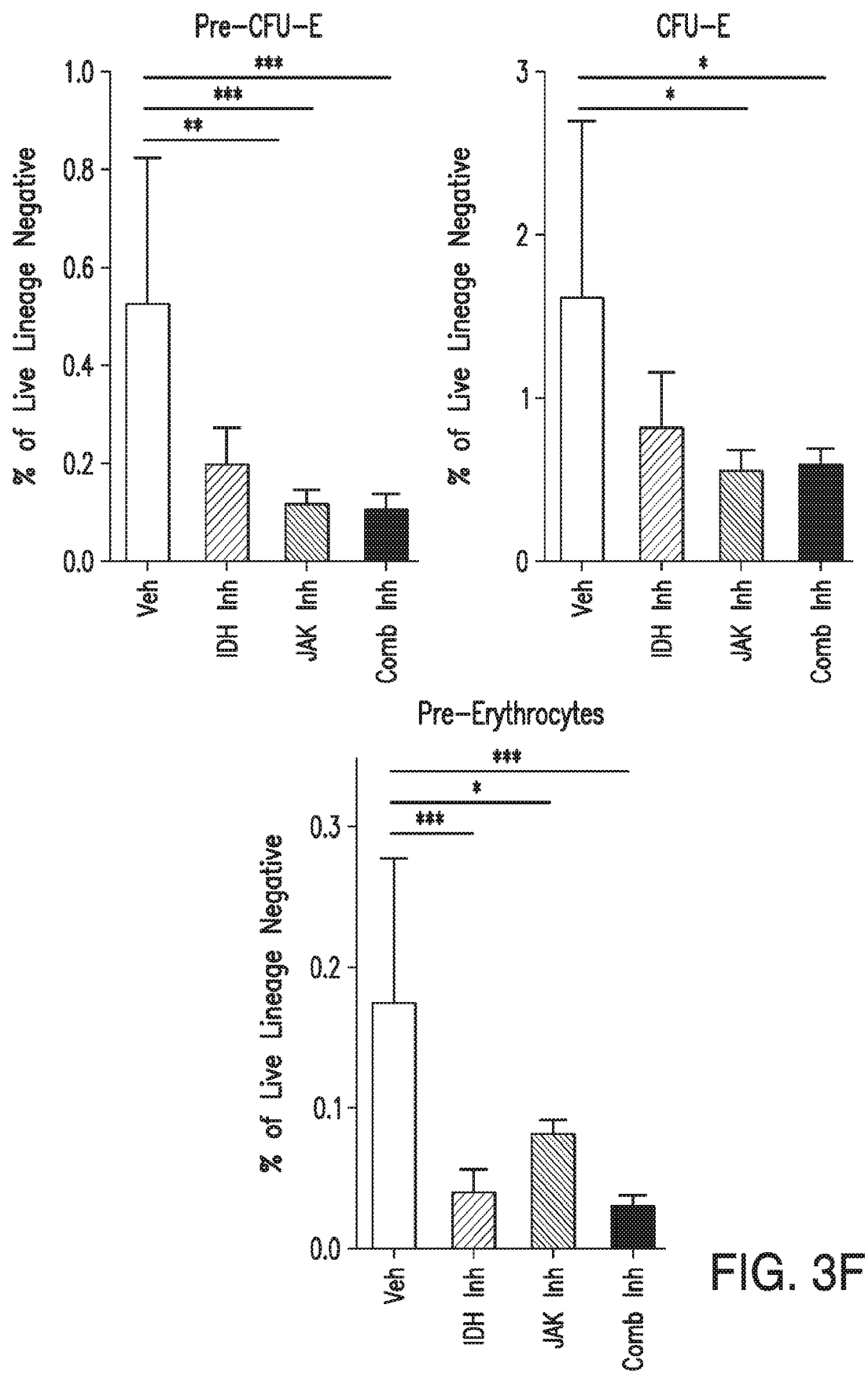
Figure 3G:
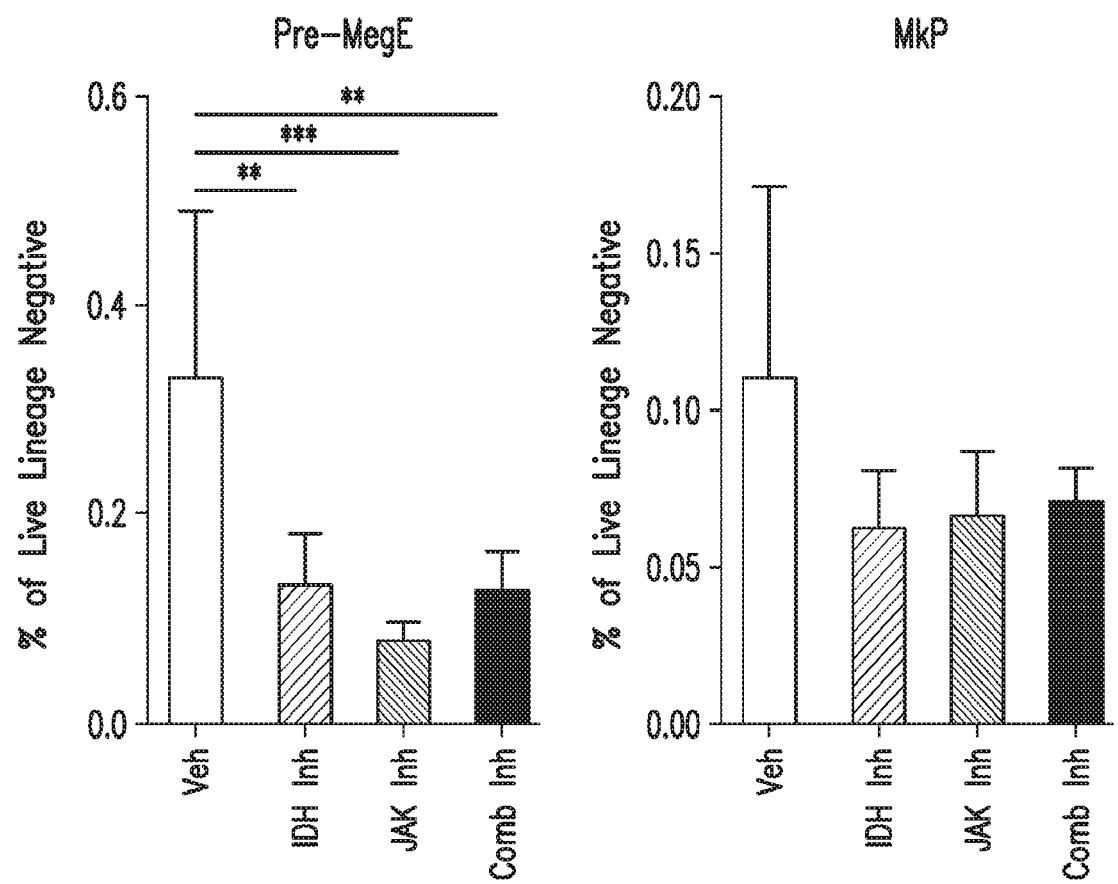
Figure 3H:
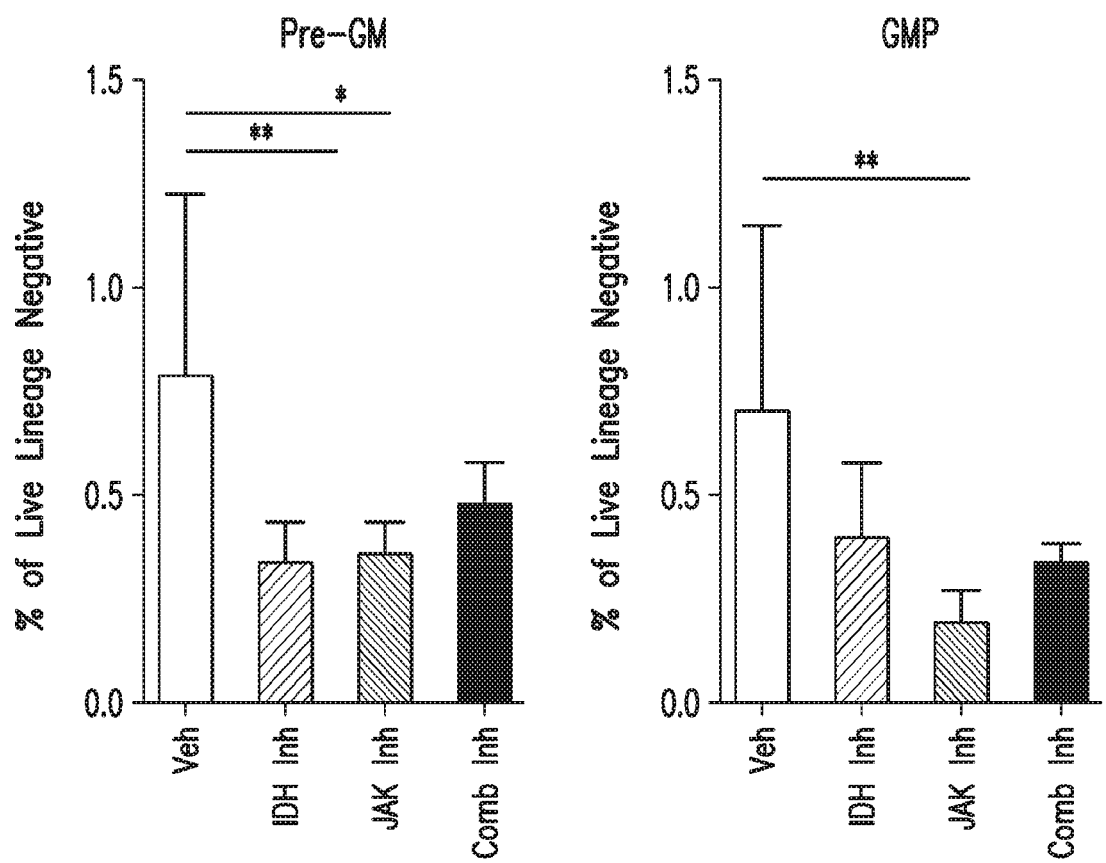

The expansion of erythrocyte progenitors was reduced with either ruxolitinib or AG221 monotherapy or combined therapy. These included Pre-CFU-E (Vehicle mean 0.5189% vs AG221 0.1913%, p=0.0051; vs ruxolitinib 0.1103%, p=0.0005; vs Combined 0.09978% p=0.0006), CFU-E (Vehicle 1.621 vs AG 0.8251, p=ns; vs ruxolitinib 0.5553, p=0.0105; vs Combination 0.5868, p=0.0180), and Pre-erythrocytes (Vehicle 0.1757 vs AG221 0.03906, p=0.0005; vs ruxolitinib 0.08063, p=0.0149; vs Combination 0.02943, p=0.0003 (FIG. 3F). Treatment with either monotherapy or combined therapy reduced Pre-MegE populations (Vehicle 0.1757 vs AG221 0.03906, p=0.0005; vs ruxolitinib 0.08063, p=0.0149; vs Combination 0.02943, p=0.0003) with a trend towards a reduction in the expanded MkP populations in all treatment groups (FIG. 3G). Similarly, combined therapy or monotherapy reduced Pre-GM and GMP populations (FIG. 3H).

Example 4

IDH2 Inhibition or Combined JAK2/IDH2 Inhibition Reduces Disease Burden In Vivo

Since JAK2 inhibitors do not substantively reduce allele burden in preclinical models of JAK2 mutant disease (see, Quintás-Cardama et al. Preclinical characterization of the selective JAK1/2 inhibitor INCB018424: therapeutic implications for the treatment of myeloproliferative neoplasms, *Blood.* 2010;115:3109-17) or in the clinical context, (see Verstovsek et al. A double-blind, placebo-controlled trial of ruxolitinib for myelofibrosis. *New England Journal of Medicine* 2012;366:799-807 and Verstovsek et al. Safety and efficacy of INCB018424, a JAK1 and JAK2 inhibitor, in myelofibrosis. *New England Journal of Medicine* 2010;363: 1117-27), a study was conducted to assess whether IDH2 inhibition, alone or in combination with JAK2 inhibition, could reduce disease burden in vivo. The impact of AG221 therapy or AG221/ruxolitinib combined therapy on the proportion of IDH2$^{R140Q}$ JAK2$^{V617F}$ MPN cells (CD45.2⁺) in recipient mice was assessed.

Figure 3I:
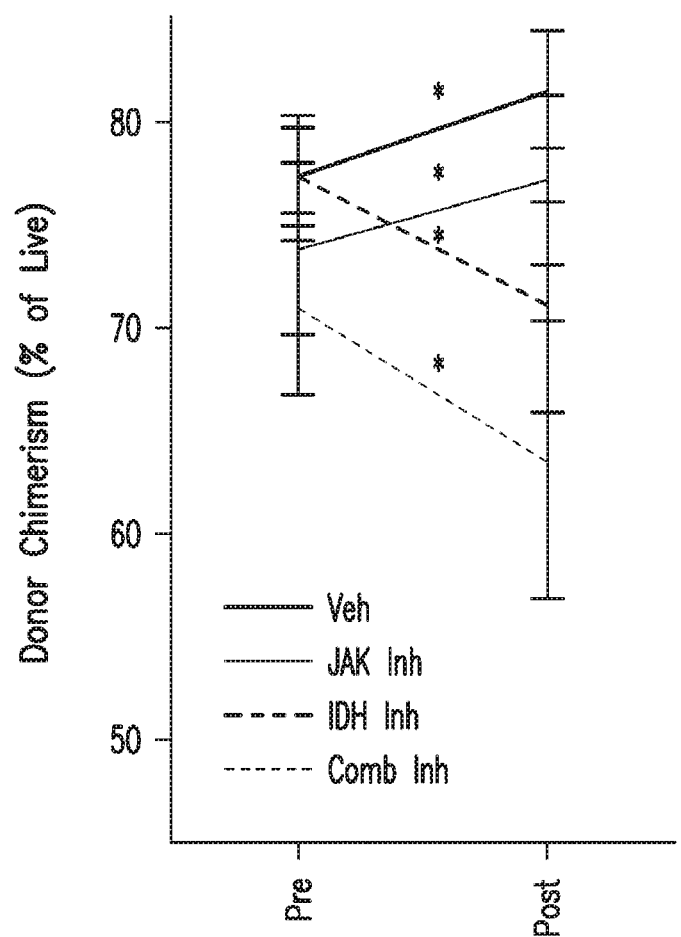
Figure 3J:
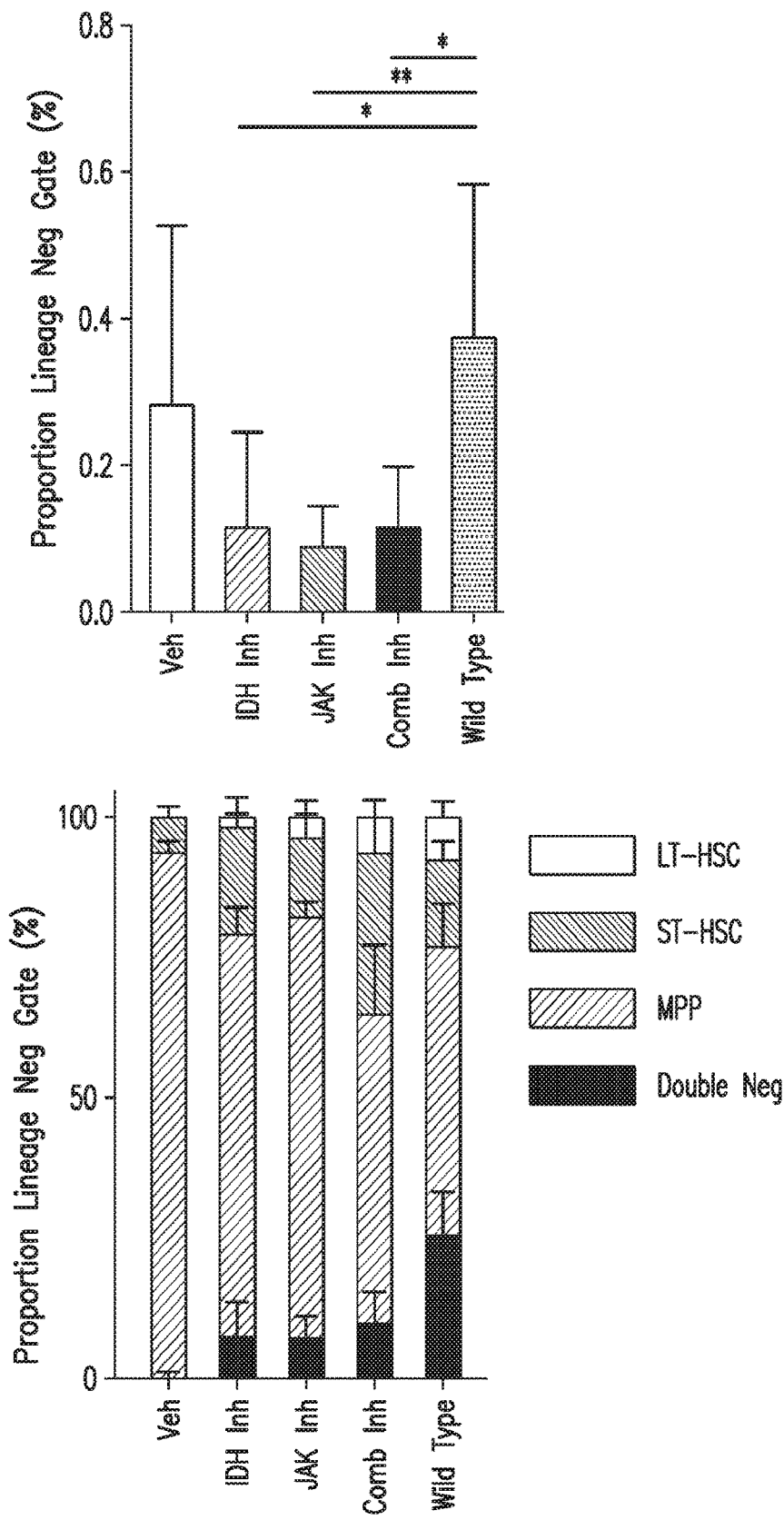
Figure 3K:
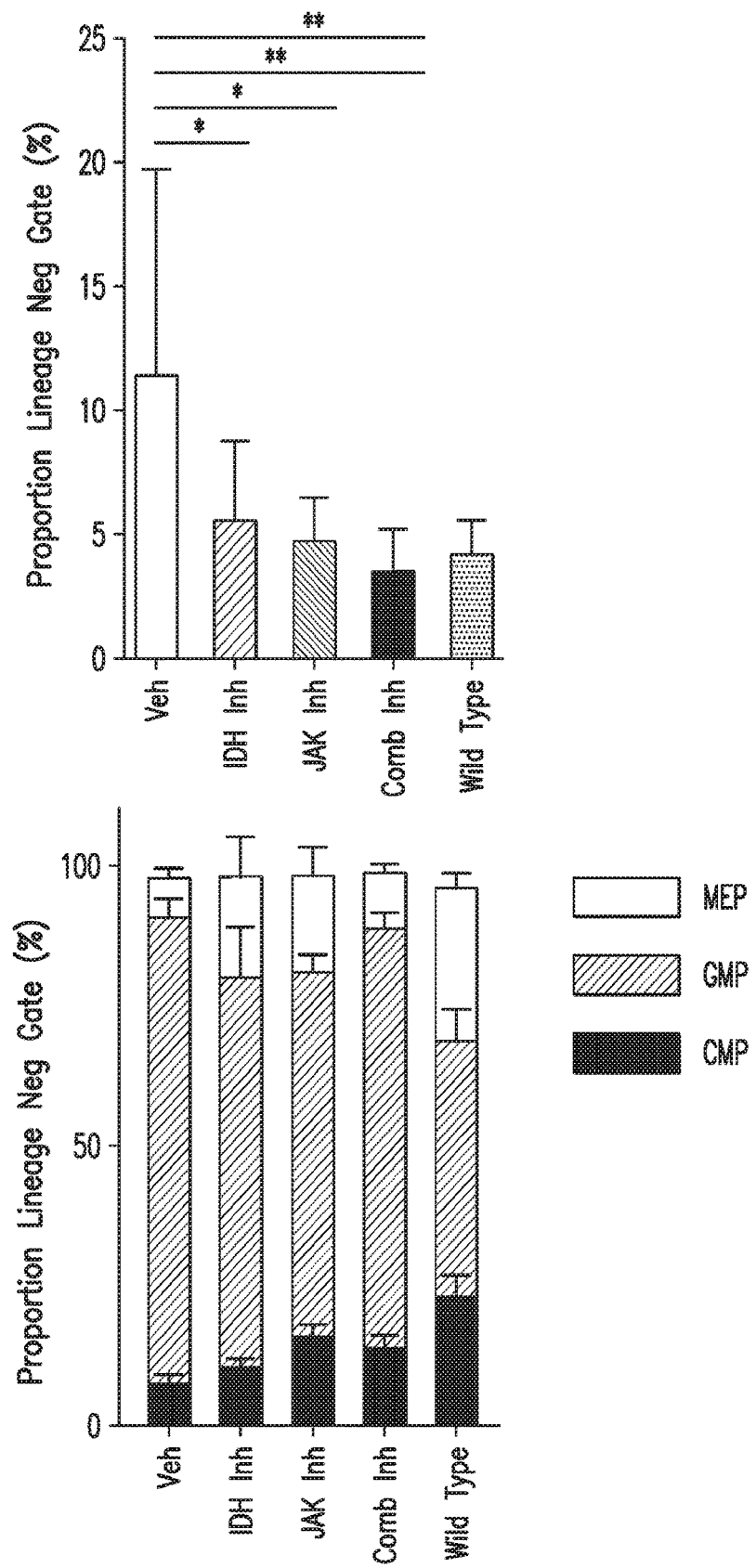
Figure 3L:
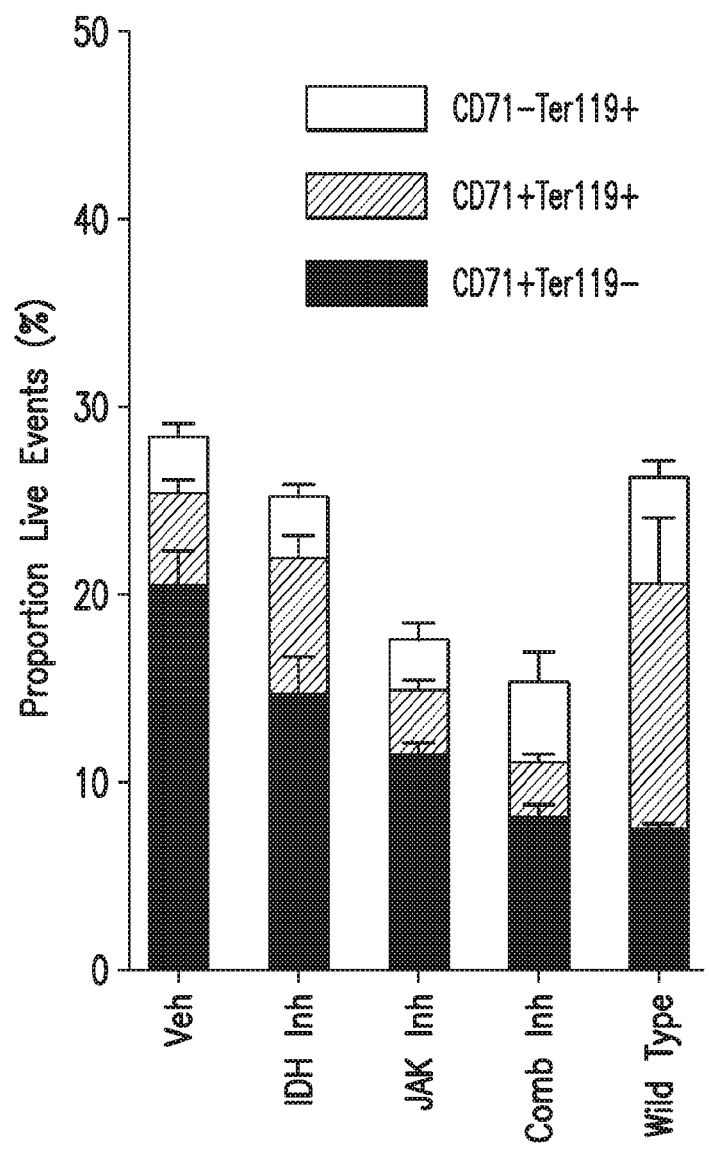

In comparing allele burden in the peripheral blood from individual mice before and after treatment, it was observed that mice treated with either AG221 or combined JAK2/IDH2 inhibition showed significant reductions in mutant donor chimerism (mean change pre- and post-treatment for AG221 -6.291%, p=0.0411 and for Combination -7.547%, p=0.0225). In contrast, mice treated with either ruxolitinib or vehicle showed significant expansion of mutant allele burden (mean change pre- and post-treatment for ruxolitinib+3.256%, p=0.0122 and for Vehicle+4.236, p=0.0374; FIG. 3I). Examining only donor-derived (CD45.2⁺) cells, monotherapy with either inhibitor or combined IDH2/JAK2 inhibitor therapy reduced the proportion of CD45.2 LSKs (FIG. 3J), whereas the number of CD45.1 wild type stem/progenitor cells was not affected (data not shown) indicating a potent, selective effect of AG221 on mutant cells in vivo. Within the donor-derived LSK compartment, LSK LT-HSC, ST-HSC, and MPP subpopulations returned to wild type levels. Consistent with the effect on stem/progenitor cells, it was found that IDH2 inhibitor monotherapy or combined IDH2/JAK2 inhibitor therapy reduced the proportion of CD45.2 myeloid progenitor populations (FIG. 3K) without affecting the number of CD45.1 myeloid progenitors. Within the donor-derived MP compartment, subpopulations including CMP, GMP, and MEP also were partially normalized with either monotherapy or combined therapy (FIG. 3K). The proportion of CD45.2 mutant erythoid progenitors (CD71⁺Ter119⁻) cells was normalized with combination therapy consistent with a potent suppression of mutant erythroid progenitors (FIG. 3L).

Figure 3M:
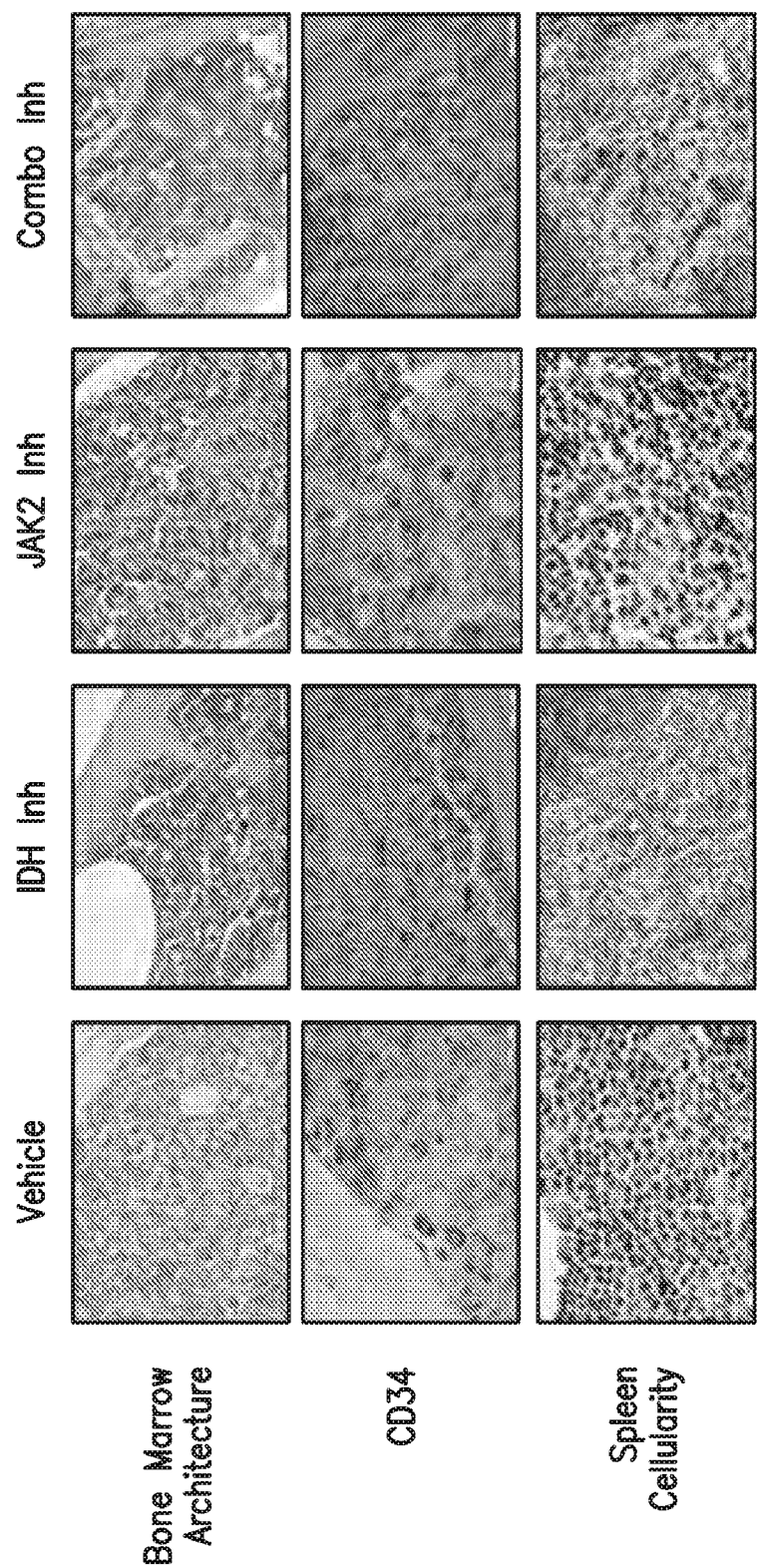

Histologically, treatment with JAK2/IDH2 combination therapy normalized bone marrow and spleen morphology, with a reduction in the proportion of myeloid cells and the return of normal diletations in the bone. Treatment with AG221, but not ruxolitinib, resulted the aberrant CD34 expression seen in megakaryocytes, whereas combined treatment eliminated the presence of these cells. It was observed the AG221 or AG221/ruxolitinib combination therapy eliminated the expansion of spleen blasts observed in untreated JAK2/IDH2 mutant MPN (FIG. 3M).

Example 5

Figure 4A:
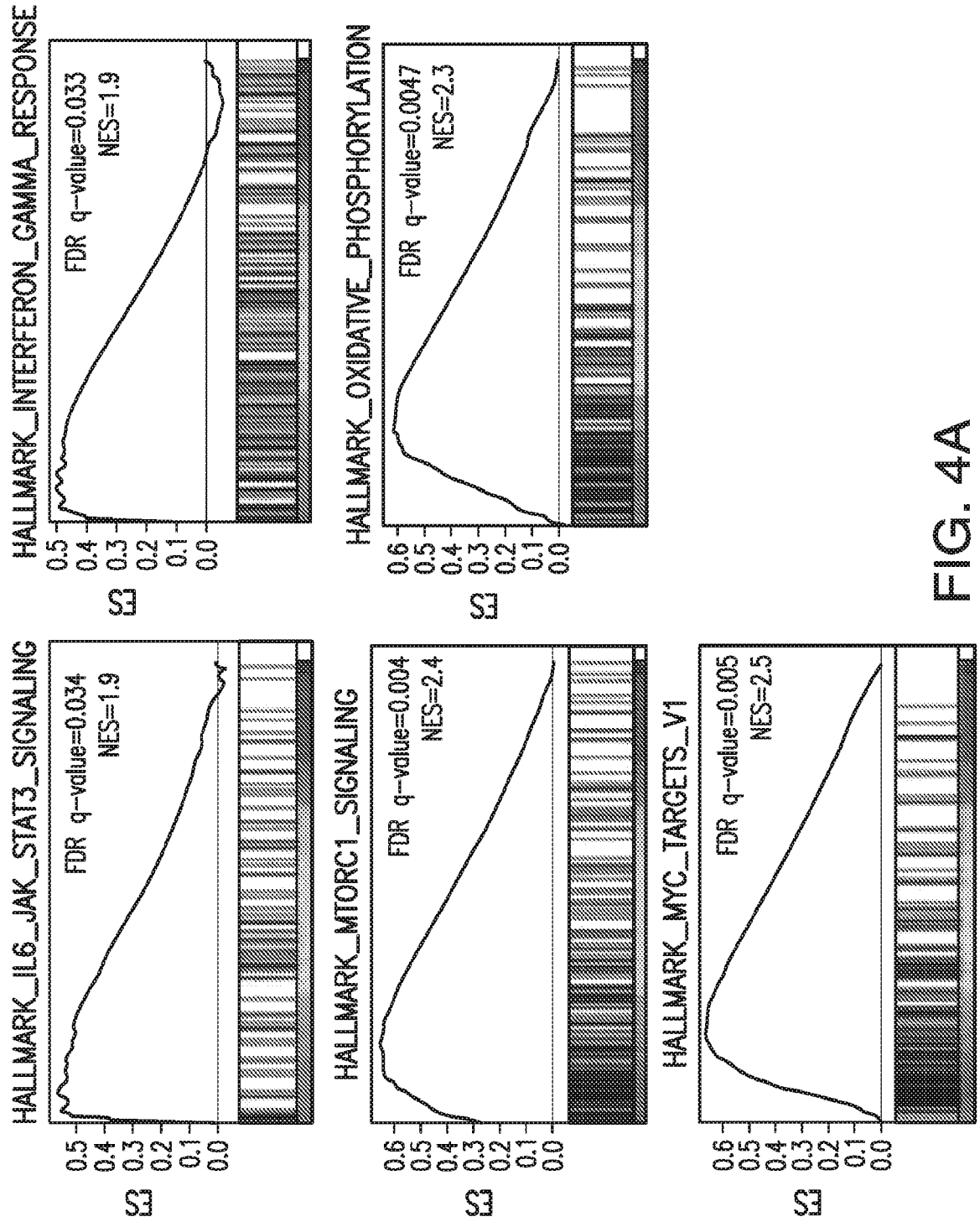
FIGS. 4A-4H illustrates that expression in donor derived (CD45.2+) LSK by RNASeq defines geneset of combined mutant disease and treatment eradicates this expression profile.

Combined JAK2/IDH2 Inhibition Normalizes Aberrant Transcription in JAK2/IDH2-Mutant MPN Given the role of JAK2 as a transcription factor, and the ability of mutant IDH to modulate epigenetic state (see Xu et al. Oncometabolite 2-Hydroxyglutarate Is a Competitive Inhibitor of a-Ketoglutarate-Dependent Dioxygenases, *Cancer Cell*, 2011;19:17-30; and Figueroa et al., Leukemic IDH1 and IDH2 Mutations Result in a Hypermethylation Phenotype, Disrupt TET2 Function, and Impair Hematopoietic Differentiation, *Cancer Cell* 2010;18:553-67), the effect of combined JAK2/IDH2 mutation on gene expression in vivo was studied. Additioanlly, the effect of combined IDH2/JAK2 inhibition was studied. Mutant CD45.2 LSKs were harvested and sorted from recipient mice engrafted with JAK2/IDH2 mutant cells which were treated with vehicle, AG221, ruxolitinib, or combination therapy and their transcriptional output was compared to each other and to wild type cells through RNA-sequencing. $IDH2^{R140Q}$ $JAK2^{V617F}$ mutant LSK had a distinct gene expression profile compared to wild type LSKs. This gene expression profile enriched for MSigDB Hallmark gene sets related to JAK-STAT signaling including IL6/JAK/STAT3 signaling (q=0.034, NES=1.9) and interferon gamma signaling (q=0.033, NES=1.9) gene sets (FIG. 4A). Enriched expression of gene sets related to metabolism was observed, including mTOR (q=0.005, NES=2.4) and oxidative phosphorylation (q=0.0047, NES=2.3; FIG. 4A.). Finally, certain oncogenic signatures such as cMYC (q=0.004, NES=2.5) were increased in expression in JAK2/IDH2-mutant cells. Together these data suggest that concurrent $IDH2^{R140Q}$ and $JAK2^{V617F}$ mutations result in transcriptional alterations.

Figure 4B:
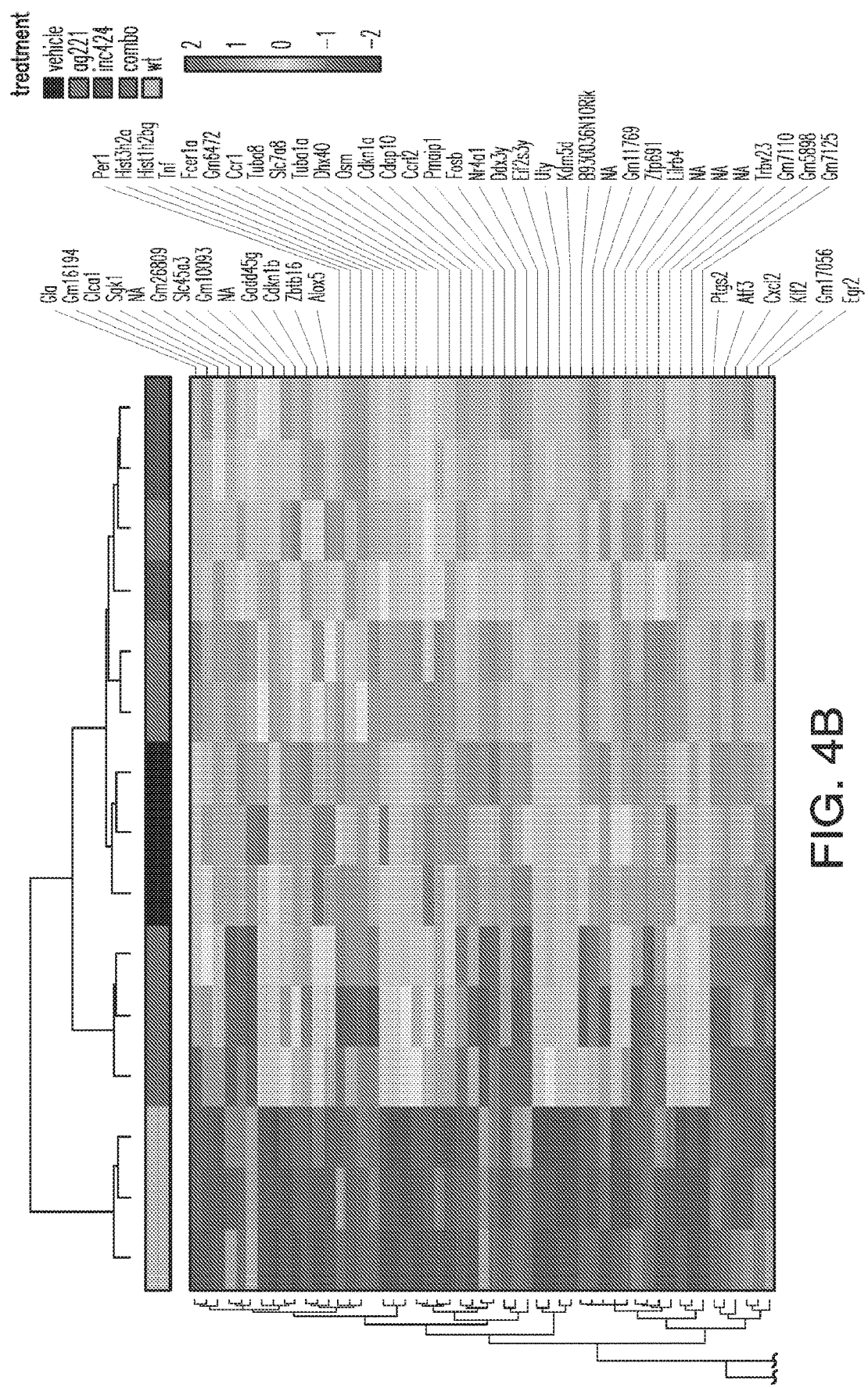
Figure 4B:
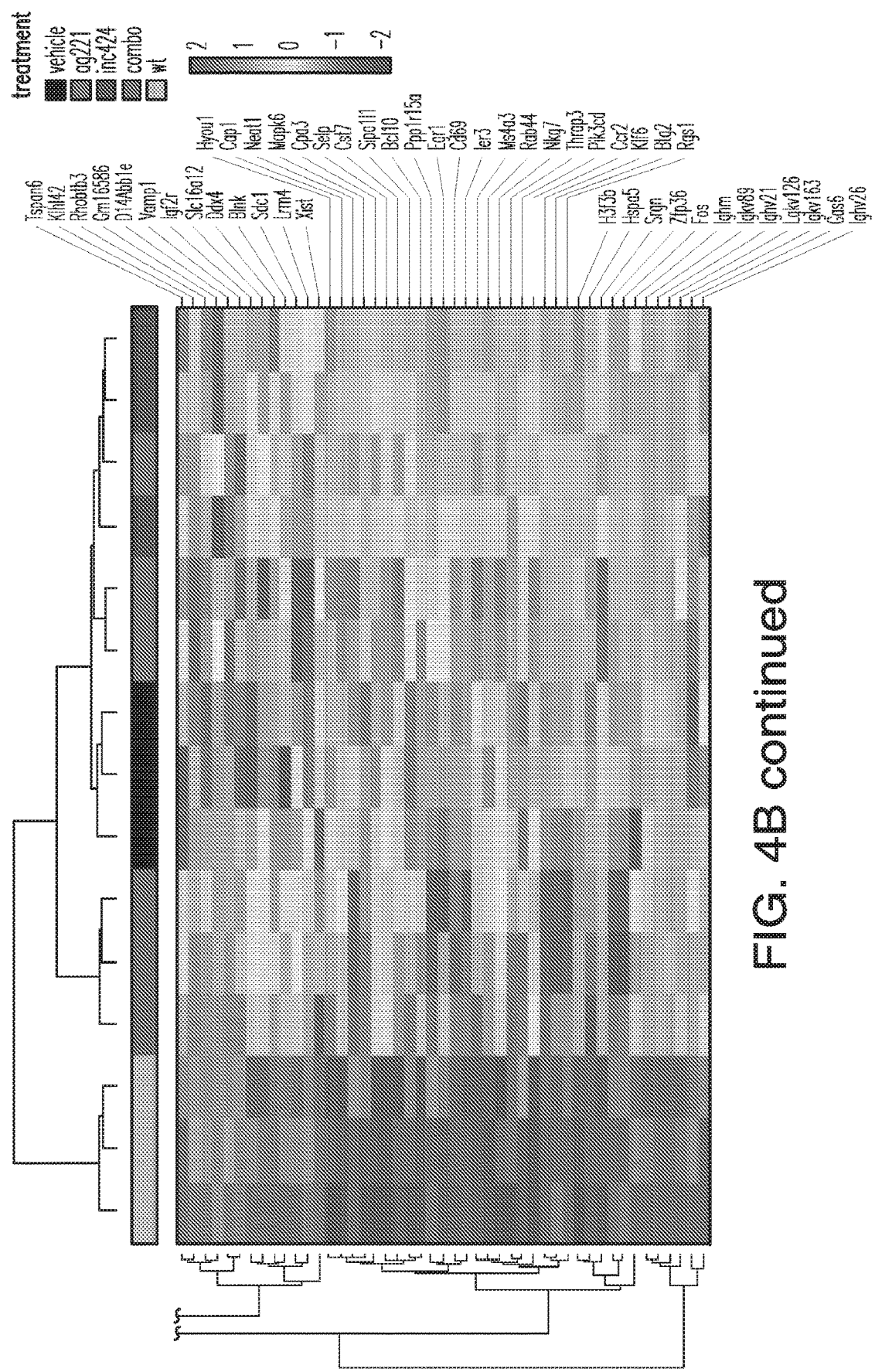
Figure 4C:
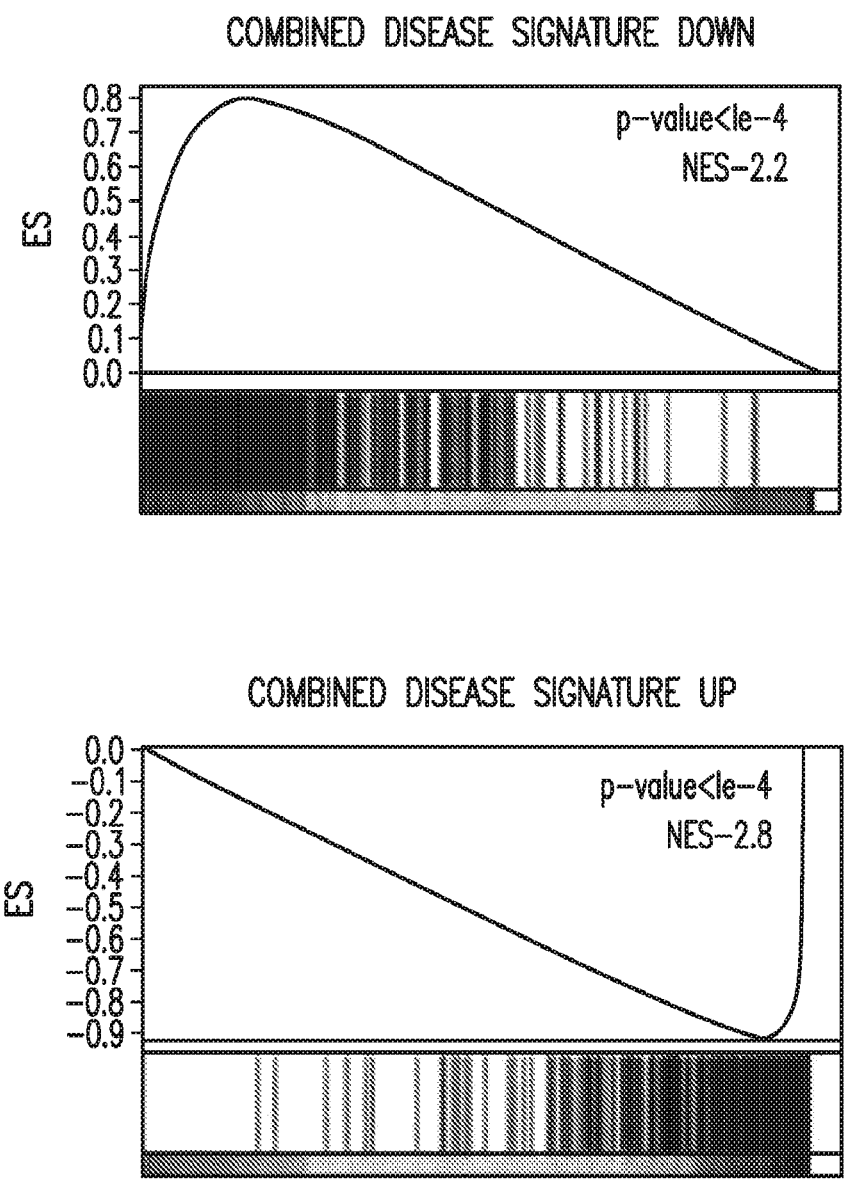

Inhibitor treatment had an impact on aberrant gene expression in $IDH2^{R140Q}$ $JAK2^{V617F}$ mutant LSKs. A more dramatic effect on gene expression with combination JAK2/IDH2 inhibitor therapy was observed than with either monotherapy, such that LSKs derived from mice receiving combination therapy clustered most similarly to wild type LSKs in unsupervised analysis, and in clustering based on differentially expressed genes between diseased and wild type mice (FIG. 4B). Further, examination of expression changes caused by combined treatment showed significant reversal of expression patterns induced by IDH/JAK2 mutations (p-value<1e-4 for both down- and up-regulated genes)(FIG. 4C). A subset of gene expression signatures reversed by combination therapy were also reversed in mice treated with AG221 monotherapy, including both upregulated (p<1e-4, NES=+1.9) and downregulated genes (p<1e-4; NES=−2.3). The combined treatment signature showed significant enrichment of gene signatures that were also significantly altered by ruxolitinib monotherapy (downregulated only; p<1e-4, NES=−2.2), indicating an additive effect of combined treatment on expression changes relative to that induced by each monotherapy.

Figure 4D:
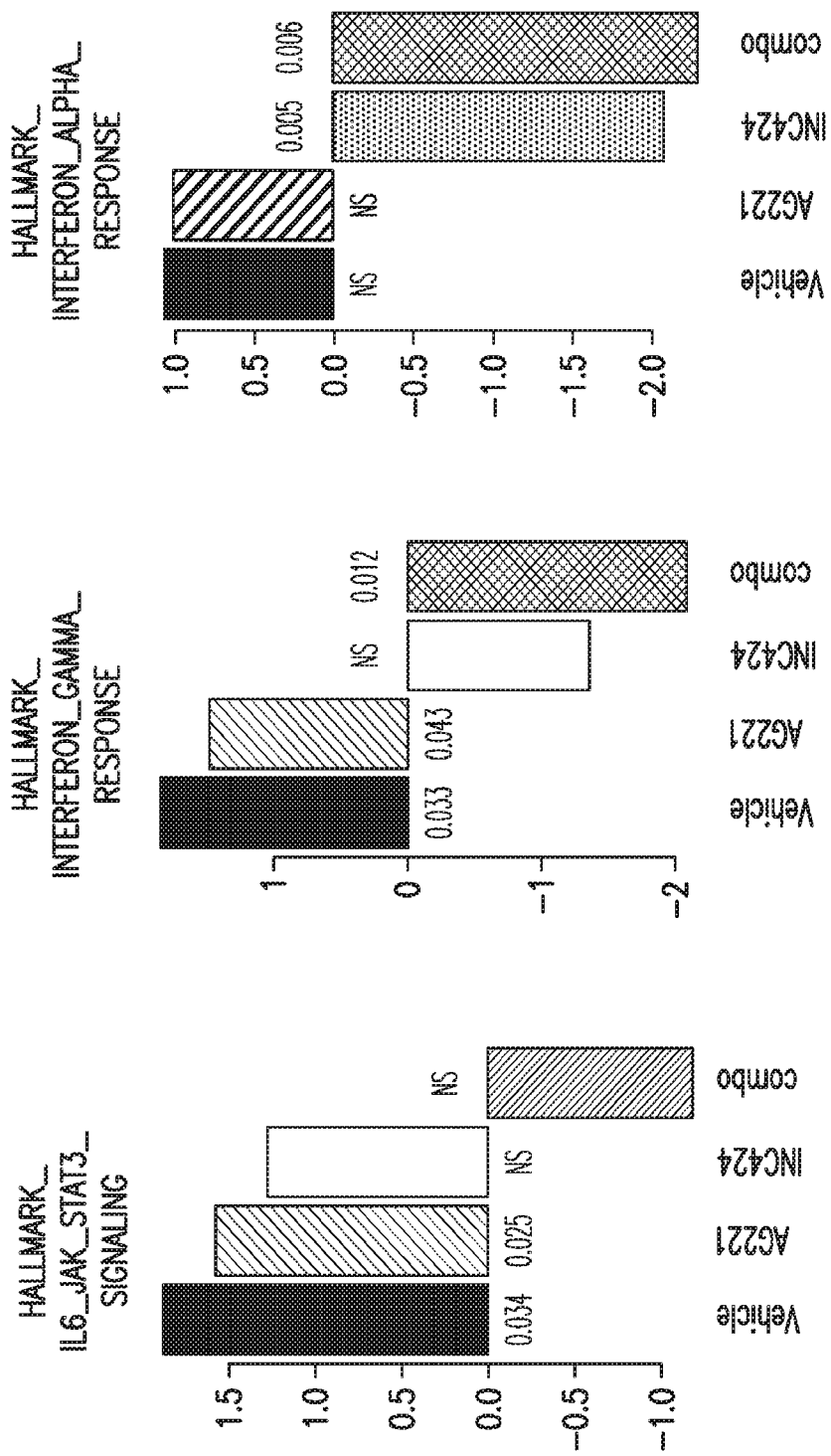
Figure 4E:
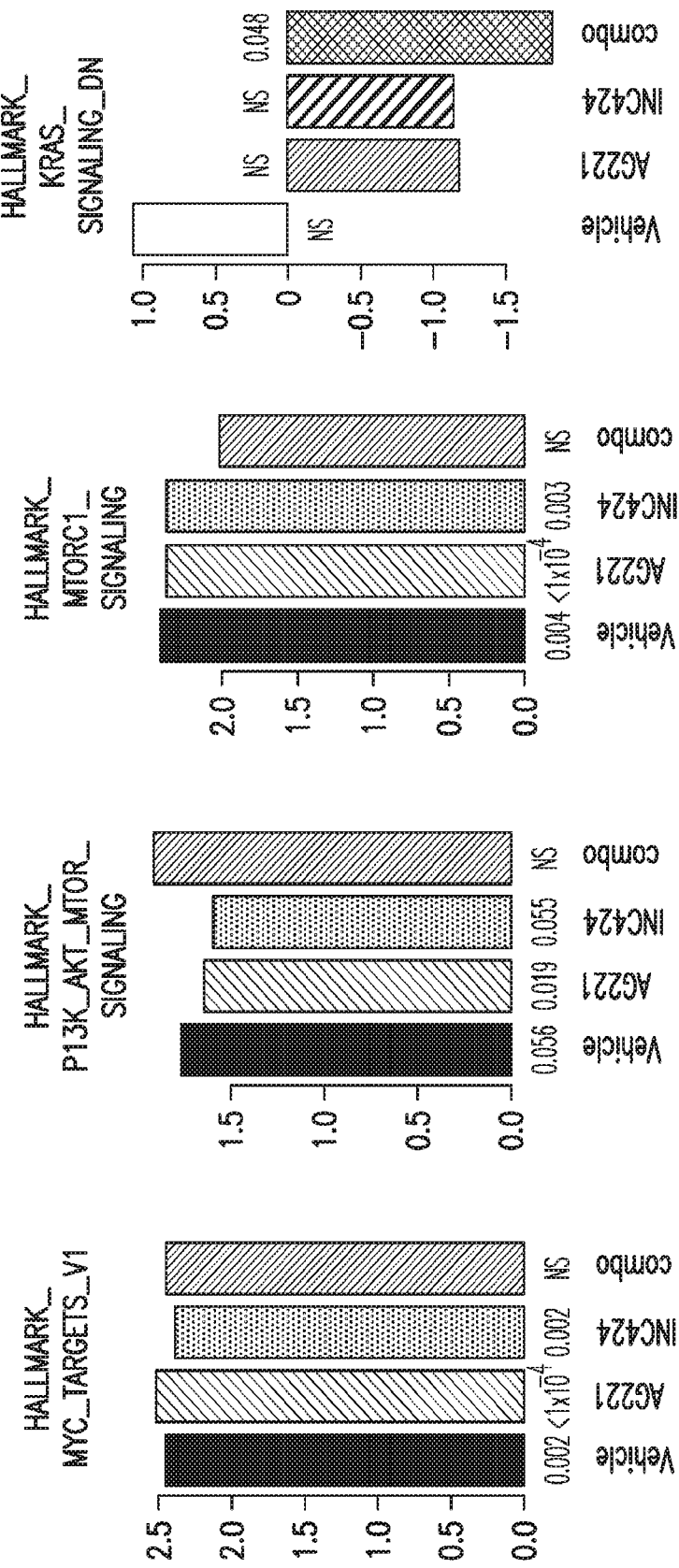
Figure 4F:
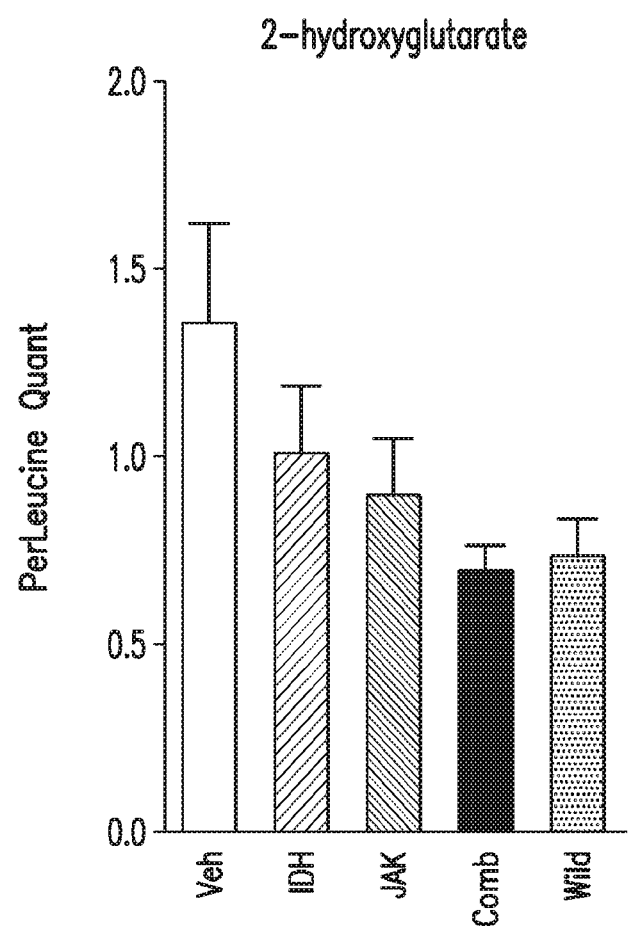
Figure 4G:
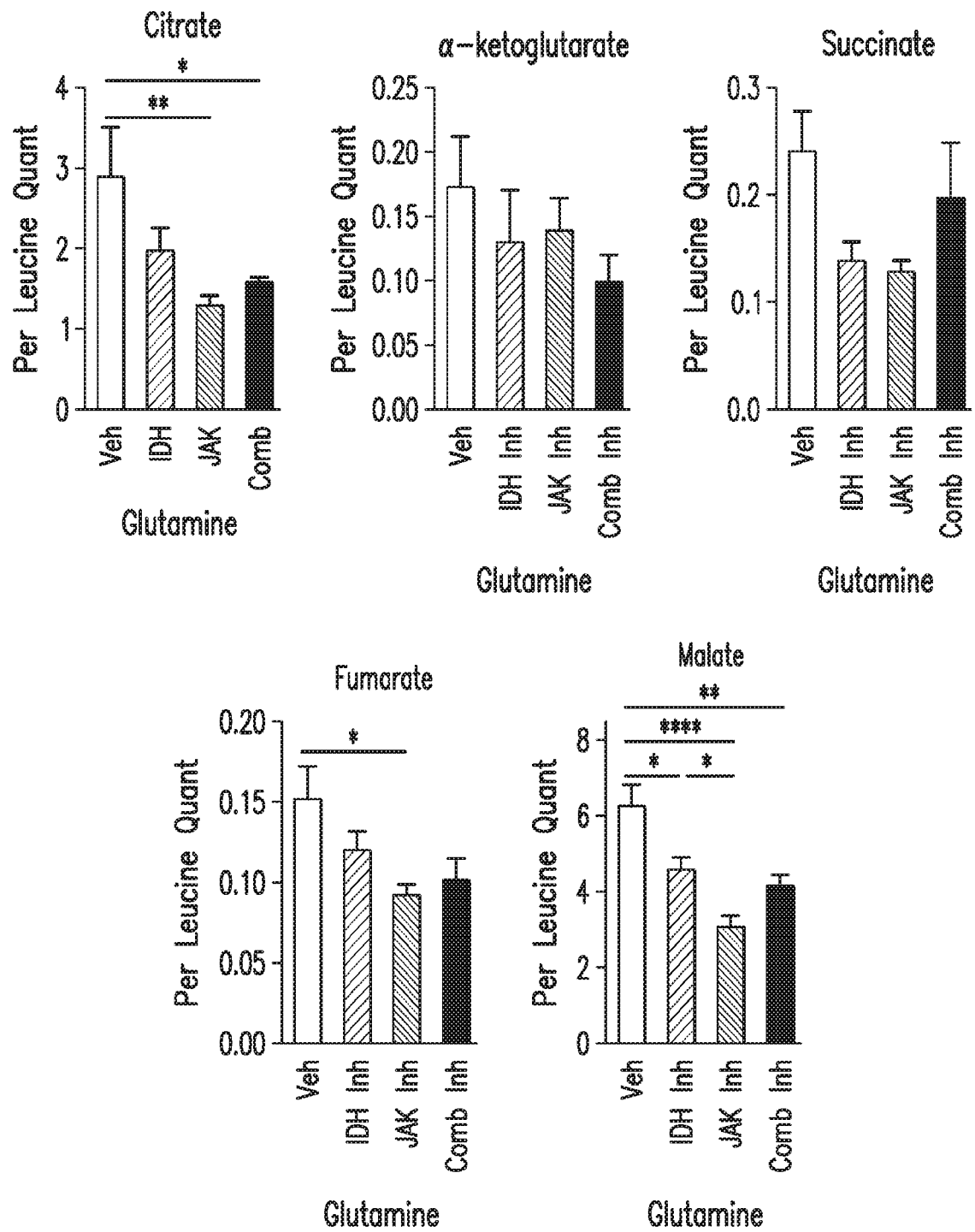

The differentially expressed gene sets were further characterized between each treatment group and wild type bone marrow. Mice treated with ruxolitinib monotherapy showed loss of enrichment of JAK-STAT related gene sets in comparison to vehicle mice. In the case of IL6/JAK/STAT3, enrichment for expression of genes in this pathway were seen in vehicle and in stem cells from mice treated with AG221 monotherapy. However, this gene expression signature was normalized in stem cells from mice treated with ruxolitinib monotherapy or combined therapy. Similarly, interferon gamma signatures, which were significantly enriched in stem cells from mice treated with vehicle or AG221 monotherapy lost significance in animals receiving ruxolitinib monotherapy, and were negatively enriched in mice treated with combination therapy (FIG. 4D). In the context of these findings, several classical oncogene-related gene sets whose gene expression signatures are upregulated in diseased mice and which were reduced/reversed in treated mice were identified, including signatures derived from cMYC, mTOR, and KRAS. In each of these oncogenic signatures, highly significant enrichment was present in stem cells from mice treated with vehicle, AG221 monotherapy, and ruxolitinib monotherapy, however these aberrant gene expression signatures were normalized by combined JAK2/IDH2 inhibitor therapy (FIG. 4G). Together, these data indicate that combined treatment restores a wild type gene expression pattern in LSKs.

Example 6

Figure 4H:
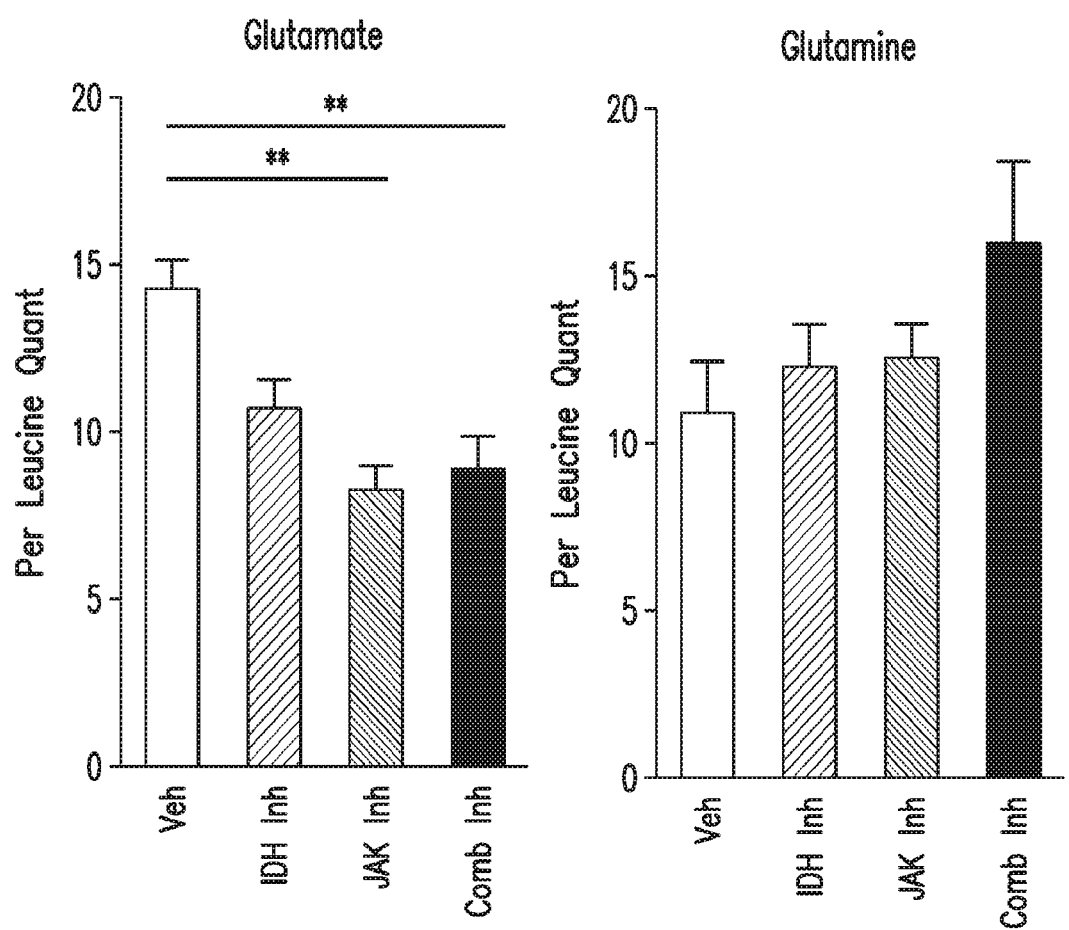

Combined JAK2/IDH2 Inhibition Has Cooperative Effects to Reverse Altered Metabolism in JAK2/IDH2-Mutant MPN The effect of treatment with AG221, ruxolitinib, and combination therapy on JAK2/IDH2-mutant MPN cell metabolism was studied using LC/MS to measure metabolites from mouse bone marrow aspirates after 10 days of treatment with vehicle, ruxolitinib or AG221 monotherapy, or combined therapy. Reduction in 2HG levels with IDH inhibitor monotherapy was first verified (FIG. 4F). IDH inhibitor monotherapy also reduced levels of Kreb's cycle intermediates including a-ketoglutarate, citrate, succinate, fumarate, and malate (p<0.0252; FIG. 4G). 2HG levels were also reduced with ruxolitinib inhibitor monotherapy (FIG. 4F), which is consistent with results observed in the serum of treated mice (FIG. 3A). Ruxolitinib monotherapy also reduced pool sizes of citrate (p=0.0064), fumarate (p=0.0224), and malate (p<0.0001; FIG. 4G). Consistent with observations in serum, mice treated with combined therapy had similar levels of 2HG as wild type mice (FIG. 4F), supporting a combined effect of the two drugs. Reduced glutamate levels with ruxolitinib monotherapy (p=0.0026) and combined therapy (p=0.0049) that was accompanied by a coordinate increases in glutamine, particularly in combined treatment mice (FIG. 4H) was observed. These data provide a potential point of intersection between the JAK2 and IDH2 mutant pathways in the regulation of glutamate/glutamine metabolism.

Example 7

Figure 5A:
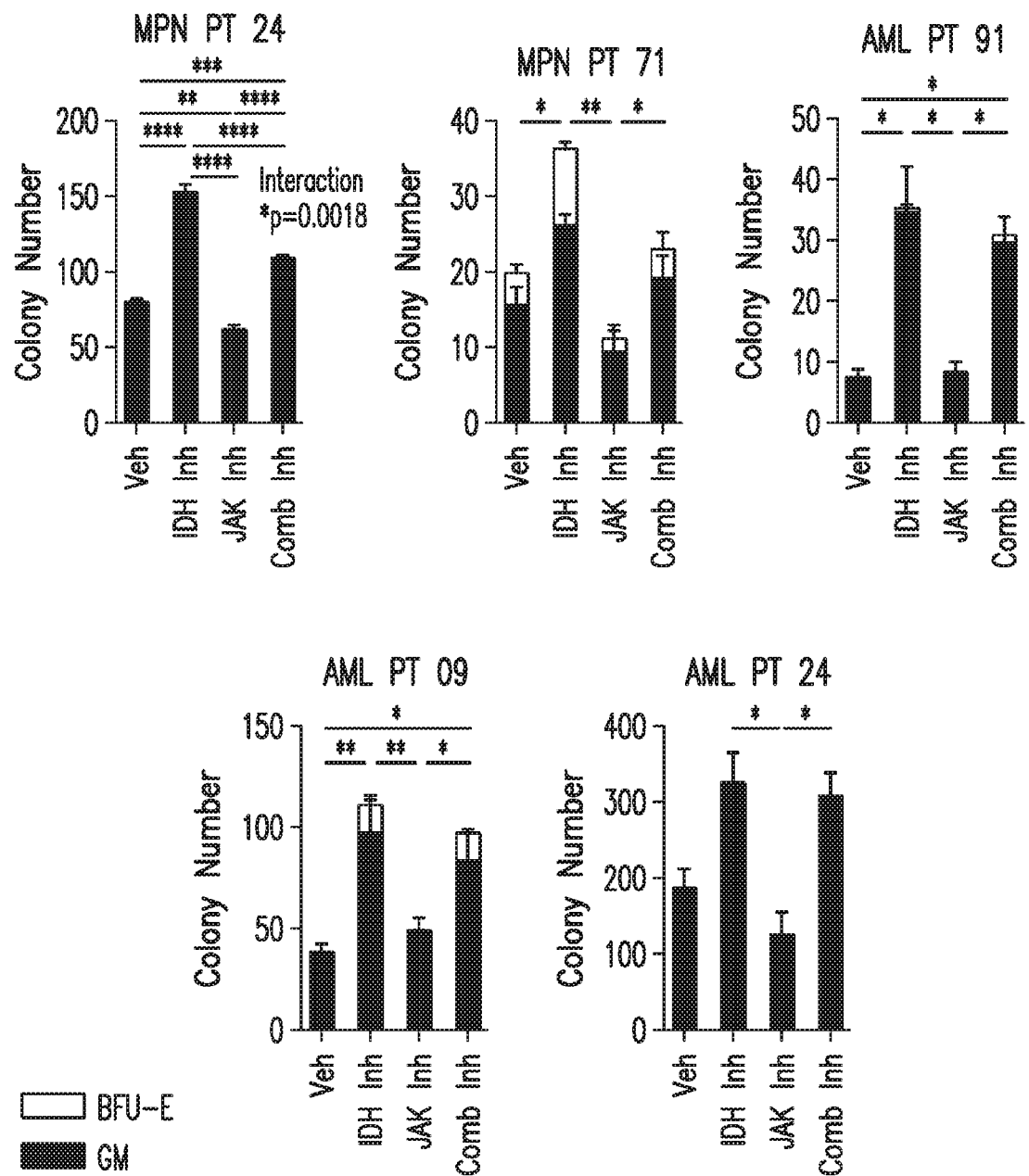
FIGS. 5A-FIG. 5E demonstrate that Human IDH2$^{R140Q}$JAK2$^V$617F MPN and AML samples in methylcellulose respond to IDH inhibitor therapy with differentiation phenotype.
Figure 5B:
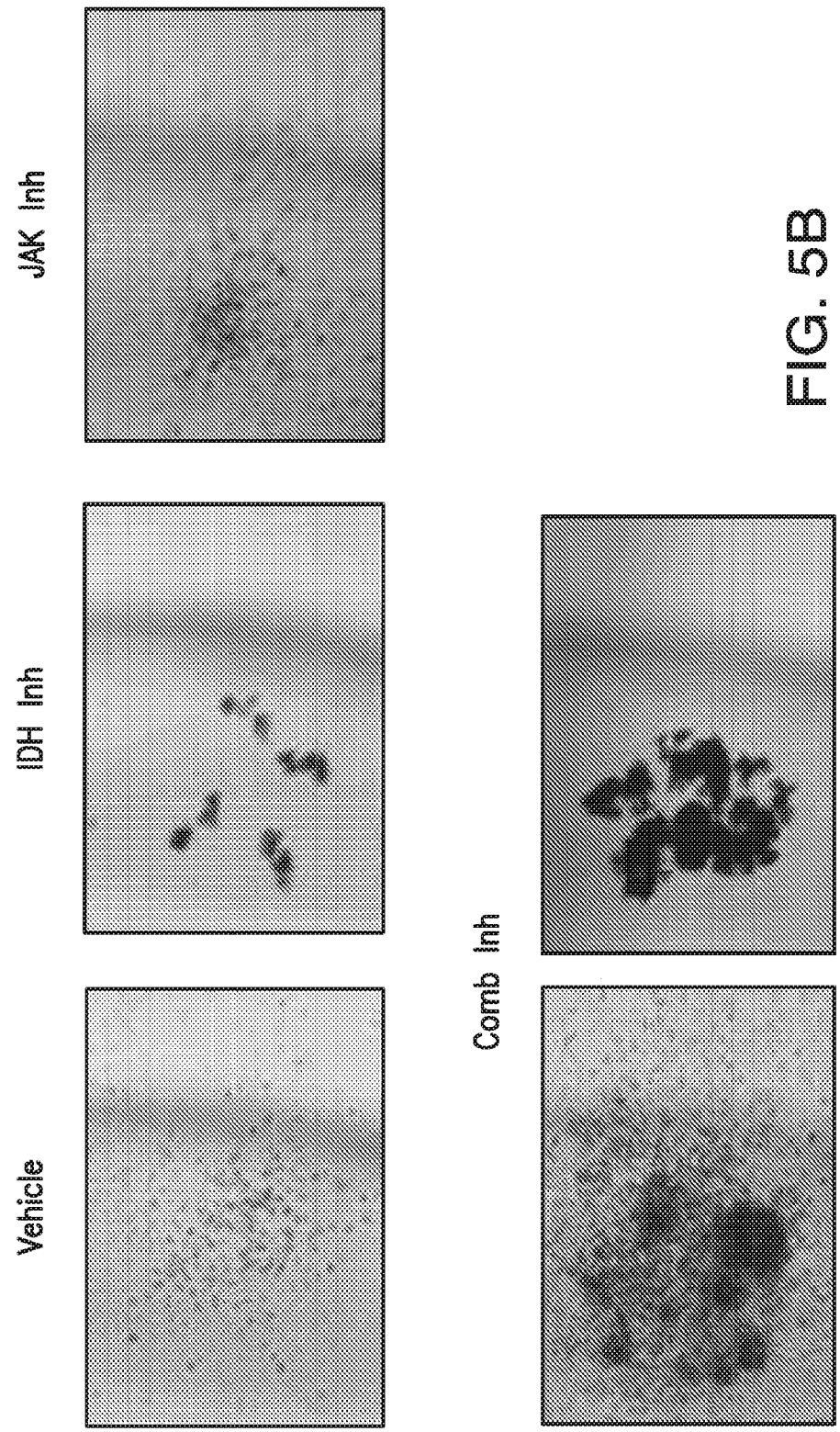
Figure 5C:
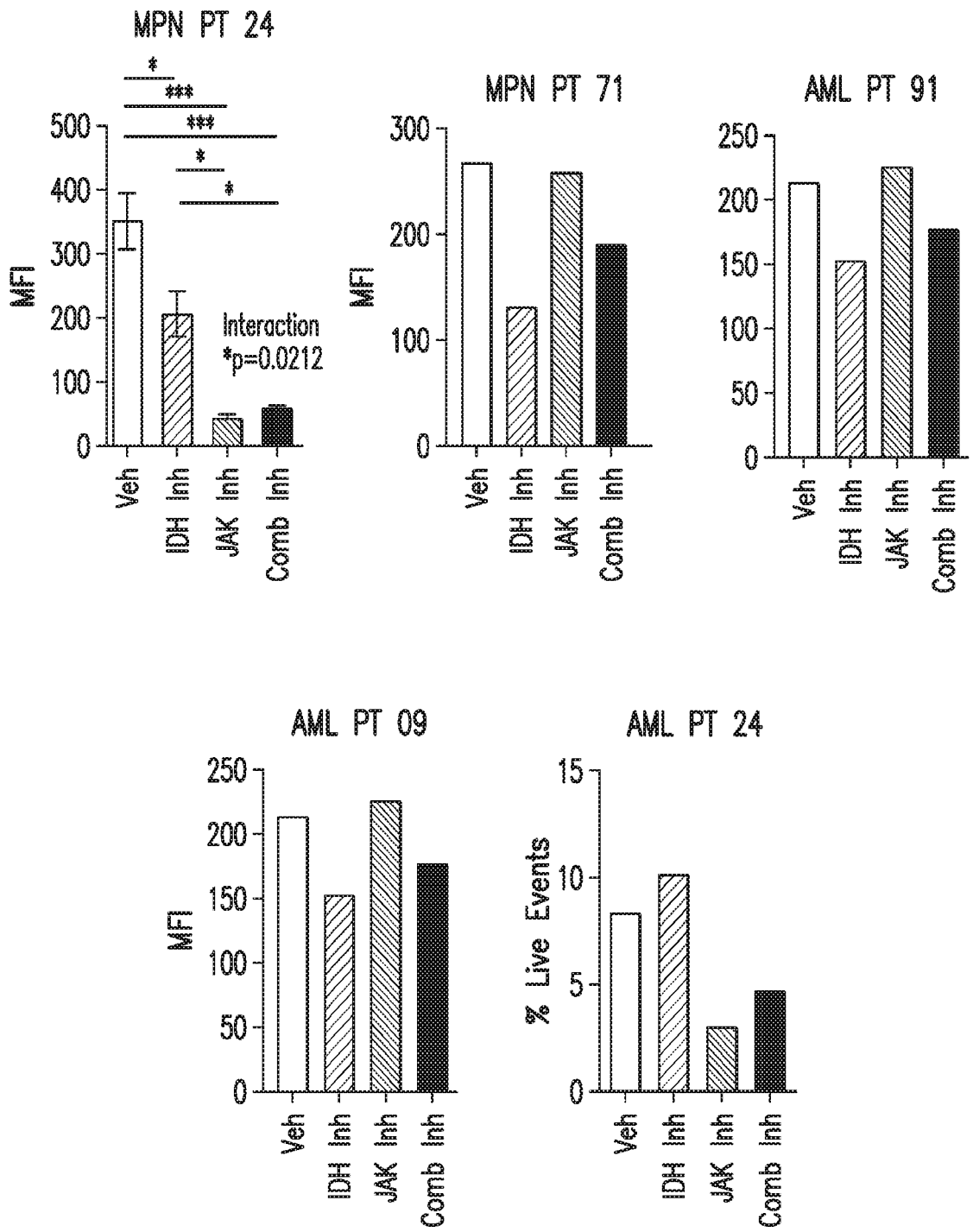
Figure 5D:
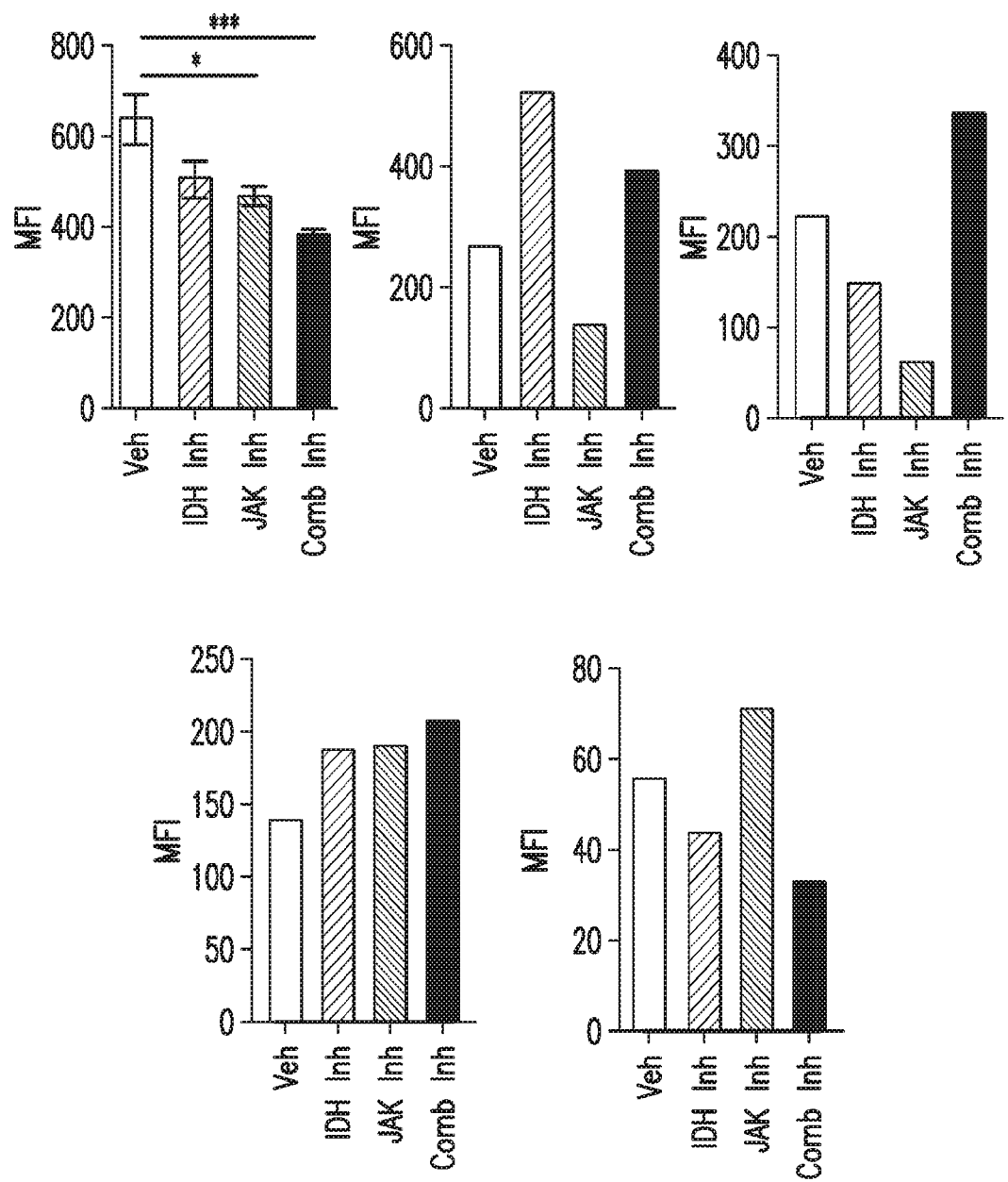
Figure 5E:
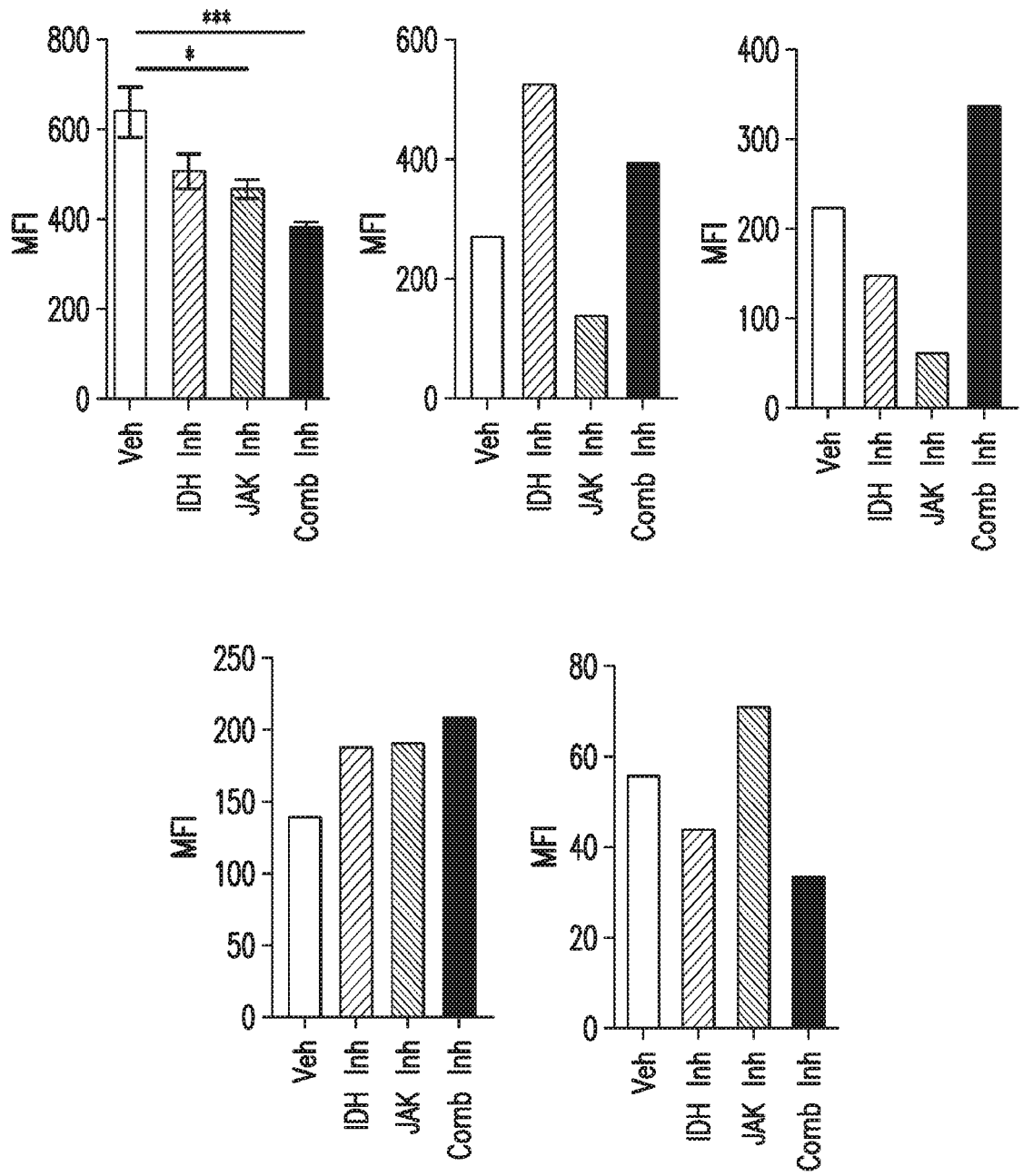

JAK Kinase and Mutant IDH Inhibition Show Cooperative Efficacy in Primary MPN samples from Patients with JAK2/IDH2 Mutations Methylcellulose assays on CD34+ enriched blood samples from patients with clinically determined MPN and Post-MPN AML with $IDH2^{R140Q}$ and $JAK2^{V617F}$ mutations were performed. This analysis included one patient for whom samples from chronic phase MPN and from the time of leukemic transformation (PT 24, FIG. 5) were available. All of the patients showed a characteristic pattern of colony formation with an increase in colony number with IDH inhibitor monotherapy. This expansion was accompanied by the presence of BFU-E colonies consistent with restoration of erythroid differentiation (FIG. 5A) as described by Wang et al. Targeted Inhibition of Mutant IDH2 in Leukemia Cells Induces Cellular Differentiation, *Science* 2013:1-7. On morphological examination this expansion was also associated with the presence of large, well-differentiated colonies in comparison to controls (FIG. 5B). FACS analysis showed that IDH inhibitor treatment reduced the surface expression of the immature marker cKit/CD117 (FIG. 5C). With respect to differentiation markers, it was found that most patient samples treated with AG221 showed upregulation of either the erythroid marker CD235a (FIG. 5D) or the myeloid marker CD14 consistent with restored differentiation in JAK2/IDH2-mutant MPN/AML cells (FIG. 5E). In contrast, it was observed that JAK inhibitor therapy, alone or in combination with IDH2 inhibitor therapy, reduced colony output. Combination treatment attenuated the increase in colony number seen with IDH2 inhibitor monotherapy, while still maintaining the effect of IDH2 inhibition on promoting differentiation as evidenced by a reduction in the proportion of c-Kit positive colonies and an increase in the proportion of CD235a/CD14 positive colonies, which was not seen with ruxolitinib treatment alone. These data suggest that combined JAK/IDH2 inhibitor therapy can have cooperative effects by attenuating proliferation and promoting differentiation.

Having thus described several aspects of several embodiments, it is to be appreciated various alterations, modifications, and improvements will readily occur to thos skilled in the art. Such alterations, modifications, and improvements are intended to be part of this disclosure, and are internded to be within the spirit and scope of the invention. Accordingly, the foregoing descrition and drawings are by way of example only.

What is claimed is:

1. A method of treating a myeloproliferative neoplasm or acute myeloid leukemia in a subject comprising administering to the subject a combination of a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol having the following formula:

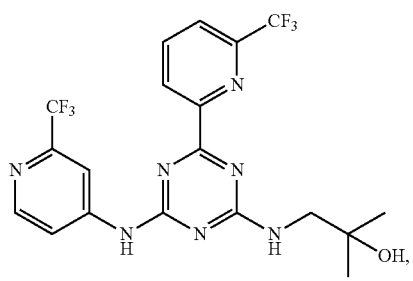 [SMILES: CC(C)(O)CNc1nc(Nc2ccnc(C(F)(F)F)c2)nc(-c2cccc(C(F)(F)F)n2)n1]

or a pharmaceutically acceptable salt, solvate, tautomer, stereoisomer, isotopologue, prodrug, metabolite, or a polymorph thereof (COMPOUND 1) and a therapeutically effective amount of a ruxolitinib, wherein the subject harbors a mutant allele of IDH2 and a mutant allele of JAK2.

2. The method of claim 1, wherein the myeloproliferative neoplasm is selected from polycythemia vera, primary or essential thrombocythemia, primary myelofibrosis, chronic myelogenous leukemia, chronic neutrophilic leukemia, juvenile myelomonocytic leukemia, chronic eosinophilic leukemia and hyper eosinophilic syndrome.

3. The method of claim 1, wherein the mutant allele of IDH2 is mIDH2-R140 or mIDH2-R172.

4. The method of claim 1, wherein the mutant allele of IDH2 is mIDH2-R140.

5. The method of claim 1, wherein the mutant allele of IDH2 is mIDH2-R172.

6. The method of claim 5, wherein the mutant allele of IDH2 is mIDH2-R140Q, mIDH2-R140W, mIDH2-R172K, or mIDH2-R172G.

7. The method of claim 1, wherein the mutant allele of JAK2 is mJAK2-V617F.

8. The method of claim 1, wherein COMPOUND 1 is administered at a dose of about 20 to 2000 mg/day.

9. The method of claim 1, wherein COMPOUND 1 is administered at a dose of about 50 to 500 mg/day.

10. The method of claim 9, wherein the dose is about 60 mg/day.

11. The method of claim 9, wherein the dose is about 100 mg/day.

12. The method of claim 9, wherein the dose is about 150 mg/day.

13. The method of claim 9, wherein the dose is about 200 mg/day.

14. The method of claim 9, wherein the dose is about 300 mg/day.

15. The method of claim 1, wherein COMPOUND 1 is administered once daily.

16. The method of claim 1, wherein COMPOUND 1 is administered for 1 to 25 cycles.

17. The method of claim 1, wherein COMPOUND 1 is administered in 28-day cycles.

18. The method of claim 1, wherein COMPOUND 1 is administered orally.

19. The method of claim 18, wherein COMPOUND 1 is administered once daily orally in a 28-day cycle at the dose of about 100 mg/day.

20. The method of claim 1, wherein COMPOUND 1 is a mesylate salt of 2-methyl-1-[(4-[6-(trifluoromethyl)pyridin-2-yl]-6- {[2-(trifluoromethyl)pyridin-4-yl]amino}-1,3,5-triazin-2-yl)amino]propan-2-ol.

21. The method of claim 1 wherein ruxolitinib is administered in a dose of about 5-25 mg once or twice a day.

22. The method of claim 1 wherein ruxolitinib is administered in a dose of about 5, 10, 15, 20 or 25 mg once or twice a day.

23. The method of claim 1 wherein ruxolitinib is administered orally.

* * * * *